(12) United States Patent
Guney et al.

(10) Patent No.: US 8,839,789 B2
(45) Date of Patent: Sep. 23, 2014

(54) MASK ASSEMBLY

(75) Inventors: Memduh Guney, Killara (AU); Joanne Drew, Balgowlah Heights (AU)

(73) Assignee: ResMed Limited, Bella Vista (AU)

( * ) Notice: Subject to any disclaimer, the term of this patent is extended or adjusted under 35 U.S.C. 154(b) by 193 days.

(21) Appl. No.: 13/423,817

(22) Filed: Mar. 19, 2012

(65) Prior Publication Data

US 2012/0174928 A1 Jul. 12, 2012

Related U.S. Application Data

(60) Continuation of application No. 11/987,616, filed on Dec. 3, 2007, now Pat. No. 8,230,855, which is a division of application No. 10/961,091, filed on Oct. 12, 2004, now Pat. No. 7,318,439, which is a continuation of application No. 10/235,846, filed on Sep. 6, 2002, now Pat. No. 6,823,869.

(60) Provisional application No. 60/342,854, filed on Dec. 28, 2001, provisional application No. 60/317,486, filed on Sep. 7, 2001.

(51) Int. Cl.
*A62B 18/08* (2006.01)
*A61M 16/08* (2006.01)
*A61M 16/06* (2006.01)

(52) U.S. Cl.
CPC ............ *A61M 16/06* (2013.01); *A61M 2206/14* (2013.01); *A61M 16/0825* (2014.02); *A61M 16/0633* (2014.02); *A61M 16/0611* (2014.02); *A61M 16/0616* (2014.02); *A61M 16/08* (2013.01); *A61M 16/0638* (2014.02); *A61M 16/0683* (2013.01)
USPC .................................................... 128/206.24

(58) Field of Classification Search
CPC .... A61M 16/06; A61M 16/08; A61M 16/083
USPC ............. 128/205.25, 206.24, 206.26, 206.28, 128/207.11, 207.14
See application file for complete search history.

(56) References Cited

U.S. PATENT DOCUMENTS

| 35,724 A | 6/1862 | Wilcox |
| 463,351 A | 11/1891 | Elliott |

(Continued)

FOREIGN PATENT DOCUMENTS

| CA | 88122 | 11/1999 |
| DE | 297 21 766 U1 | 3/1998 |

(Continued)

OTHER PUBLICATIONS

European Search Report for EP 02445110.6 dated Nov. 6, 2003 (4 pages).

(Continued)

*Primary Examiner* — Tatyana Zalukaeva
*Assistant Examiner* — Kathrynn Reilly
(74) *Attorney, Agent, or Firm* — Nixon & Vanderhye, P.C.

(57) ABSTRACT

A respiratory mask assembly for delivery of non-invasive positive airway pressure to a user having a rigid mask shell including a plurality of slots; a soft cushion including at least one flexible sealing lip constructed and arranged to extend around an inner periphery of the cushion and to deform to provide a continuous airtight seal between the cushion and the rigid mask shell, the at least one flexible sealing lip being constructed and arranged to return to a relaxed state when the cushion is disassembled from the rigid mask shell, the soft cushion including a retaining portion; and a retaining ring configured to engage with the retaining portion of the cushion, and including a plurality of clips each positioned on respective spring arms to engage with each of the respective plurality of slots of the rigid mask shell to retain the cushion in position with the rigid mask shell.

31 Claims, 91 Drawing Sheets

(56) References Cited

U.S. PATENT DOCUMENTS

| | | | |
|---|---|---|---|
| 715,611 A | 12/1902 | Schnenker et al. |
| 716,530 A | 12/1902 | Giddens |
| 812,706 A | 2/1906 | Warbasse |
| 1,070,986 A | 8/1913 | Richter |
| 1,081,745 A | 12/1913 | Johnston |
| 1,333,075 A | 3/1920 | Hill et al. |
| 1,381,826 A | 6/1921 | Hansen |
| 1,653,572 A | 12/1927 | Jackson |
| 1,672,165 A | 6/1928 | Lewis |
| 1,733,020 A | 10/1929 | Jones |
| 2,029,129 A | 1/1936 | Schwartz |
| 2,033,448 A | 3/1936 | James |
| 2,141,222 A | 12/1938 | Pioch |
| 2,359,506 A | 10/1944 | Battley et al. |
| 2,371,965 A | 3/1945 | Lehmberg |
| 2,454,103 A | 11/1948 | Swidersky |
| 2,638,161 A | 5/1953 | Jones |
| 2,823,671 A | 2/1958 | Garelick |
| 2,832,015 A | 4/1958 | Ortega |
| 2,893,387 A | 7/1959 | Gongoll et al. |
| 2,931,356 A * | 4/1960 | Schwarz ............. 128/206.24 |
| 3,141,213 A | 7/1964 | Nicholas |
| 3,189,027 A | 6/1965 | Bartlett, Jr. |
| 3,474,783 A | 10/1969 | Ulmann |
| 3,494,072 A | 2/1970 | Olson |
| 3,523,534 A | 8/1970 | Nolan |
| 3,535,810 A | 10/1970 | Baehrle |
| 3,555,752 A | 1/1971 | Bogaert |
| 3,726,275 A | 4/1973 | Jackson et al. |
| 3,824,999 A | 7/1974 | King |
| 4,049,357 A | 9/1977 | Hamisch, Jr. |
| 4,064,875 A | 12/1977 | Cramer et al. |
| 4,111,197 A | 9/1978 | Warncke et al. |
| 4,121,580 A | 10/1978 | Fabish |
| 4,164,942 A | 8/1979 | Beard et al. |
| 4,226,234 A | 10/1980 | Gunderson |
| 4,274,404 A | 6/1981 | Molzan et al. |
| 4,275,908 A | 6/1981 | Elkins et al. |
| 4,380,102 A | 4/1983 | Hansson |
| 4,494,538 A | 1/1985 | Ansite |
| 4,506,665 A | 3/1985 | Andrews et al. |
| 4,549,334 A | 10/1985 | Miller |
| 4,580,556 A | 4/1986 | Kondur |
| 4,606,340 A | 8/1986 | Ansite |
| 4,622,964 A | 11/1986 | Flynn |
| 4,633,972 A | 1/1987 | DeRocher |
| 4,676,241 A | 6/1987 | Webb et al. |
| 4,713,844 A | 12/1987 | Westgate |
| 4,783,029 A | 11/1988 | Geppert et al. |
| 4,807,617 A | 2/1989 | Nesti |
| 4,809,692 A | 3/1989 | Nowacki et al. |
| 4,811,730 A | 3/1989 | Milano |
| 4,835,820 A | 6/1989 | Robbins, III |
| 4,841,953 A | 6/1989 | Dodrill |
| 4,870,963 A | 10/1989 | Carter |
| 4,875,714 A | 10/1989 | Lee |
| 4,875,718 A | 10/1989 | Marken |
| 4,898,174 A | 2/1990 | Fangrow, Jr. |
| 4,899,614 A | 2/1990 | Kataumi |
| 4,905,686 A | 3/1990 | Adams |
| 4,944,310 A | 7/1990 | Sullivan |
| 4,946,202 A | 8/1990 | Perricone |
| 4,974,586 A | 12/1990 | Wandel et al. |
| 4,974,921 A | 12/1990 | Miyata et al. |
| 4,997,217 A | 3/1991 | Kunze |
| 5,003,633 A | 4/1991 | Itoh |
| 5,005,568 A | 4/1991 | Loescher et al. |
| 5,054,482 A | 10/1991 | Bales |
| 5,136,760 A | 8/1992 | Sano et al. |
| 5,215,336 A | 6/1993 | Worthing |
| 5,243,971 A | 9/1993 | Sullivan et al. |
| 5,245,995 A | 9/1993 | Sullivan et al. |
| 5,253,641 A | 10/1993 | Choate |
| 5,311,862 A | 5/1994 | Blasdell et al. |
| 5,349,949 A | 9/1994 | Schegerin |
| 5,398,673 A | 3/1995 | Lambert |
| 5,438,981 A | 8/1995 | Starr et al. |
| 5,441,046 A | 8/1995 | Starr et al. |
| 5,501,214 A | 3/1996 | Sabo |
| 5,538,001 A | 7/1996 | Bridges |
| 5,645,049 A | 7/1997 | Foley et al. |
| 5,647,355 A | 7/1997 | Starr et al. |
| 5,676,133 A | 10/1997 | Hickle et al. |
| 5,704,345 A | 1/1998 | Berthon-Jones et al. |
| 5,709,204 A | 1/1998 | Lester |
| 5,724,965 A | 3/1998 | Handke et al. |
| 5,794,617 A | 8/1998 | Brunell et al. |
| 5,839,436 A | 11/1998 | Fangrow et al. |
| 5,860,677 A | 1/1999 | Martins et al. |
| 5,896,857 A | 4/1999 | Hely et al. |
| 5,909,732 A | 6/1999 | Diesel et al. |
| 5,921,239 A | 7/1999 | McCall et al. |
| 5,937,851 A | 8/1999 | Serowski et al. |
| 5,979,025 A | 11/1999 | Horng |
| 6,082,360 A | 7/2000 | Rudolph et al. |
| 6,112,746 A | 9/2000 | Kwok et al. |
| 6,119,693 A | 9/2000 | Kwok et al. |
| 6,189,532 B1 | 2/2001 | Hely et al. |
| 6,192,886 B1 | 2/2001 | Rudolph |
| 6,196,223 B1 | 3/2001 | Belfer et al. |
| 6,240,605 B1 | 6/2001 | Stevens et al. |
| 6,250,375 B1 | 6/2001 | Lee et al. |
| 6,256,846 B1 | 7/2001 | Lee |
| 6,272,722 B1 | 8/2001 | Lai |
| 6,321,421 B1 | 11/2001 | Lim |
| 6,347,631 B1 | 2/2002 | Hansen et al. |
| 6,381,813 B1 | 5/2002 | Lai |
| 6,412,487 B1 * | 7/2002 | Gunaratnam et al. ... 128/206.24 |
| 6,422,238 B1 | 7/2002 | Lithgow |
| 6,449,817 B1 | 9/2002 | Hsu |
| 6,463,931 B1 | 10/2002 | Kwok et al. |
| 6,467,483 B1 | 10/2002 | Kopacko et al. |
| 6,491,034 B1 | 12/2002 | Gunaratnam et al. |
| 6,513,206 B1 | 2/2003 | Banitt et al. |
| 6,520,182 B1 | 2/2003 | Gunaratnam |
| 6,530,373 B1 * | 3/2003 | Patron et al. ............. 128/205.25 |
| 6,532,961 B1 | 3/2003 | Kwok et al. |
| 6,536,435 B1 | 3/2003 | Fecteau et al. |
| 6,615,832 B1 * | 9/2003 | Chen ................... 128/206.26 |
| 6,679,260 B2 | 1/2004 | Her |
| 6,705,647 B1 | 3/2004 | Palmer |
| 6,796,308 B2 | 9/2004 | Gunaratnam et al. |
| 6,823,869 B2 | 11/2004 | Raje et al. |
| 7,318,439 B2 | 1/2008 | Raje et al. |
| 7,827,987 B2 | 11/2010 | Woodard et al. |
| 2002/0023649 A1 | 2/2002 | Gunaratnam et al. |
| 2002/0023650 A1 | 2/2002 | Gunaratnam et al. |
| 2002/0029780 A1 | 3/2002 | Frater et al. |
| 2002/0096175 A1 | 7/2002 | Her |
| 2002/0148472 A1 * | 10/2002 | Barnett et al. ............ 128/206.24 |
| 2002/0153012 A1 | 10/2002 | Gunaratnam et al. |
| 2002/0174868 A1 | 11/2002 | Kwok et al. |
| 2003/0005935 A1 | 1/2003 | Kwok et al. |
| 2003/0075180 A1 | 4/2003 | Raje et al. |
| 2004/0134497 A1 | 7/2004 | Gunaratnam et al. |
| 2006/0042629 A1 | 3/2006 | Geist |
| 2006/0076019 A1 | 4/2006 | Ho |
| 2006/0169286 A1 | 8/2006 | Eifler et al. |
| 2008/0178885 A1 | 7/2008 | Raje et al. |

FOREIGN PATENT DOCUMENTS

| | | |
|---|---|---|
| DE | 297 23 101 U1 | 7/1998 |
| DE | 4 99 00 269.5 | 1/1999 |
| EP | 1027905 | 8/2000 |
| EP | 1057494 | 12/2000 |
| ES | 145309 | 1/2000 |
| FR | 2 691 906 | 12/1993 |
| FR | 99/16 | 8/1999 |
| GB | 2080119 | 12/1998 |
| GB | 2080120 | 12/1998 |
| GB | 2080121 | 12/1998 |
| JP | 48-55696 | 10/1971 |
| JP | 59-55535 | 4/1984 |

(56) References Cited

FOREIGN PATENT DOCUMENTS

| | | |
|---|---|---|
| JP | 61-67747/86 | 5/1986 |
| JP | 7-21058/95 | 4/1995 |
| JP | 7-308381 | 11/1995 |
| JP | 9-501084 | 2/1997 |
| JP | 1105649 | 2/1999 |
| JP | H11-381522 | 11/1999 |
| SE | 65481 | 8/2000 |
| WO | WO 80/01645 | 8/1980 |
| WO | 87/01950 | 4/1987 |
| WO | WO 95/04566 | 2/1995 |
| WO | 98/12965 | 4/1998 |
| WO | WO 98/26830 | 6/1998 |
| WO | 98/30123 | 7/1998 |
| WO | WO 98/48878 | 11/1998 |
| WO | WO 9848878 A2 | 11/1998 |
| WO | WO 99/30760 | 6/1999 |
| WO | 99/61088 | 12/1999 |
| WO | WO 00/38772 | 7/2000 |
| WO | 00/78384 | 12/2000 |

OTHER PUBLICATIONS

ResCare Limited, "Sullivan™ Nasal CPAP System, Nose Mask Clip—User Instructions" May 1990, 1 page.

Office Action issued in related Japanese Appln. No. 2008-318985 (Jun. 14, 2011) w/English translation.

ResMed, Mask Systems Product Brochure, 2 pages, Sep. 1992.

Respironics, Inc. "Nasal Mask System Silicone Contour Mask" Product Instructions, 2 pages, Jun. 1997.

Japanese Office Action English Translation for JP 2000-029094, 3 pages.

Morgenstern et al., Nov. 5, 1998, Breathing Mask, English Translation from the European Patent Office—Description of W09848878 pp. 1-2.

Morgenstern et al., Nov. 5, 1998, Breathing Mask, English Translation from the European Patent Office—Claims of W09848878 p. 1.

* cited by examiner

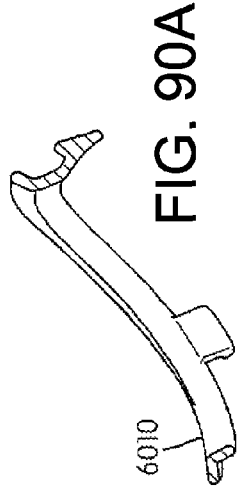
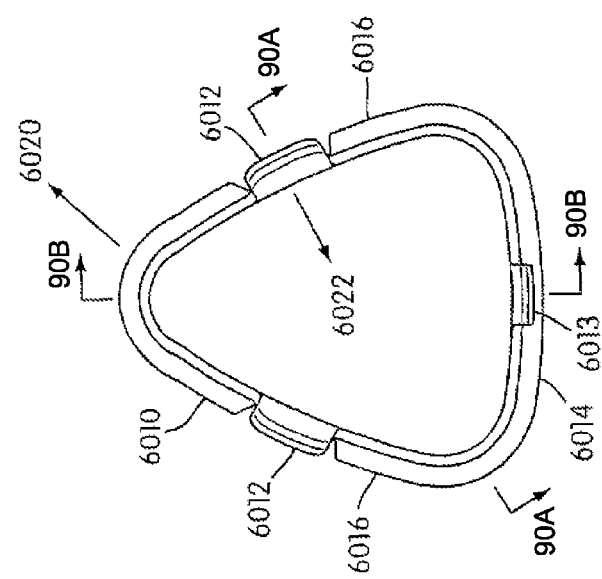
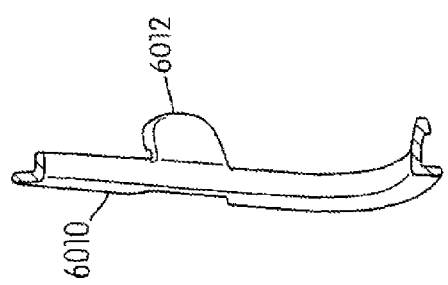
FIG. 90A  FIG. 90B  FIG. 90C  FIG. 90D

MASK ASSEMBLY

CROSS REFERENCE TO RELATED APPLICATIONS

This application is a continuation of U.S. application Ser. No. 11/987,616, filed Dec. 3, 2007, now U.S. Pat. No. 8,230,855, which is a divisional of U.S. application Ser. No. 10/961,091, filed Oct. 12, 2004, now U.S. Pat. No. 7,318,439, which is a continuation of U.S. application Ser. No. 10/235,846, filed Sep. 6, 2002, now U.S. Pat. No. 6,823,869, which claims the benefit of U.S. Provisional Application No. 60/342,854, filed Dec. 28, 2001, and the benefit of U.S. Provisional Application No. 60/317,486, filed Sep. 7, 2001, each incorporated herein by reference in its entirety.

BACKGROUND OF THE INVENTION

1. Field of the Invention

The invention relates to a mask assembly for use in the delivery of Non-invasive Positive Airway Pressure (NPPV) for therapy of Sleep Disordered Breathing (SDB).

2. Background Information

The application of Continuous Positive Airway Pressure (CPAP) for therapy of Obstructive Sleep Apnea (OSA) was first taught by Sullivan in U.S. Pat. No. 4,944,310 (Sullivan). In CPAP treatment for OSA, pressurized air or other breathable gas is provided to the entrance of a patient's airways at a pressure elevated above atmospheric pressure, typically in the range 4 to 20 cm $H_2O$ to "splint" open the patient's airways and prevent obstructive apneas. Apparatus to deliver NPPV therapy typically comprises a blower, an air delivery conduit and a patient interface. The blower may be programmed to deliver a range of different forms of therapy.

In one form, a constant pressure of air or breathable gas is provided to the patient. It is also known for the level of treatment pressure to vary from breath to breath in accordance with patient need, that form of CPAP being known as automatically adjusting nasal CPAP treatment as described in U.S. Pat. No. 5,245,995 (Sullivan and Lynch). In another form, a relatively higher pressure of gas may be provided in the patient mask during the inspiratory phase of respiration and a relatively lower pressure or atmospheric pressure being provided in the patient mask during the expiratory phase of respiration. In other modes, the pressure can be made to vary in a complex manner throughout the respiratory cycle. For example, the pressure at the mask during inspiration or expiration can be varied through the period of treatment. See, for example, U.S. Pat. No. 5,704,345 and International Publication Nos. WO98/12965 and WO99/61088, all of which are incorporated by reference herein. In this specification, the term NPPV therapy will be used to embrace all these forms of therapy.

The patient interface may take many forms, such as a nasal mask assembly, a nose and mouth mask assembly or nasal prongs assembly. A mask assembly typically, but not always, includes a rigid shell, a soft face-contacting cushion, a forehead support and headgear for securing the mask to the head.

In one known mask assembly, the headgear includes a cap portion with four straps. In use, the cap portion engages the occiput of the patient. Furthermore, in use, the two lower straps extend between the cap portion and a nasal mask while the two upper straps extend between the cap portion and a forehead support.

Some patient interfaces include quick release mechanisms. Since the patient must be able to sleep while wearing the patient interface, it must be comfortable. In addition, the patient interface must provide a good seal so any unintentional leak that occurs is minimized and any intentional leak is controlled. Since the shape of people's noses, faces and heads vary widely, from a commercial perspective, it is important to be able to manufacture patient interfaces which can accommodate this range of facial shapes without carrying excessive inventory. A number of patient interfaces have been designed with the goals in mind of patient comfort, ease of use, adjustability and the ability to accommodate a wide range of patient face and head shapes.

U.S. Pat. No. 5,243,971 (Sullivan and Bruderer) provides a nasal mask which is suitable for use in CPAP or NPPV therapy. The mask has a face-contacting portion mounted to a shell which is sized and shaped to overfit the nose region of an intended wearer, and the face contacting portion is in the form of a distendable membrane which is molded from an elastomeric material. The distendable membrane and the shell together define a chamber, and pressurized gas admitted to the chamber causes the membrane to distend outwardly from the shell. When placed in contact with the face of the wearer, the distendable membrane is caused to overlay the covered facial regions and, under the influence of the pressurized gas, to conform three-dimensionally with the contours of the overlayed regions. An orifice is formed within the membrane and is shaped and positioned to admit gas from the chamber to the nasal passages of the wearer. The contents of this patent are hereby incorporated by cross-reference.

U.S. Pat. No. 6,112,746 (Kwok and Styles) describes a nasal cushion which comprises a substantially triangularly shaped frame from which extends a membrane. The frame has a scalloped edge by which the cushion is affixed to a mask body. The membrane has an aperture into which the wearer's nose is received. The membrane is spaced away from the rim of the frame and its outer surface is of substantially the same shape as the rim. Respective notches receive the bridge of the wearer's nose. The wearer's nose is received through the aperture into the chamber within the mask body. The seal forming portion thus contacts both the surface of the wearer's nose and a portion of the wearer's face in the region between the base of the nose and the upper lip, and around the sides and over the bridge of the nose. The shape of the seal forming portion is particularly suited to effectively seal the difficult region of the facial contour that is the crease between the sides of the nose and the face. The contents of this patent are hereby incorporated by cross reference.

U.S. Pat. No. 6,119,693 (Kwok, Matchett and Grant) describes an adjustable forehead support for a nasal mask. An adjustable forehead support for a nasal or full-face mask is described wherein the forehead support may be adjusted for the different shapes and sizes of a facial profile. The forehead support utilizes a dual-arm system which adjusts the position of the forehead support vis-a-vis the mask and/or air flow tube. The angle of the mask to the face may be adjusted with the invention of the '693 patent. The contents of that patent are hereby incorporated by cross-reference.

In international patent application PCT/AU00/00097 (WO 00/78384), a forehead support is disclosed that is adapted to be secured to a respiratory mask. The forehead support includes a joining member for securing to the mask and a cushion frame pivotally mounted to the joining member. The cushion frame is adapted to locate one or more forehead cushions. The cushion frame is also adapted to pivot relative to the joining member. In one form the cushion frame is also selectively lockable at two or more predetermined angular positions relative to the joining member. A respiratory mask assembly comprising a respiratory mask and a forehead support adapted to be secured to the mask is also disclosed. The contents of this specification are hereby incorporated by cross-reference.

Pending U.S. application Ser. No. 09/482,718 (Lithgow), now U.S. Pat. No. 6,422,238 describes headgear for securing a respiratory mask to a patient that incorporates a quick release arrangement. The headgear has at least one strap extending from each side of the mask, the straps being releasably fastened rearwards of the patient's face to secure the mask. The headgear further includes release means in the form of a pull cord attached to an overlying strap at its region of fastening to the underlying strap and guided forward to be gripped at the front of patient. The contents of this specification are hereby incorporated by cross-reference.

A mask cushion for use with a mask assembly in NPPV therapy is disclosed in U.S. patent application Ser. No. 09/885,445, "Mask with Gusset" to Frater et al. filed on Jun. 21, 2001, now U.S. Pat. No. 6,986,352 and assigned to the assignee of the present application, which application is incorporated by reference herein. The mask system disclosed therein includes a suspension mechanism to allow relative movement between a face-contacting cushion and a mask shell. The suspension mechanism also provides a predetermined force to the cushion that is a function of mask pressure, displacement of the cushion or both. In one embodiment of that invention, the mask cushion assembly includes an inflatable gusset acting as the suspension mechanism.

SUMMARY OF THE INVENTION

It has been a problem in the art to stabilize a mask frame (or shell) in a position over the user's face so that the face-contacting side of the cushion is free to move relative to the frame-contacting side of the cushion while maintaining a seal. It is desirable to correct this problem in such a way that is comfortable for the patient and does not create excessive forces on the face of the user because of over-tightened straps.

In one aspect, the present invention discloses a head mount arrangement which is adapted to floatingly stabilize a mask frame in position without the use of a forehead support.

In another aspect, the present invention discloses a head mount arrangement which applies very small forces on the face through the mask frame until the mask is pressurized. In another aspect, the present invention discloses a force-passive or force-neutral mounting arrangement for a mask. In another aspect, a head mount arrangement is disclosed which allows adjustment of the angle and/or distance between the head mount and mask frame (or shell). In another aspect a method of stabilizing on a face a mask assembly comprising flexible straps and a semi-rigid head mount is provided, the method comprising positioning the head mount on a patients head, loosely adjusting the straps length and then applying pressure to the mask assembly.

An additional problem in the art has been that the cushion of a mask assembly is not easily attachable, removable and/or re-attachable to/from the shell. It is desirable for a user to be able to easily assemble, disassemble and/or reassemble the cushion and shell assembly for periodic cleaning and other miscellaneous purposes.

In one aspect, the present invention discloses a retaining ring which provides a secure, sealed connection between the cushion and the shell and is further easily disassembled from the shell for cleaning or other purposes.

An additional problem in the art occurs for a user of a respiratory mask to maintain a previously set strap adjustment position on the mask especially given the fact that it can be quite time consuming to correctly adjust strap positions on the mask. More particularly, in some respiratory mask assemblies, once the user had properly adjusted the mask and needed to remove the mask, there was no way to maintain the previously set positions.

In another aspect, the present invention discloses latching mechanisms which provide for a low-profile attachment between the shell of the mask and the harness and permit the mask to be to quickly, accurately and easily released and latched for use. Thus, the latching mechanisms allow the user to remove and reinstall the mask assembly and maintain the same preset strap adjustment.

The swivel and elbow arrangements of the prior art present problems for the air connections between a pressurized air source and the mask such as leakage around the elbow. The arrangements also suffer from tube drag which can cause the seal between the mask and user's face to break. Some prior art swivel and elbow arrangements use and tight tolerances, which result in heavy friction in the movement of the ball and thus reduced mobility and flexibility of the elbow swivel joint. In another aspect, the mask assembly of the present invention includes a ball and socket joint for breathable air connection to the mask that reduces the effects of tube drag and provides increased flexibility between the air supply tube and the mask. In particular, the ball and socket joint of the present invention allows an air supply tube to be moved on an increased area of movement in comparison to the conventional elbow swivel joint.

In an embodiment of the present invention, the mask assembly includes a rigid shell, a cushion for attachment to the shell and a harness or headgear for attaching the cushion and shell to the patient (or user). The shell includes one or more latching mechanisms for attachment between the shell and the harness and for allowing the harness to be quickly, accurately and repeatedly tightened and untightened with respect to the user's head while maintaining a preset harness length and fit. The latching mechanisms operate on an over center principle to quickly and easily be manipulated by the user (or a care-giver) from an open (or unlatched) position to a closed (or latched) position, and vice-versa.

The shell assembly further includes several features for improving the flow of gases (including air) through the mask and reducing noise levels associated with such gas flow. One such feature is the provision of exhalation ducts that direct the exhalation gas flow from an interior of the mask assembly to an exterior of the mask assembly in a flow direction alongside an air inlet tube to the mask. Another such feature is the provision of one or more baffles in an interior of the shell to direct and help keep separated the intake and exhalation gas flows.

The mask assembly also includes several features for quickly adjusting the fit of the mask assembly to the particular user to improve the sealing of the mask and the comfort of the user. Several different embodiments of adjustment mechanisms are disclosed, including mechanisms that can quickly and easily change the height and/or angle of a head mount with respect to the shell either simultaneously or independently of one another and mechanisms that can alter the fit of the connection between the shell assembly and the harness or headgear. In one embodiment of the present invention, the structure used for securing the shell/cushion assembly to the user's head does not include a forehead support and does not contact the user's forehead and also has the advantage of not leaving unsightly (though usually temporary) pressure marks on the user's forehead as can other known masks.

In another embodiment, a ball and socket joint is provided that permits freedom of movement of a pressurized gas supply tube with respect to the mask assembly, thus preventing the movement of the gas supply tube from affecting the stability of the cushion and shell assembly and the integrity of the mask/face seal. The ball and socket joint may be positioned at some point in the air supply line to provide a highly flexible joint in the line for patient comfort.

Of course, portions of the aspects may form sub-aspects of the present invention. Also, various ones of the sub-aspects and/or aspects may be combined in various manners and also constitute additional aspects or sub-aspects of the present invention. These and other features and aspects of the present invention will be described in or be apparent from the detailed description below read in conjunction with the attached Figures, where like reference numerals indicate like components.

BRIEF DESCRIPTION OF THE FIGURES

The above and other features and advantages of the present invention are further described in the detailed description which follows, with reference to the drawings, and by way of non-limiting exemplary embodiments of the present invention wherein:

FIGS. 90A-90D shows multiple views of the retaining ring in an alternate embodiment of the present invention;

DETAILED DESCRIPTION

Figure 1:
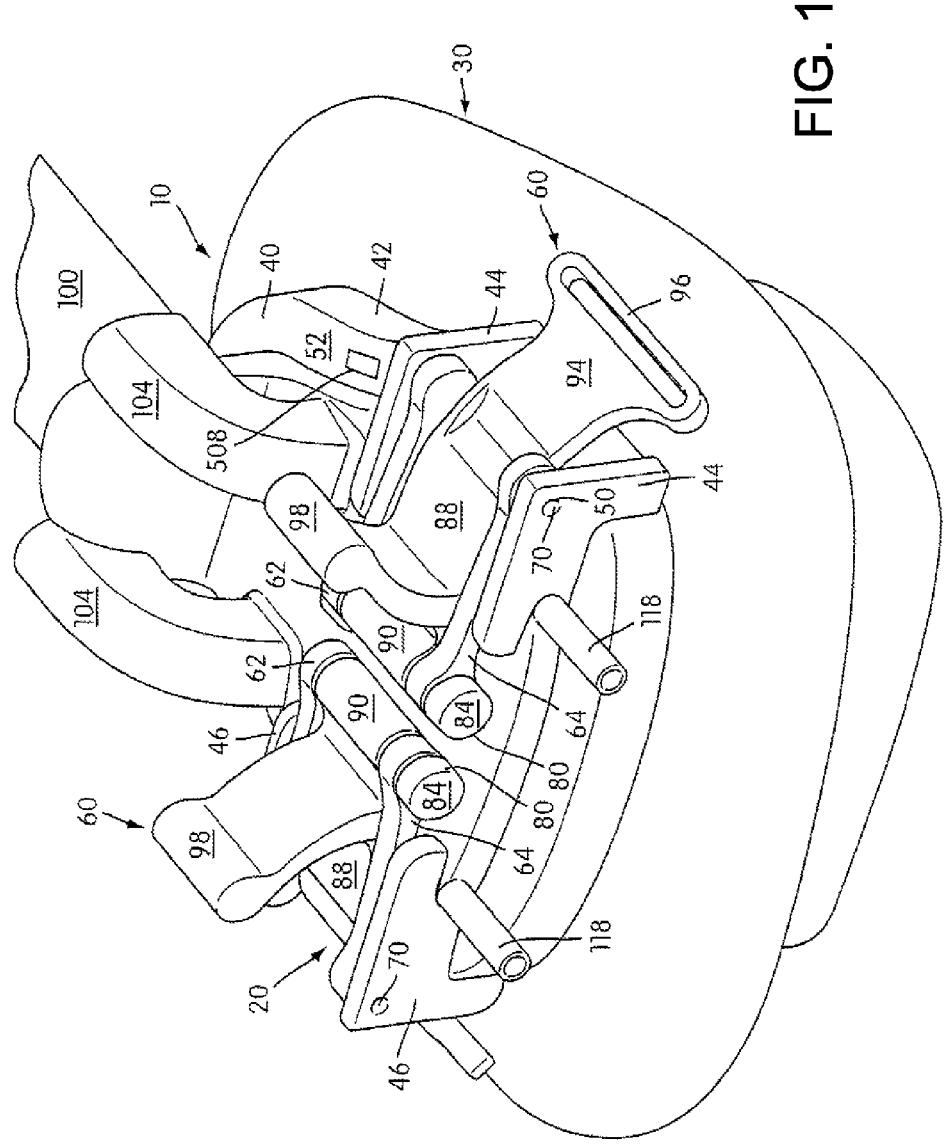
FIG. 1 shows a perspective view of a mask assembly of the present invention.

FIG. 1 shows a perspective view of the mask assembly 10 of the present invention. The mask assembly 10 includes a shell assembly 20 and a cushion 30. One example of the type of cushion with a gusset that can be used with the present invention is disclosed in U.S. patent application Ser. No. 09/885,445, "Mask with Gusset" to Frater et al. filed on Jun. 21, 2001, now U.S. Pat. No. 6,986,352 and assigned to the assignee of the present application, which application is incorporated by reference herein. In the Frater application, a good seal with the face may be obtained under a variety of pressures without the need to over tighten the straps of the mask. The gusset of the cushion disconnects the frame contacting side of the cushion from the patient contacting side of the cushion and allows 6 degrees of freedom between the two sides. However, the present invention is not restricted to use with such a cushion with a gusset and can be used with any NPPV therapy cushion. It should be understood that even where a Figure described herein does not show a cushion, only shows a portion of a cushion or only a gusset portion of a cushion, it is understood that such embodiment is intended to be used with a complete cushion and the use of the term cushion in describing a Figure that only shows a portion of a cushion is not intended to be limiting.

Figure 2:
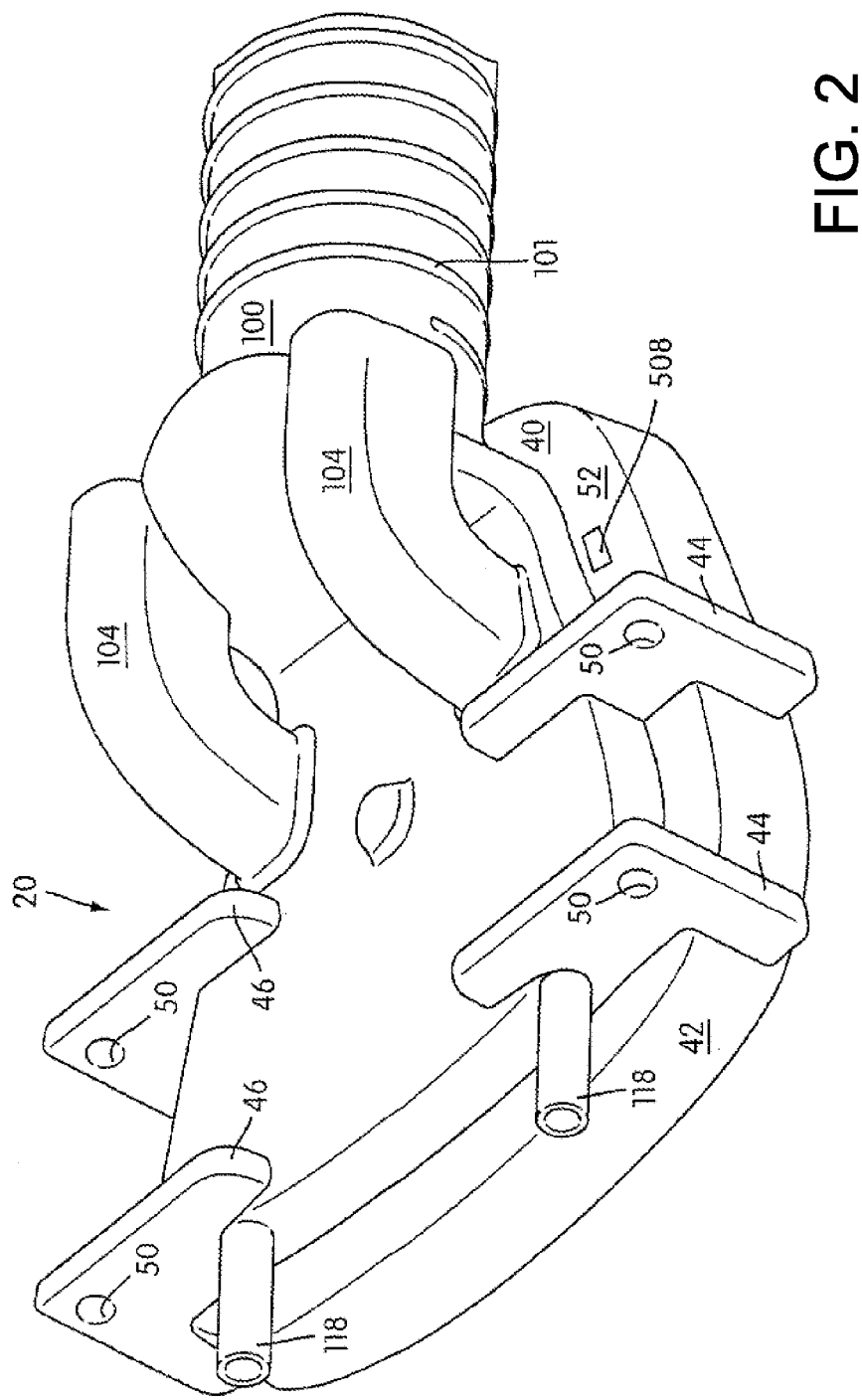
FIG. 2 shows a front perspective view of a shell of the mask assembly of FIG. 1.

The shell assembly 20 includes a generally rigid shell 40 to which the cushion 30 can be attached. The shell 40 includes a base 42 and a pair of flange assemblies 44 and 46 extending upward from the base 42. In the preferred embodiment, the flange assemblies 44 and 46 are generally mirror images of one another, although they need not be. Each of the flange assemblies 44, 46 includes an upper flange and a lower flange with a bore 50 passing therethrough, the bore preferably having an axis parallel to a major planar surface 52 of the shell 40. See also FIG. 2.

Quick Release Latching Mechanism

Figure 4:
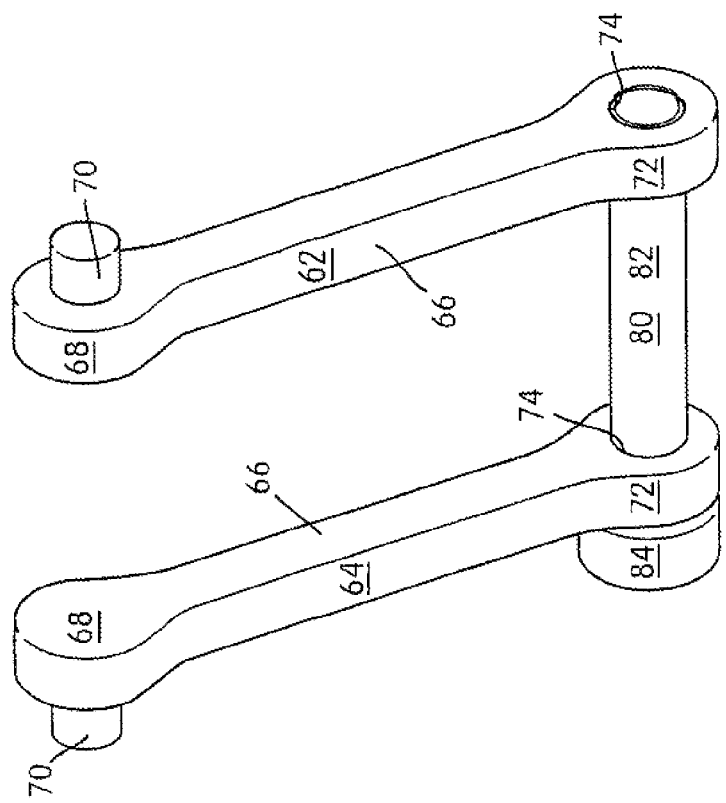
FIG. 4 shows a perspective view of the portion of the latching mechanism of FIG. 3.
Figure 3:
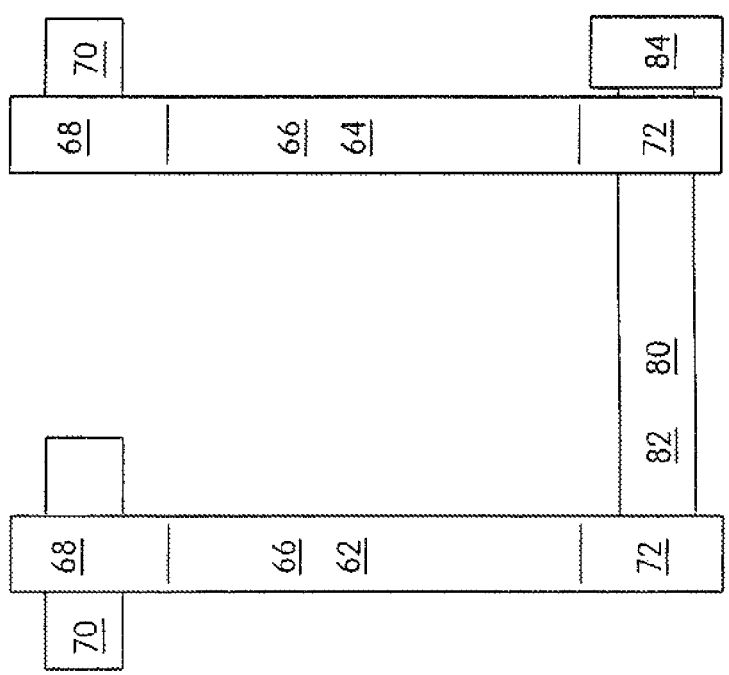
FIG. 3 shows a plan view of a portion of a latching mechanism of the mask assembly of FIG. 1.
Figure 5:
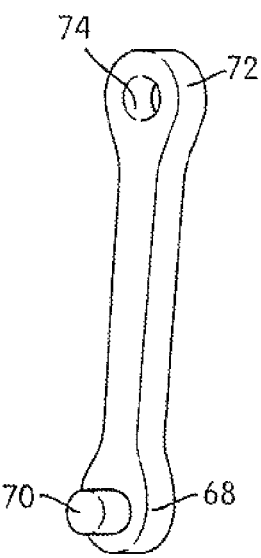
FIG. 5 shows a perspective view of a clip link of the latching mechanism of FIG. 3.

Each of the flange assemblies 44 and 46 support a quick-release latching mechanism 60. Each latch mechanism 60 preferably uses identical components to minimize the number of parts required to manufacture the mask assembly, although the components can be different where desirable. Each latching mechanism 60 includes an upper clip link 62 and a lower clip link 64, which are preferably identical but are reversed upon installation in the shell 40. See also FIGS. 3-6. Each clip link 62, 64 includes an axially extended body 66 with a first end 68 having a pivot pin 70 extending outward from the axially extended body 66 and having an axis perpendicular to an axis of the body 66. The pivot pins 70 are sized and adapted to pivotally engage the respective bores 50 in the flange assemblies 44, 46. As illustrated in FIG. 4, each clip link 62, 64 also includes a second end 72 having a bore 74 therethrough, the bore 74 having an axis parallel to the axis of the pivot pin 70.

Figure 6:
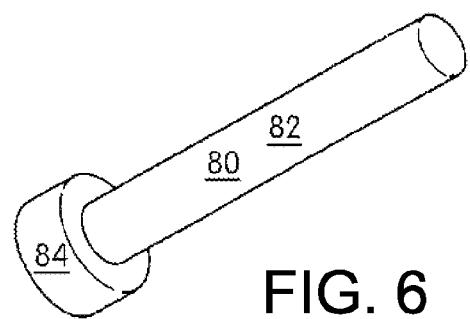
FIG. 6 shows a perspective view of a clip pin of the latching mechanism of FIG. 3.

In FIG. 6, each latching mechanism 60 also includes a clip pin 80 having an axially extending shaft 82 and an enlarged head 84. The axially extending shaft 82 is sized and adapted to pivotally engage the bores 74 of the respective upper and lower clip links 62 and 64, respectively, of each assembly. The enlarged head 84 provides a more easily graspable surface to assemble and disassemble the pin with respect to the latching mechanism and also provides an alignment surface to prevent the pin from passing too far through the bores 74.

Figure 7:
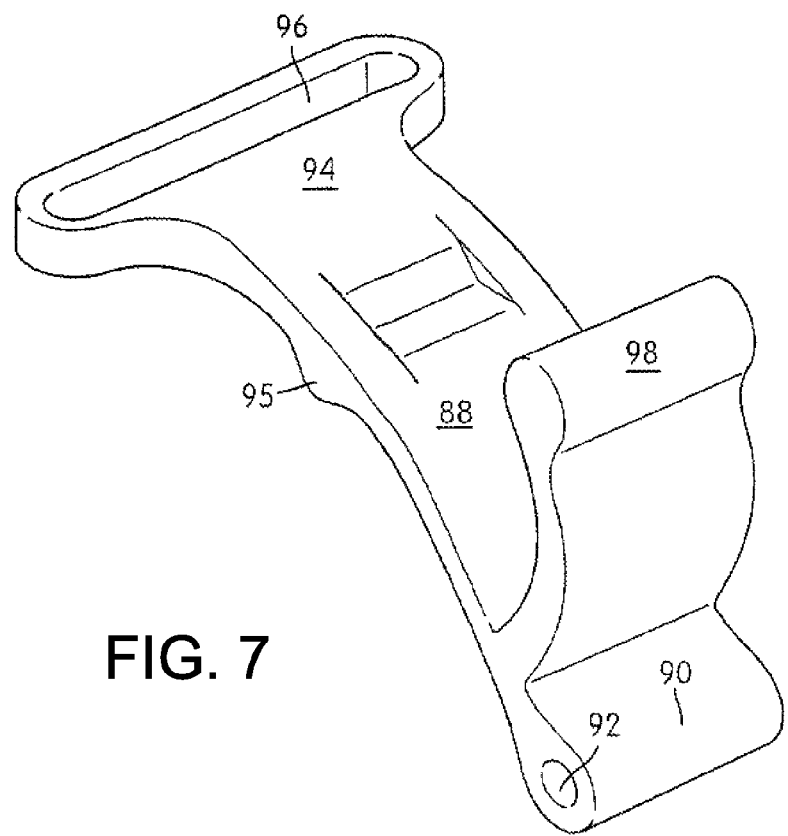
FIG. 7 shows a perspective view of a clip portion of a latching mechanism of the mask assembly of FIG. 1.

As shown in FIG. 7, each latching mechanism 60 also includes a clip 88. Each clip 88 includes a first end 90 having a bore 92 therethrough sized and adapted to pivotally mount over the axially extending shaft 82 of the clip pin 80 between the upper and lower clip links 62 and 64. Each clip 88 also includes a second end 94 that includes a mask harness-engaging portion 96. The harness-engaging portion 96 preferably extends away from a central portion of the clip 88 at an angle toward a face side of the mask 10 generally in alignment with an angle of the harness portion extending from the user's head toward the harness-engaging portion 96. See FIG. 8A. Thus, the harness will exert a pulling force $F_H$ on the harness-engaging portion 96 of the clip 88 that is generally aligned with the angle of the harness-engaging portion 96. In an embodiment, the harness-engaging portion 96 may be a slot through which a portion of the harness can pass to be secured to the clip 88. In one embodiment, the harness may include an engaging strap that can pass through the harness-engaging portion 96 and then be connected to itself by use of Velcro®, snap connections, buckles or other known connections. Each clip 88 includes a flip arm 98 extending away from a body of the clip 88 that is easily graspable by the mask user to manipulate the clip 88 with respect to the mask 10. Each clip 88 may optionally be provided with a stop surface 95 that may be adapted to engage the shell 40 or other fixed portion of the shell assembly 20 to provide a positive stop to movement of the clip 88 in a direction toward the shell 40.

Each latching mechanism 60 may be assembled to the shell 40 as follows. The upper and lower clip links 62 and 64 are first pivotally mounted to the respective upper and lower flanges of the flange assemblies 44, 46 by engaging the respective pivot pins 70 with the respective portion of the bores 50 passing through the upper and lower flanges. The clip 88 is then inserted between the upper and lower clip links 62 and 64. The width of the clip 88 is established so that once the clip 88 is inserted between the upper and lower clip links 62, 64, the clip 88 will prevent the clip links 62, 64 from disengaging from the respective flanges 44, 46. The bore 92 of the clip 88 is then aligned with the respective bores 74 of the upper and lower clip links and the clip pin 80 is inserted through each of the bores to pivotally mount the clip 88 with respect to the clip links 62, 64 and the flange assemblies 44, 46.

The operation of the latching mechanism 60 will now be described. The latching mechanism 60 works on an over-center principle. That is, when a pulling force $F_H$ from the harness is applied to the harness-engaging portion 96 of the clip 88, the clip 88 will have a tendency to move in a direction away from a force equilibrium or force center position of the latching mechanism. In the embodiment shown in FIGS. 8A-8C, the force equilibrium or force center is on a line intersecting the axes of the shaft 82 and the pins 70. If the summation of forces acting on the clip 88 result in a summed force component acting on the shaft 82 that extends at an angle below the axis of pins 70, such as $F_L$, seen in FIG. 8A, the clip 88 will be maintained in a bottomed or latched position against the shell 40. However, if the summation of forces acting on the clip 88 result in a summed force component acting on the shaft 82 that extends at an angle above the axis of pins 70, such as $F_U$, seen in FIG. 8A, the clip 88 will move toward an open or unlatched position, as shown in FIG. 8B.

Thus, where the pulling force of the harness $F_H$ results in a summation force $F_L$ acting on the clip 88, the clip 88 will remain in the latched position. Where a release force $F_R$ is exerted on the clip by the user or other person such that the summation of forces $F_R$ and $F_H$ result in a summation force $F_U$, the clip 88 will move to the unlatched position. Of course, if the angle of the force $F_H$ is altered such that the summation force acting on the clip 88 changes from $F_L$ to $F_U$, the clip 88 will also move from the latched to the unlatched position. For this reason, it is important to design the positioning of the harness with respect to the mask such that the force $F_H$ under normal wearing conditions will not result in a summation force that will unintentionally unlatch the latching mechanism 60. Rather, in a preferred embodiment, under normal conditions, it is intended that the mechanism 60 will unlatch only when an additional release force is applied to the clip 88 by the user or other person. In the unlatched position, each latching mechanism provides 60 slack in the harness of approximately two times the distance between the axes of pins 70 and shaft 82.

Figure 8A:
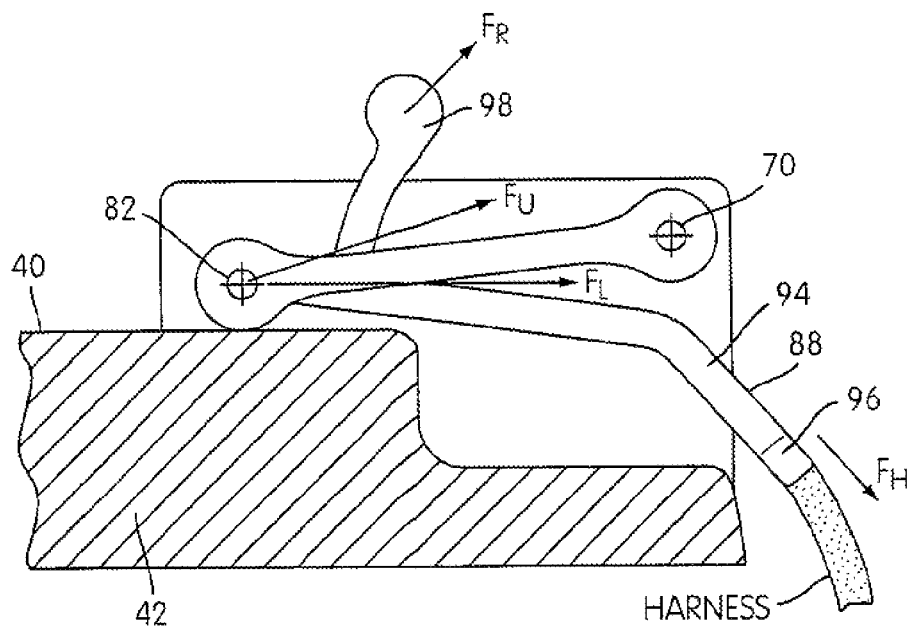
FIGS. 8A-8C are force diagrams showing the forces acting on the latching mechanism of the mask assembly of FIG. 1.
Figure 8B:
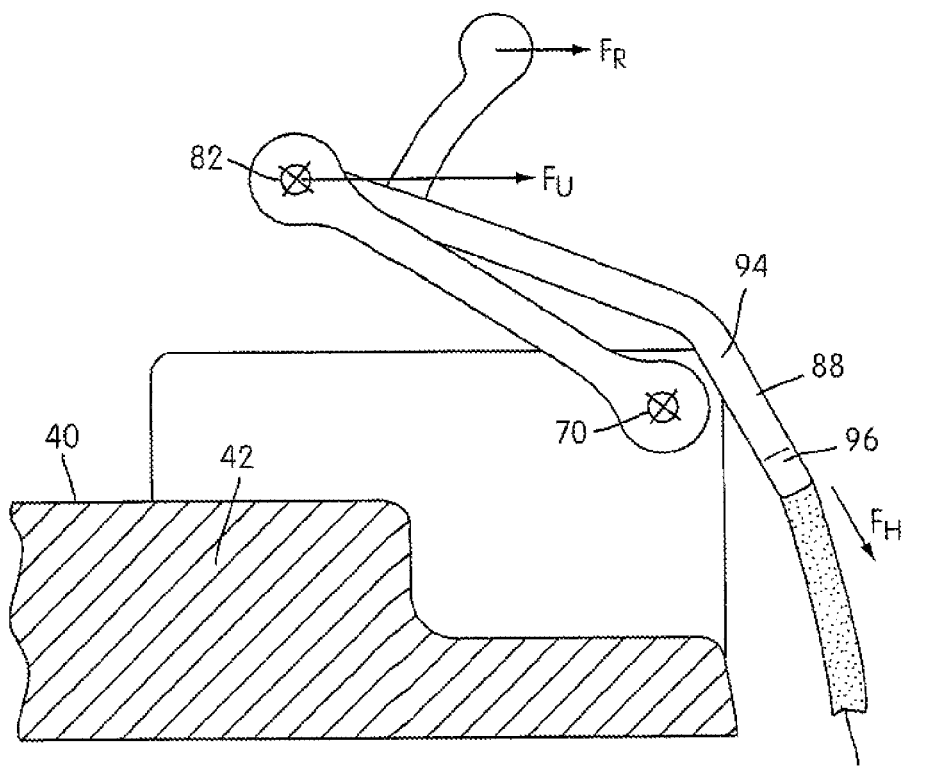
Figure 8C:
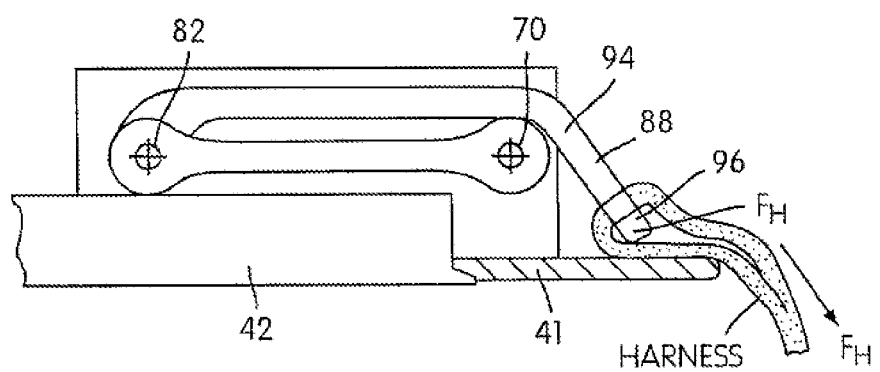

In an alternative embodiment shown in FIG. 8C, the shell 40 includes an extension 41 over which the strap of the harness must pass to prevent the strap from pulling directly downward on the clip 88 and thereby possibly unintentionally providing the necessary force to unlatch the latching mechanism 60. The extensions prevents the strap from applying a pulling force $F_H$ on the clip in an undesired direction.

The use of the quick-release latching mechanism 60 as described above provides for a low-profile attachment mechanism between the shell 40 and the harness, while also allowing the attachment to be quickly, accurately, repeatedly and easily released and latched. The latching mechanism 60 assures that the preset strap adjustment is maintained over repeated latchings and unlatchings. That is, once the strap is adjusted properly for the user, the latching mechanism 60 allows the user to remove and reinstall the mask assembly 10 and maintain the same preset strap adjustment, unlike known mask systems. Further, the slack provided in the harness when each latching mechanism 60 is unlatched also makes it easier for the user to place the mask assembly 10 on the head and to remove it from the head. Such a quick-release is not only convenient for the user, but also provides a level of comfort to the user that the mask can be quickly and readily removed should the user experience any discomfort or sensation of suffocation while wearing the mask. If desired, the design of the latching mechanisms may also be configured to permit the latching mechanisms 60, and thus the straps, to be quickly removed from the shell by placing the latching mechanism 60 in the unlatched position and removing the pins 70 from the bore 50.

Shell

Figure 9A:
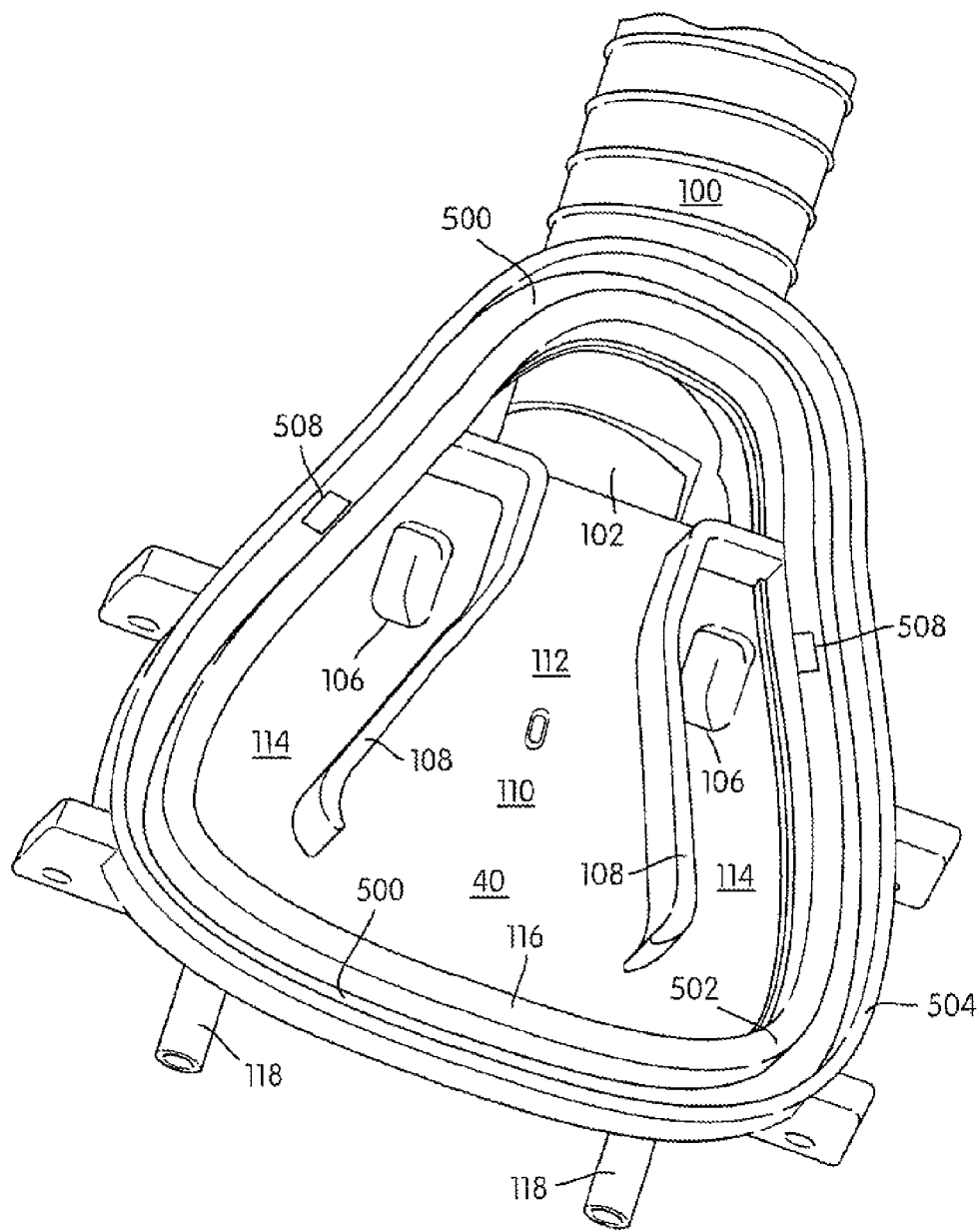
FIG. 9A shows a rear perspective view of the shell of FIG. 2.

The shell 40 may also includes a number of other features. For example, the shell 40 may include an air inlet tube 100 connected to an upper central portion of the shell 40 and having a port 102 opening to an interior of the mask assembly 10 at an upper central position on the shell 40 to supply breathable gas from a pressurized supply to an interior of the mask assembly 10. See FIGS. 1, 2 and 9. The air inlet tube 100 may include an external thread 101 for connecting the air inlet tube 100 to further components of the air supply path. The shell 40 may also include a pair of exhalation ducts 104 positioned on respective sides of the air inlet tube 100 for exhausting gases from the mask assembly 10. Each exhalation duct 104 includes a port 106 opening to an interior of the mask assembly 10 at a position toward the respective side of the shell 40. As is best seen in FIG. 9A, the air inlet tube opening port 102 is separated from the exhalation duct opening ports 106 by a pair of raised walls 108 extending from an interior surface 110 of the shell 40. The raised walls 108 extend from a position adjacent the air inlet tube opening port 102 downward along the shell 40 while angled outward as they extend downward to provide clearance for the user's nose. The raised walls 108 stop before reaching a bottom edge 116 of the shell 40. The raised walls 108 define a central gas intake channel 112 in the mask through which the pressurized gas can flow to the user's nostrils. The raised walls 108 also define a pair of lateral gas exhaust channels 114 within the mask but outside of the central gas intake channel through which exhalation gases can flow to the exhalation ducts 104.

The raised walls 108 improve air flow in the mask by separating the intake gas from the exhalation gas in the mask to help reduce the short-circuiting of oxygen-rich intake gas to the exterior of the mask through the exhalation ducts. The positioning of the exhalation duct opening ports 106 to the outside of the central air inlet tube opening port 102 with the raised walls 108 positioned therebetween utilizes the natural flow of gas in the mask. That is, when the user is inhaling, the gas can flow through the central channel to the user's nostrils. However, when the user exhales, the exhaled gas will flow from the nostrils downward, hitting the bottom edge of the shell and moving outward along the bottom edge of the shell and into the pair of lateral gas exhaust channels. Thus, the flow management provided by the raised walls 108 not only reduces short-circuiting of the intake air to the exhalation ducts 104, it reduces carbon dioxide levels in the mask and also assists in moving the exhalation gas from the user's nostrils to the exhalation ducts 104 while minimizing exhalation backwash into the intake charge.

Figure 9B:
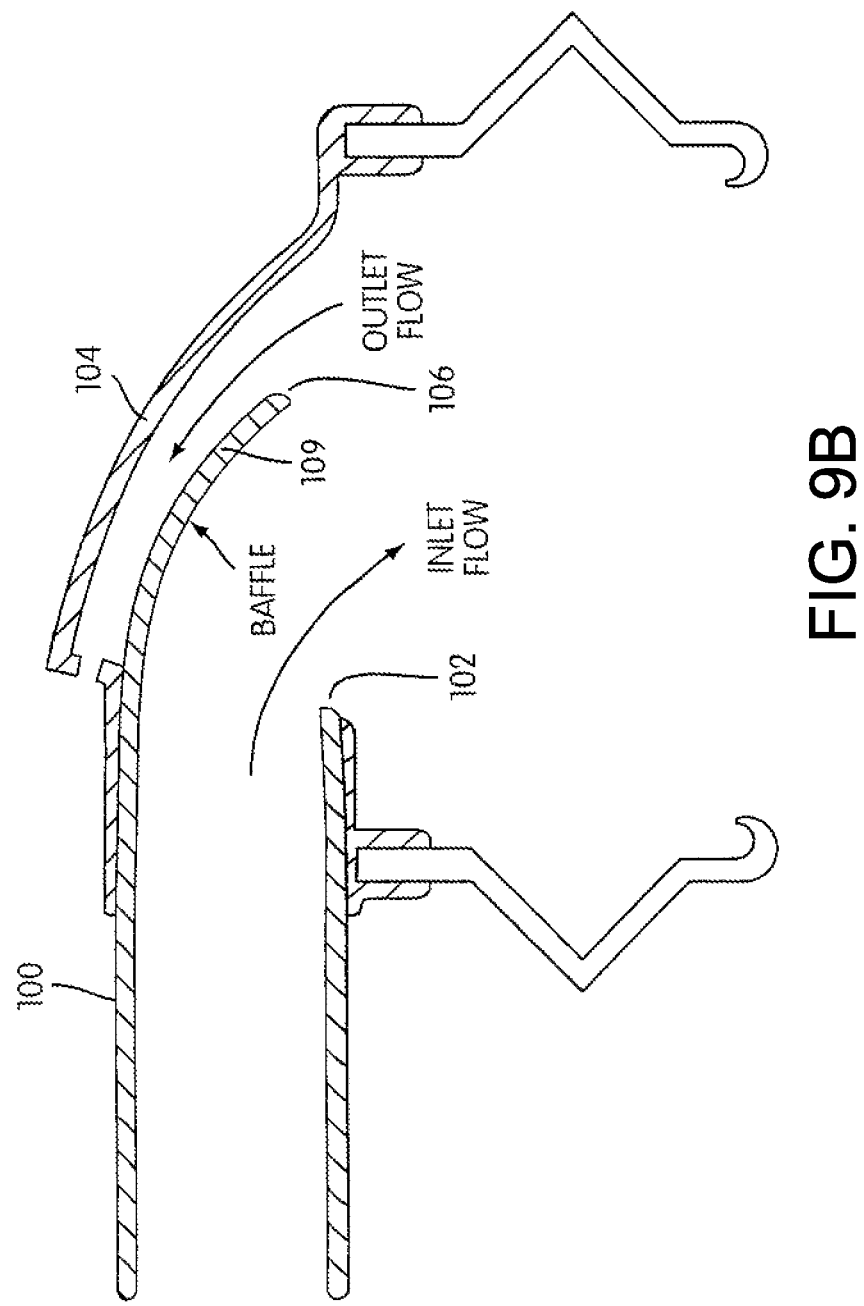
FIG. 9B shows a sectional view of an alternative embodiment of the shell of FIG. 2.

Alternatively, as shown in FIG. 9B, the shell 40 may be provided with a single centrally positioned exhalation duct 104 having a port 106 positioned beneath the air inlet tube opening port 102 and separated by a central baffle 109.

The exhalation ducts 104 may be curved upward and have exhaust ports 120 facing upward with respect to the shell 40 alongside the air inlet tube 100. In this way, the exhalation ducts 104 receive the exhalation gas from the interior of the mask and channel such gas out of the exhaust ports 120, upward alongside the air inlet tube 100. The channeling of the exhalation gases to the exterior of the mask in this manner provides an exhaust flow that follows the air inlet tube upward. This minimizes exhaust flow either toward the mask user's face or toward a bed partner of the user, as can happen with conventional masks that exhaust gas from the front of the mask and which can be disturbing to bed partners when the user is facing the bed partner. Also, locating the exhaust ports farther from the user's nostrils helps reduce breathing noise that escapes from the mask.

The curving of the exhalation ducts 104 upward such that the exhaust ports are remote from the base of the shell can allow greater ease in configuring the cross-section of the exhaust ports for enhanced sound reduction and the accommodation of exhalation diffusers within the mask.

The shell 40 may also include a pair of access ports 118 located at a bottom of the mask 10. The access ports 118 are connectable to one or more supply tubes through which medication or oxygen can be supplied to an interior of the mask. The access ports 118 may also be used to access an interior of the mask 10 for control or measurement purposes, such as to measure a mask interior pressure, $CO_2$ levels, etc. While two such ports are shown, the number of access ports can be altered as is desired. When not in use, the access ports 118 can be capped to prevent leaks from the interior of the mask. The access ports 118 may also be positioned at an upper portion of the shell so that the supply tubes can run alongside the air inlet tube 100 and minimize tangling of the tubes or can be positioned elsewhere on the mask assembly 10 as desired.

Overall Assembly

Figure 10:
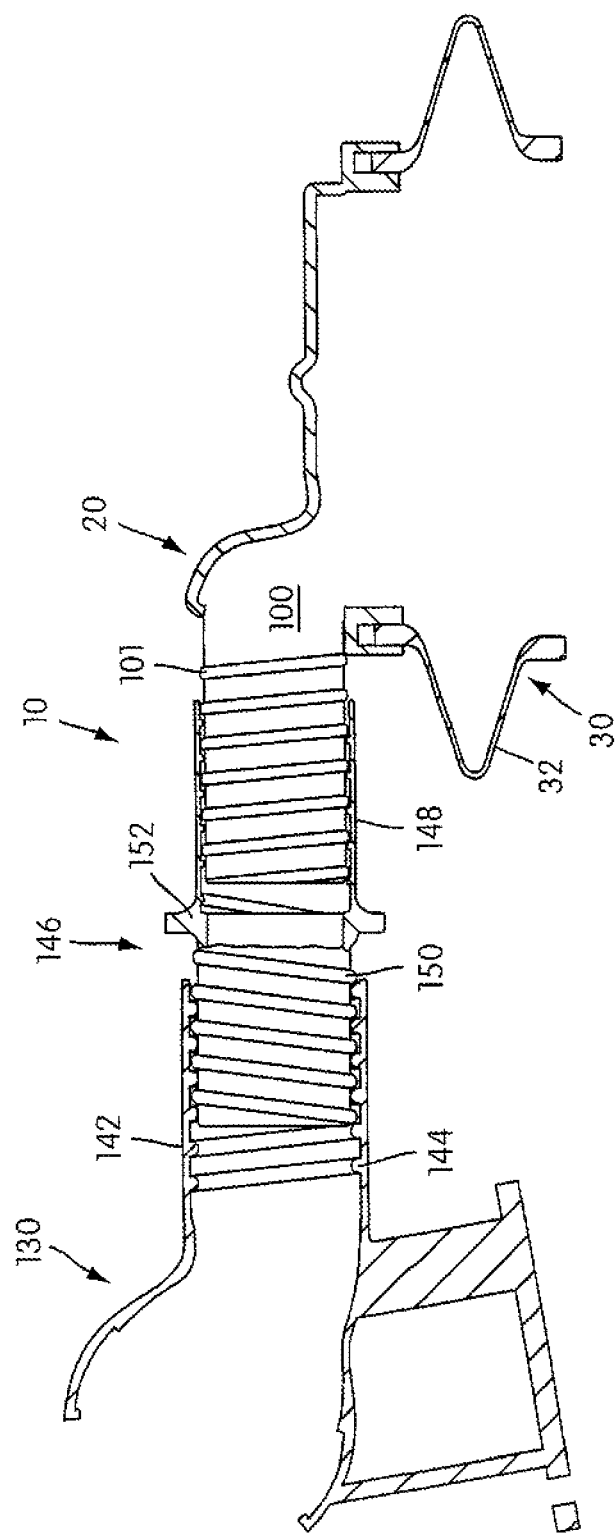
FIG. 10 shows a partial cut away side elevational view of a mask assembly of the present invention.
Figure 11:
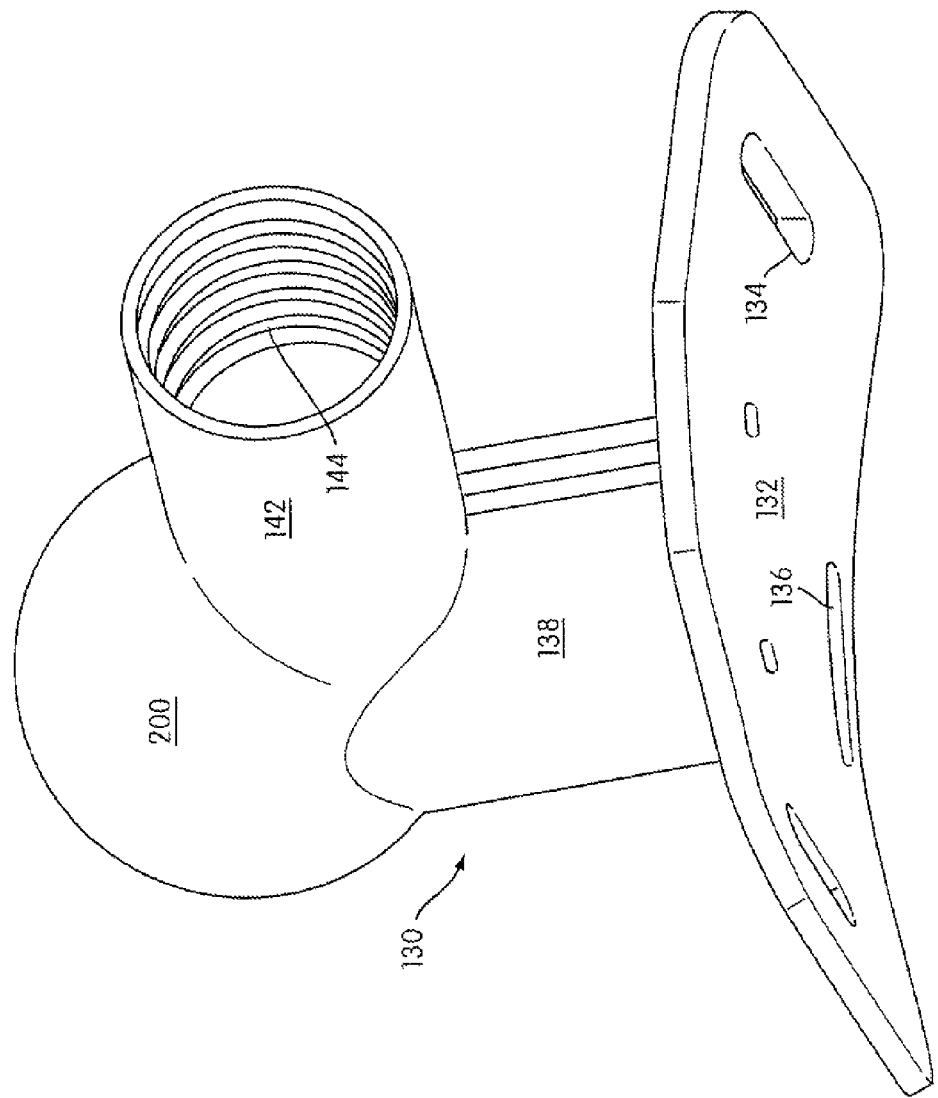
FIG. 11 shows a bottom rear perspective view of a portion of a head mount of the mask assembly of FIG. 10.

FIG. 10 shows a partial cutaway side elevational view of an overall mask assembly 10. In addition to the shell assembly 20 and the cushion 30 (of which only a portion is shown), the mask assembly 10 also includes a head mount 130 and head mount height adjuster 146. The head mount 130 and adjuster 146 provide a connection between an air supply tube 100 and the mask assembly 10. As shown in FIG. 11, the head mount 130 includes a base portion 132 for contacting the user's forehead. The base portion 132 is curved to conform generally to the shape of a user's forehead. A foam or other soft layer may be provided on an underside surface of the base portion 132 to increase the comfort of the user when wearing the mask assembly 10. The base portion 132 also includes three slots 134 and 136 for connecting the head mount 130 to the harness to secure the head mount 130 to the user's head. The two laterally positioned slots 134 mount to portions of the harness extending from around the sides of the user's head, while the centrally positioned slot 136 mounts to a portion of the harness extending from the top of the user's head. Other types of connectors may also be used to connect the head mount 130 to the harness, such as snap connections, hook connections, Velcro®. connections or other connections.

The head mount 130 further includes a pedestal 138 mounted to the base portion 132. The pedestal 138 supports a ball and socket joint socket joint 200 flowingly connected to an air connector tube 142. The ball and socket joint will be described in detail below. The air connector tube 142 includes a thread 144 for connecting to the height adjuster 146. The head mount height adjuster 146 is generally configured as a hollow tube to permit air flow from the head mount 130 to the air inlet tube 100. Head mount adjuster 146 includes a first threaded portion 148 for connecting to the threaded portion 101 of air inlet tube 100 and a second threaded portion 150 for connecting to the threaded portion 144 of air connector tube 142. The height adjuster 146 also includes a centrally mounted finger wheel 152 for rotating the adjuster 146 to adjust the spacing between the head mount 130 and the shell assembly 20.

In a preferred embodiment, one of threaded portions 148 and 150 is right-hand threaded and the other is left-hand threaded, as are the respective corresponding threaded portions of the air inlet tube 100 and the air connector tube 142, so that the distance between the head mount 130 and the shell assembly 20 can be altered by rotating the adjuster 146 only, and without rotating either the head mount 130 or the shell assembly. See FIG. 10. This feature makes it easy for the user to adjust the spacing between the head mount 130 and the shell assembly 20 for the best fit and comfort once the mask assembly 10 has been placed on the user's head without the need for removing the mask assembly to rotate either the head mount 130 or the shell assembly 20 with respect to one another as would be necessary if all of the threaded portions were right-handed or left-handed.

Although not preferred, the threaded portions may be made all right-handed or left-handed. Further, the internal and external threaded portions of the respective mating components may be reversed. It is preferred that the threaded connections between the air inlet tube 100, the height adjuster 146 and the air connector tube 142 be of a sufficiently close tolerance such that any substantive air leaks at the joints may be prevented. Further, adjustment will remain as set under normal wearing conditions, and the tolerances are not so tight as to prevent ready rotation of the adjuster 146 with only the user's fingers when the user desires to alter the adjustment.

In the preferred embodiment of the present invention, the shell 40 is made of polycarbonate, the latching mechanism 60 components may be made of a semi-rigid plastics material such as acetal or nylon, and the head mount 130 may be made of acetal or polypropylene. The various components can also be made of other known materials.

Ball and Socket

Figure 12:
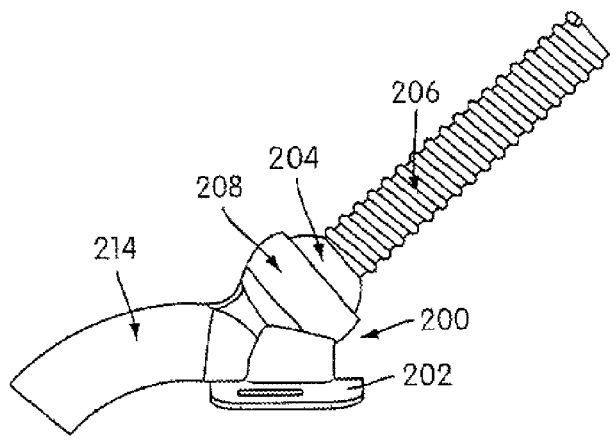
FIGS. 12-16 show a ball and socket joint of the present invention with FIG. 15 being a detail of FIG. 14.
Figure 13:
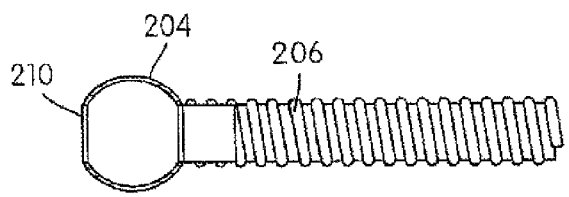
Figure 14:
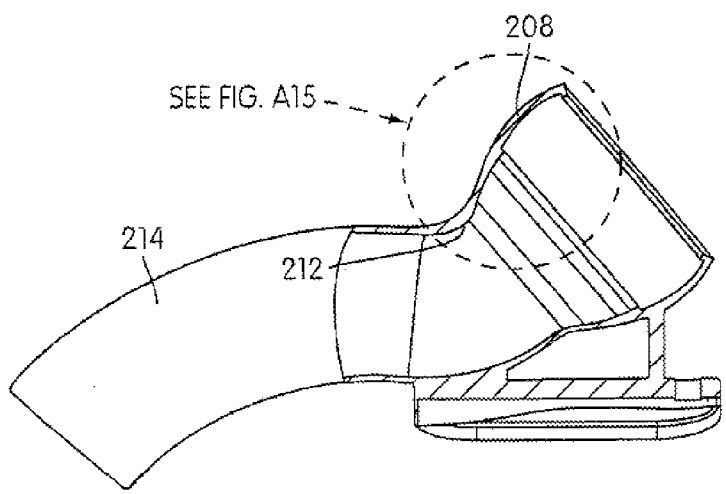
Figure 15:
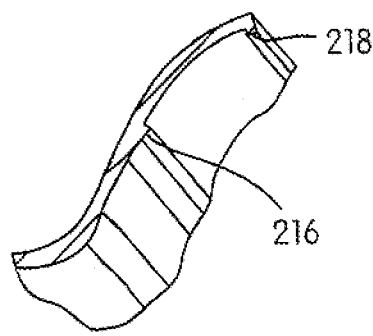
Figure 16:
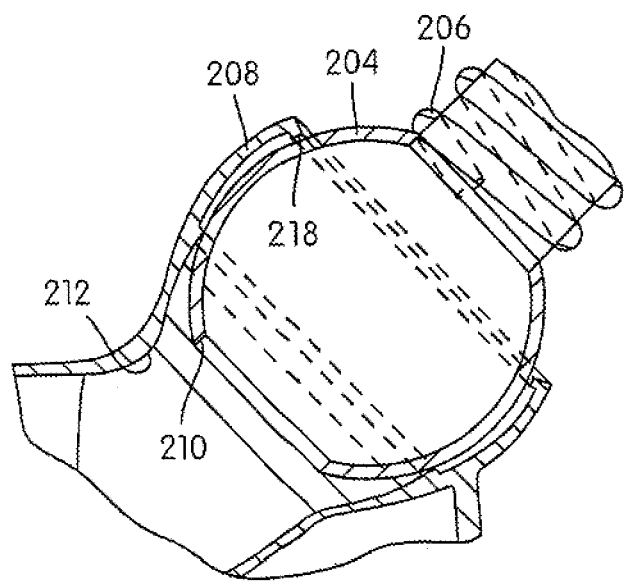
Figure 59:
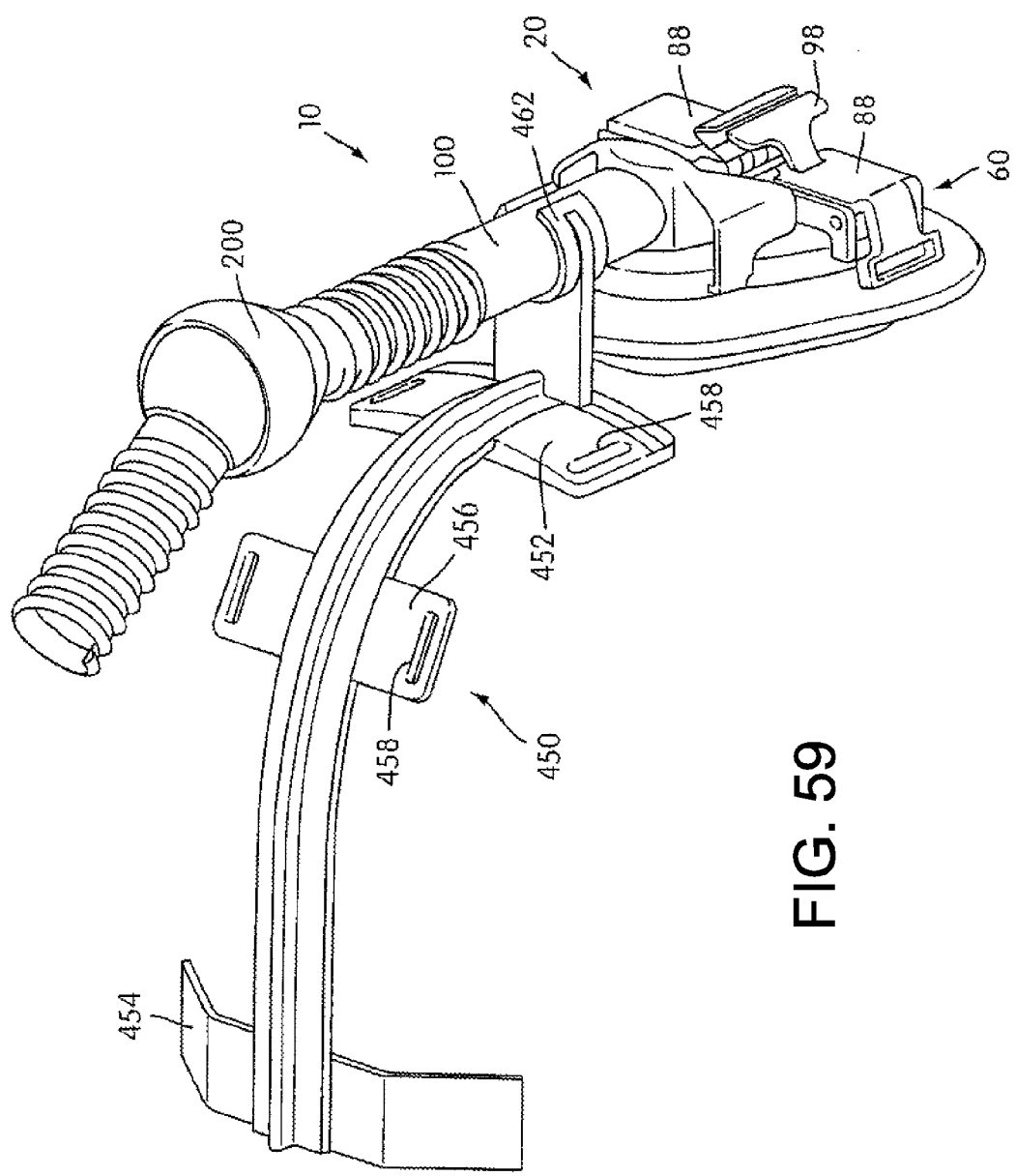
FIG. 59 shows a perspective view of an alternative embodiment of the mask assembly of the present invention.
Figure 60:
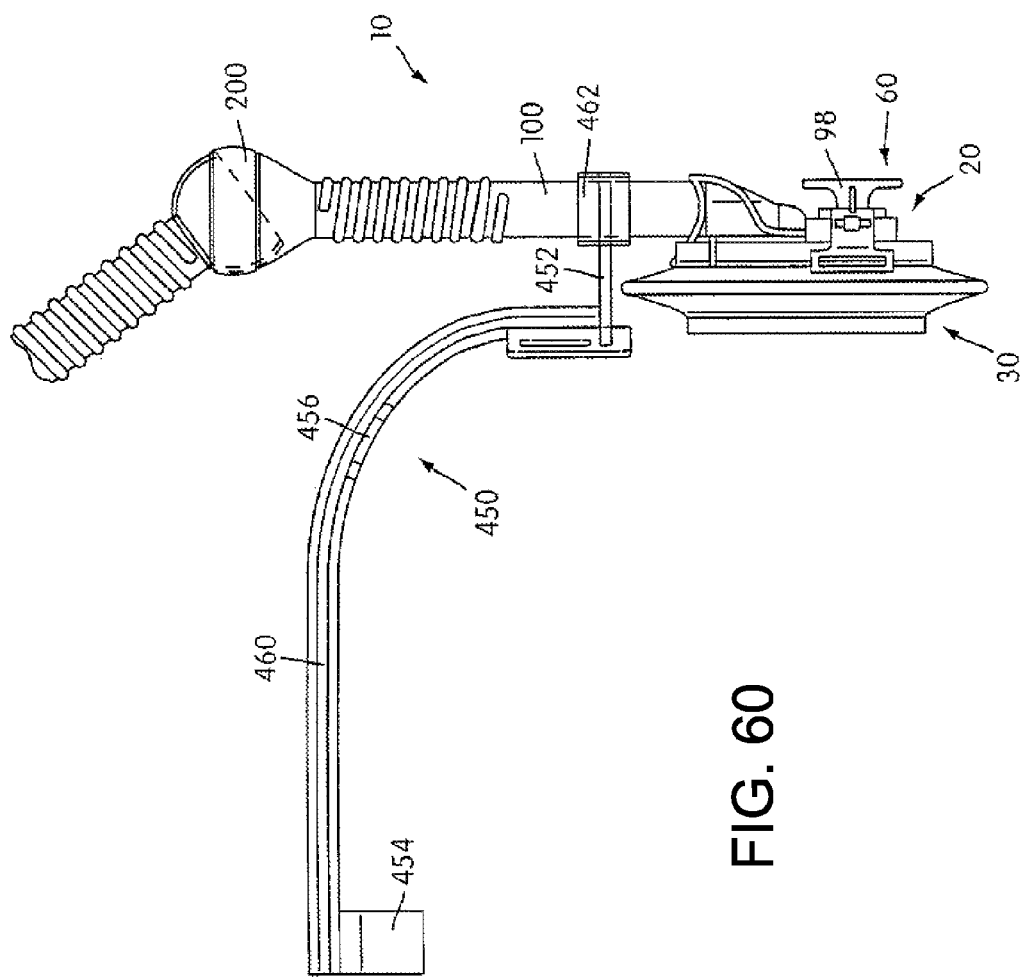
FIG. 60 shows a side elevational view of the mask assembly of FIG. 59.
Figure 61:
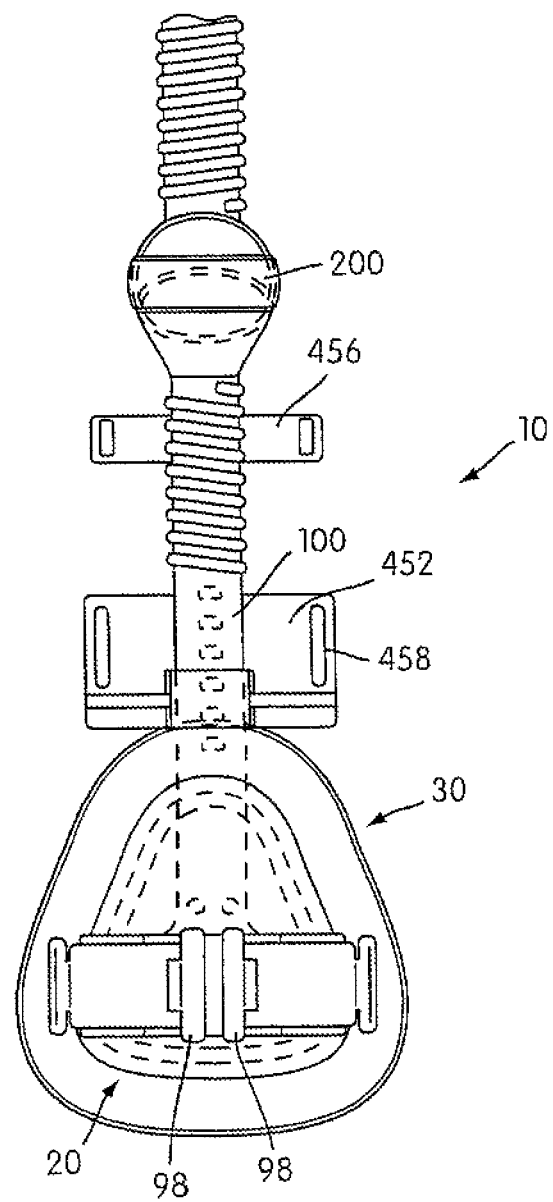
FIG. 61 shows a front elevational view of the mask assembly of FIG. 59.

Existing swivel and elbow arrangements for the air connections between a pressurized air source and the mask can have detractions such as leakage and squeaks around the elbow. In another embodiment of the present invention, 200 these shortcomings may be overcome with a mask assembly 10 having a novel ball and socket joint 200 for the breathable air inlet connection to the mask 10. The ball and socket joint 20 may also augment the advantages of an embodiment of the present invention incorporating a gusset portion by providing additional flexibility between the air supply tube and the mask. The ball and socket joint 200 is shown in detail in FIGS. 12-16. In the embodiment shown in FIGS. 12-16, the ball and socket joint 200 is mounted closer to a base plate 202 and includes a curved air connector tube 214. The details of the joint 200 are applicable to the embodiment of FIGS. 10 and 11. FIG. 12 shows a ball and socket joint 200 attached to a base plate 202 that can be attached to the patient's forehead with the harness/headgear. Alternatively, the ball and socket joint 200 may be mounted directly to the mask shell 40 or can be attached only to an air supply tube connected to the air inlet tube 100 of the shell 40. In this latter embodiment, shown for instance, in FIGS. 59-60, the ball and socket joint 200 can freely move, as it is not rigidly attached to the shell 40 or some other stationary structure. The joint 200 includes a ball 204 mounted on the end of flexible air tube 206. The air tube 206 maybe adapted for connection with a pressurized air source. The ball 204 is adapted for mounting in a socket 208. Pressurized air from the air tube 206 flows through an orifice 210 in the ball 204 into the socket 208 and through an orifice 212 in the socket 208 to the mask 10 through tube 214. The socket 208 includes an inner circumferential seat 216 and a lip 218 at an outer edge of the socket 208. The ball 204 can be relatively easily inserted into the socket 208 and removed, if necessary. Once the ball 204 is inserted into the socket 208, it rests between the seat 216 and the lip 218 with a small clearance provided between the ball 204 and the seat 216 and lip 218 of the socket.

Conventional ball and socket joints typically have very tight tolerances to avoid air leaks but this can cause heavy friction in the movement of the ball and thus negate any mobility and flexibility advantage that might be desired. However, the small clearance provided between the ball 204 and the seat 216 and lip 218 of the socket 208 allows the ball 204 to move or rotate freely with respect to the socket 208. While the ball 204 is in motion, the clearance allows a small amount of the pressurized air to escape between the ball 204 and socket 208 to the atmosphere. However, once the ball 204 is in a static position, the air pressure forces the ball 204 against the lip 218 and seals the connection between the ball 204 and socket 208 until the ball 204 is again placed in motion. See FIG. 16. The ball and socket joint 200 allows the air supply tube to be moved about the socket 208 anywhere in a range of movement in the form of a cone projecting from the socket and provides increased movement of the air tube over a conventional elbow swivel joint.

In testing, the ball and socket joint of the present invention was found to leak at a rate of less than 1 ltr/min at pressures between 2 and 20 cm of water. The ball and socket joint 200 may be formed by methods and materials well known in the art, such as, for example, polypropylene. This material has the advantage of having a soft wax-like surface texture, which helps reduce noise between the part s during movement. The ball can also preferably be made of polycarbonate. The ball and socket joint 200 may, like the remainder of the invention, be manufactured of any of the materials known to be used for the production of such joints or mask parts, although it is preferred that one of the ball and socket be made from a relatively rigid material and the other made from a relatively flexible material for best operation.

Figure 17:
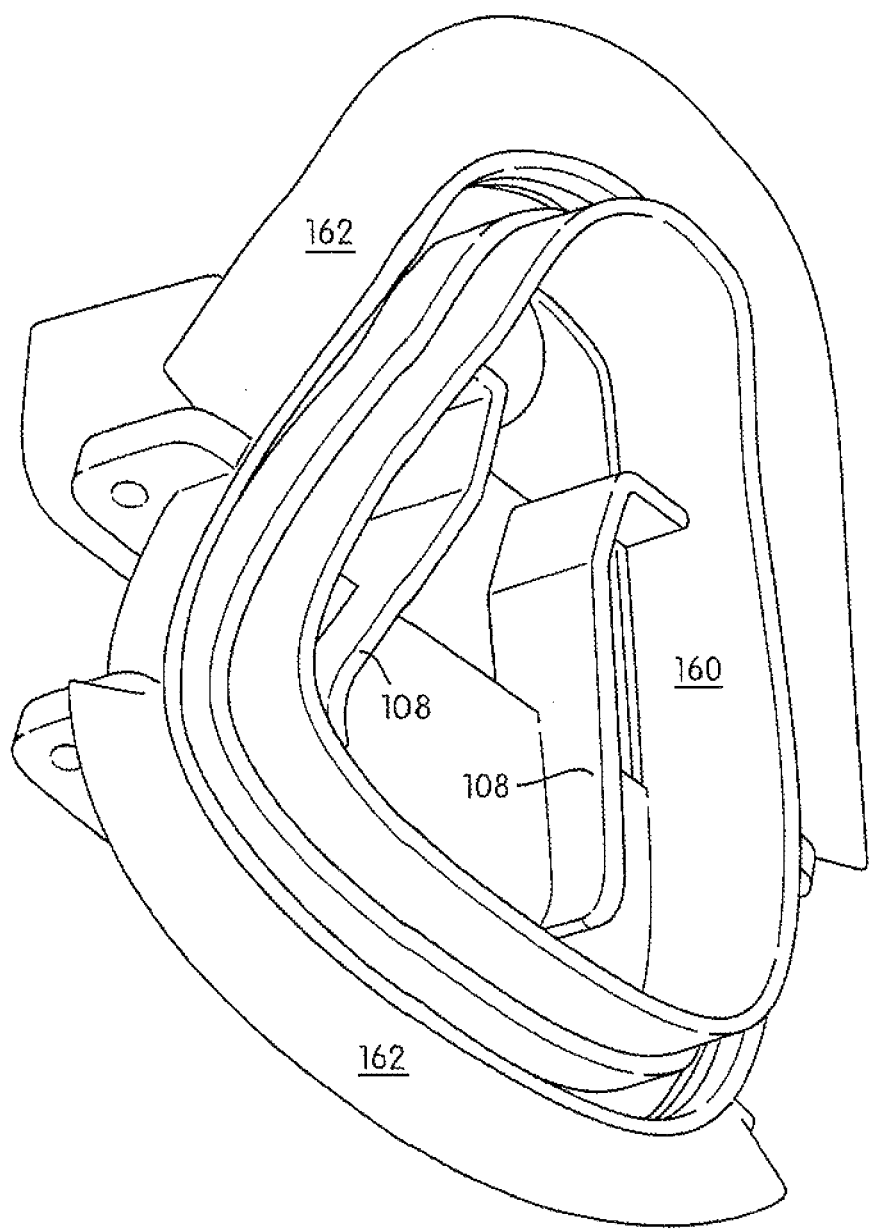
FIG. 17 shows a rear perspective view of an alternative embodiment of the shell of the present invention.
Figure 18:
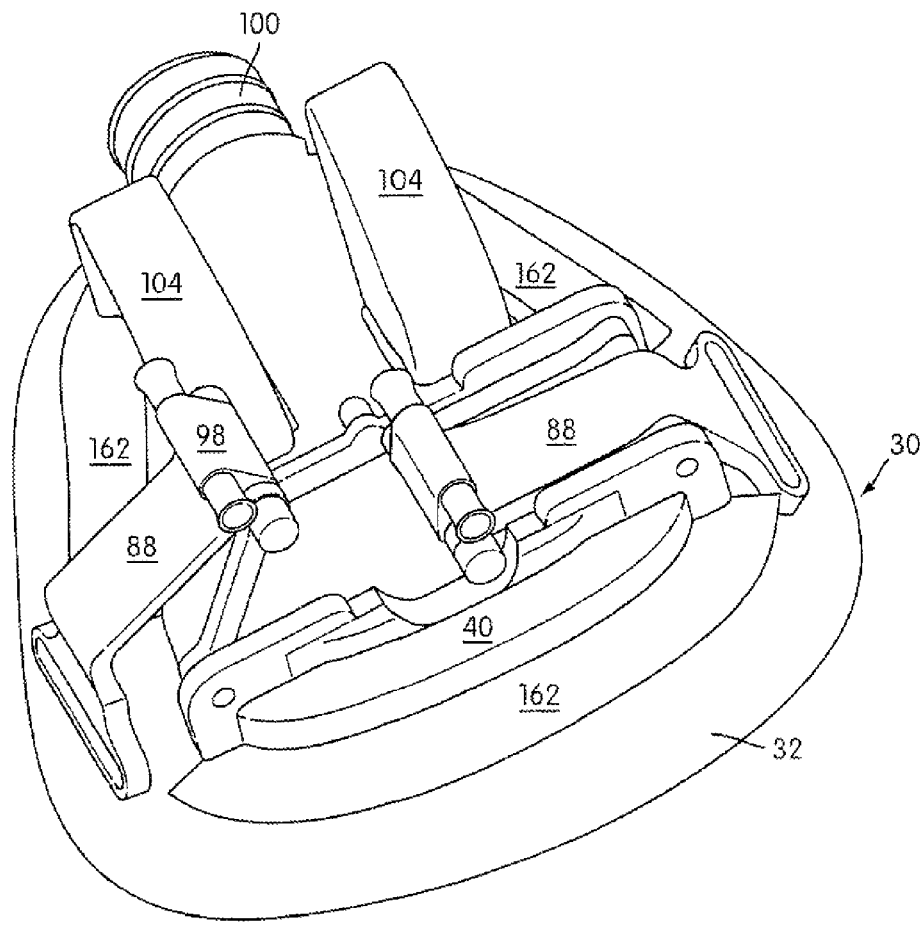
FIG. 18 shows a front perspective view of an alternative embodiment of the shell of FIG. 17 and an alternative embodiment of the latching mechanism of the present invention.

An alternative embodiment of the shell 40 is shown in FIGS. 17 and 18. In this embodiment, an internal wall 160 of the shell 20 has been given an increased height such that this internal wall 160 will project into the cushion 30. This embodiment is especially designed for use with a gusseted cushion, as discussed above and shown in FIGS. 1 and 10. The internal wall 160 is configured so as to project into the gusset portion 32 of the cushion without actually contacting the interior of the gusset portion 32 so as not to interfere with pressurization and movement of the gusset portion 32 of the cushion 30. This projection into the gusset portion 32 helps maintain alignment of the cushion 30 with the shell 40 when the gusset is in a deflated or closed state. The projection need not be continuous around the periphery to provide effective alignment and can include separate independent projecting portions to achieve the same result.

The embodiment of FIGS. 17 and 18 also includes a flange 162 extending around a periphery of the shell 40. This flange 162 contacts a front side of the gusset portion 32 of cushion 30 when the mask is in use and effectively stiffens the gusset portion 32 of the cushion 30 to provide more force on the face from the cushion. This feature is further described in U.S. patent application Ser. No. 09/885,445, "Mask with Gusset" to Frater et al. filed on Jun. 21, 2001, now U.S. Pat. No. 6,986,352 discussed above. The shell 40 in this embodiment is also provided with exhalation ducts 104 of an increased size. The air inlet tube 100 is also shortened in this embodiment as compared to the embodiment of FIG. 2.

ALTERNATIVE EMBODIMENTS

Figure 19:
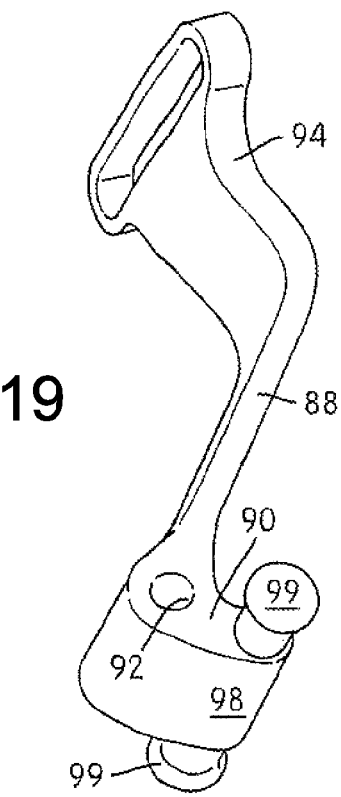
FIG. 19 shows a perspective view of a clip of the latching mechanism of FIG. 18.

In addition, an alternative embodiment of the clip 88 is shown in FIGS. 18 and 19. In this embodiment, the flip arm 98 is positioned generally directly over the bore 92, instead of intermediate bore 92 and end 94 as in the embodiment shown in FIG. 7. With such a placement of the flip arms 98, when the latching mechanisms 60 are in the closed state, the flips arms 98 are closely adjacent one another. This allows both flip arms 98 to be grasped simultaneously between the thumbs and forefingers of the user when in the closed position and moved to a position where the latching mechanisms 60 will both unlatch and open. Each flip arm 98 also has a lower height to reduce the chance that the flip arm 98 will become entangled in the bed linens and unintentionally unlatch the latching mechanism upon movement of the user or bed linens. In this embodiment, the flip arm is provided with grasping extensions 99 on both sides. The grasping extensions 99 are preferably dished to allow secure grasping of the flip arm 98 between the user's thumb and forefinger. This embodiment clip 88 does not include a stop surface 95 in order to better conform to the flatter upper surface of the shell 40 shown in FIG. 18.

Figure 20:
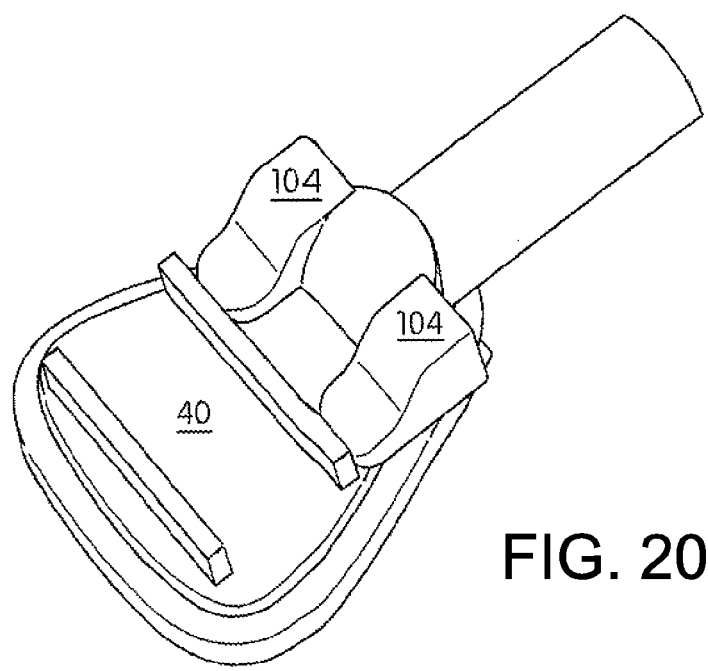
FIG. 20 shows a front perspective view of an alternative embodiment of the shell of the present invention.
Figure 21:
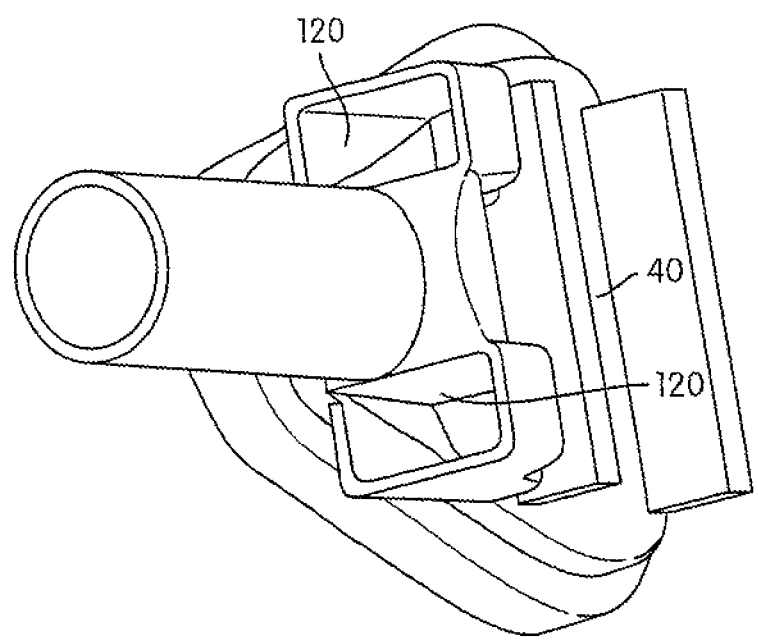
FIG. 21 shows a top perspective view of an alternative embodiment of the shell of the present invention.

An alternative embodiment of the shell 40 is shown in FIGS. 20-21. In this embodiment, the exhalation ducts are further increased in size to increase a cross-sectional area of the exhaust ports 120, reducing exhalation gas velocity and/or providing additional space for an exhalation gas diffuser.

Alternative Mask Assembly

Figure 22:
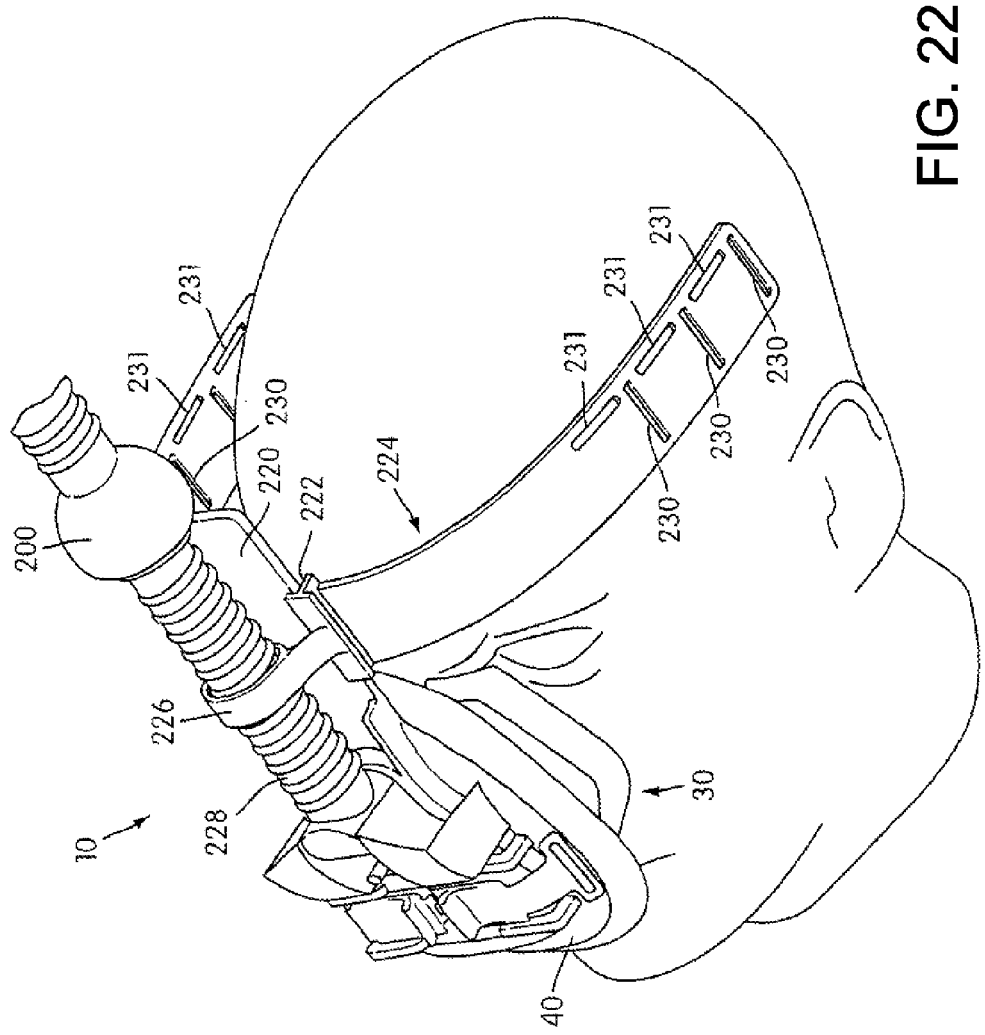
FIG. 22 shows a perspective view of an alternative embodiment of a mask assembly of the present invention installed on a user.
Figure 23:
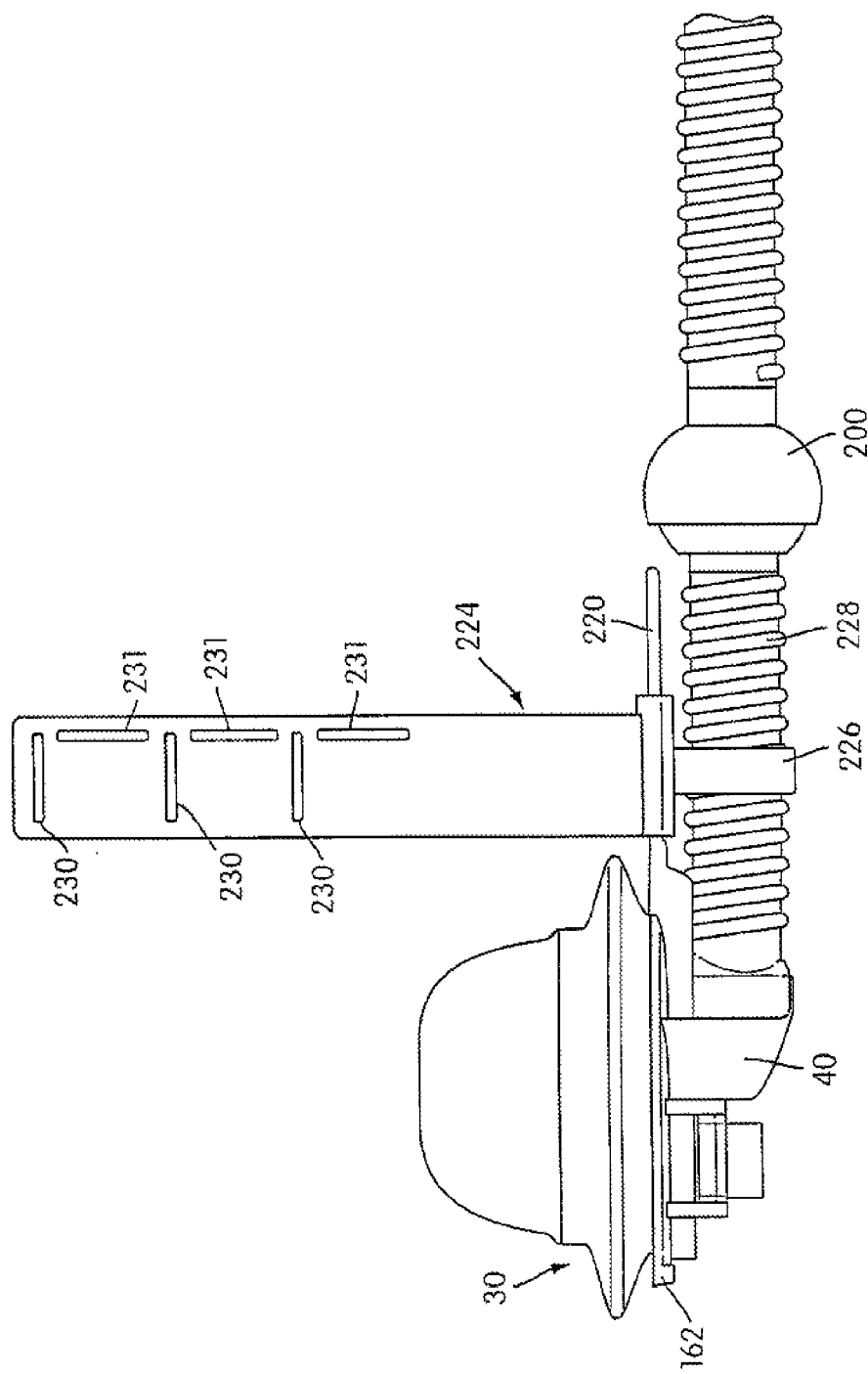
FIG. 23 shows a side elevational view of the mask assembly of FIG. 22.
Figure 24:
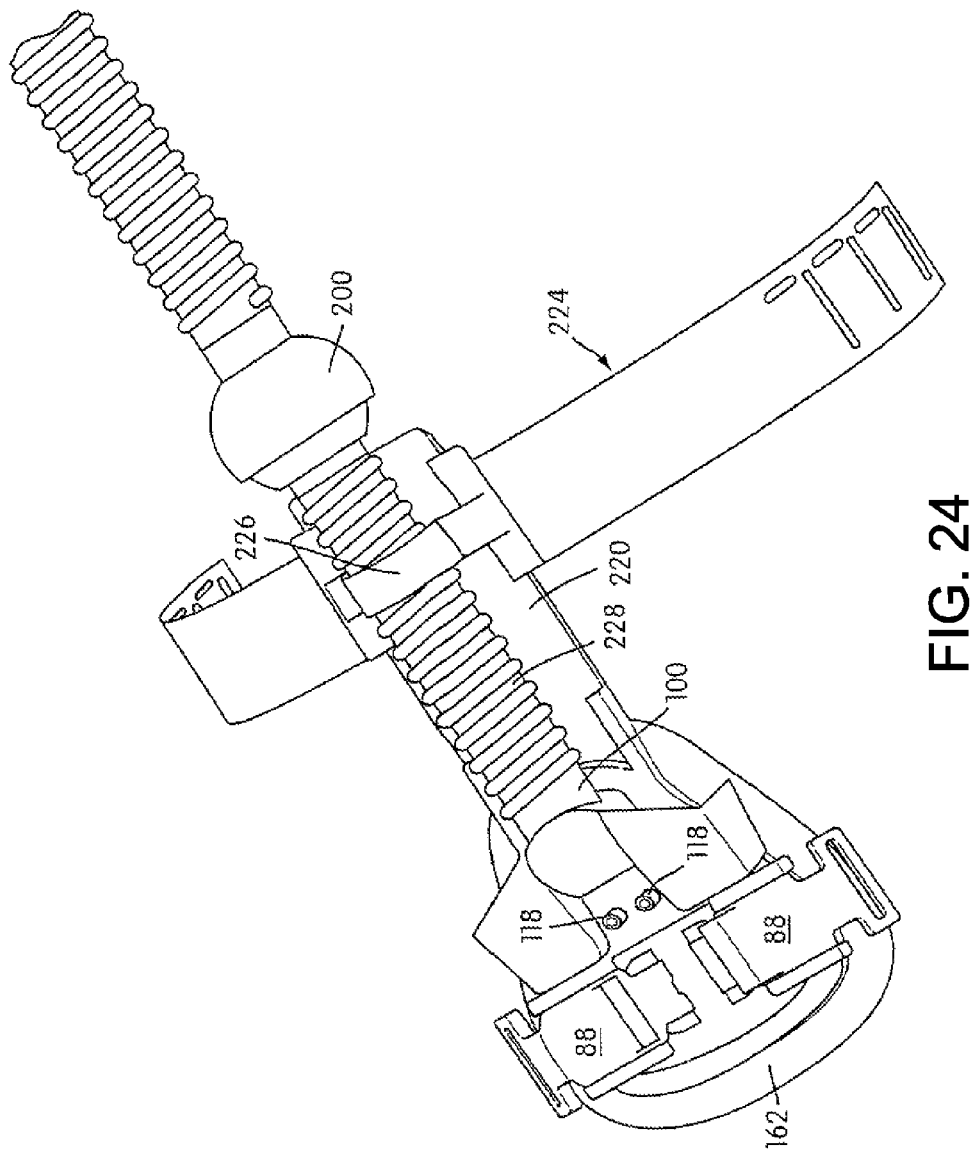
FIG. 24 shows a front perspective view of the mask assembly of FIG. 22.

FIGS. 22-29 show an alternative embodiment of the mask assembly 10. In this embodiment, the mask assembly does not use a separate head mount as the embodiment discussed above. Rather, the shell 40 includes an extension bracket 220 extending from an upper portion of the shell 40. The extension bracket 220 is generally rectangular but may have other configurations as well. The extension bracket 220 is configured to engage a retaining channel 222 of a head strap 224. Because the sides of the extension bracket 220 and the retaining channel 222 are generally parallel, the head strap 224 can be moved up and down the extension bracket 220 to adjust the distance between the head strap 224 and the main body of the shell 40/cushion 30. This allows the head strap 224 to be adjusted to properly fit the user. Compare FIG. 23 and FIG. 24 depict different adjustments that may be made to the head strap 224 along the extension bracket 220.

Figure 25:
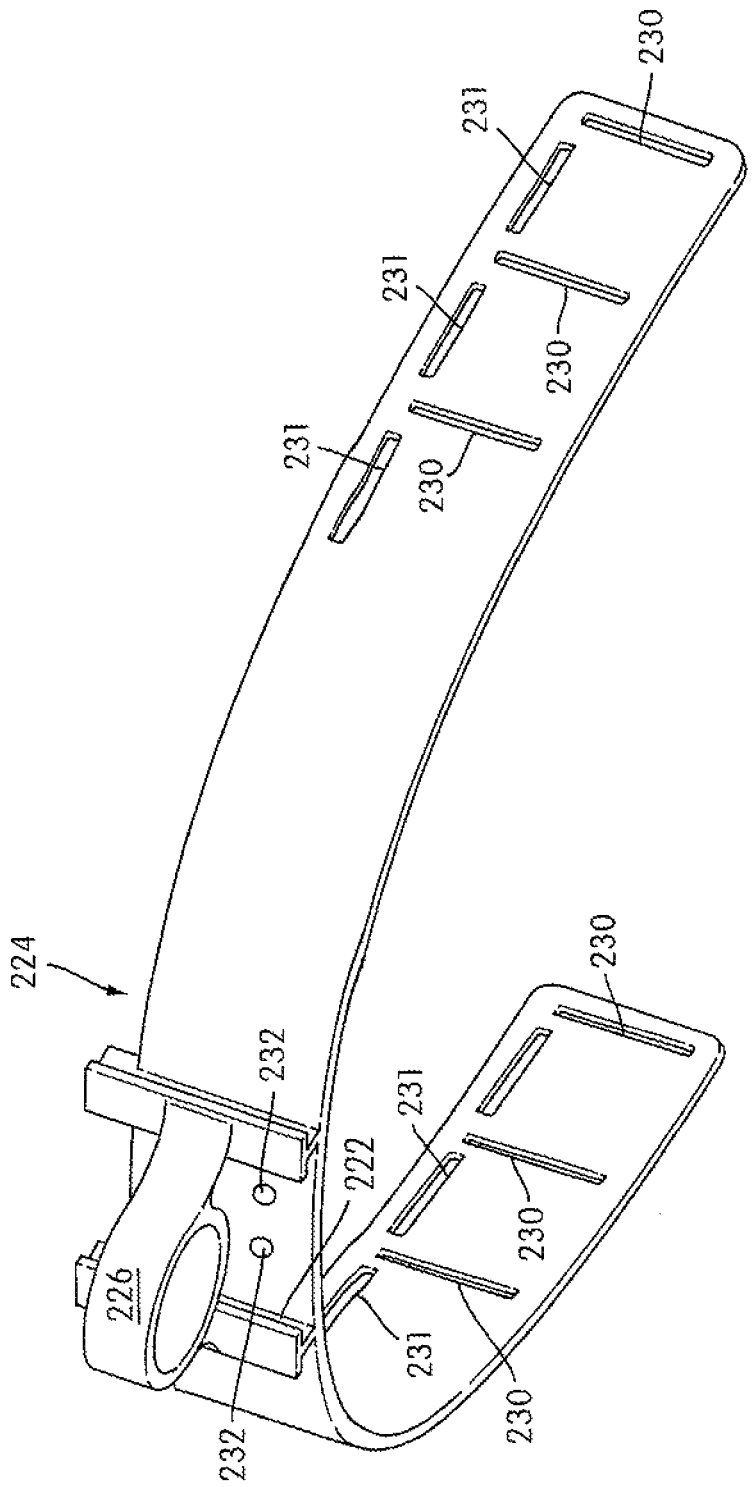
FIG. 25 shows a perspective view of a head strap of the mask assembly of FIG. 22.
Figure 26:
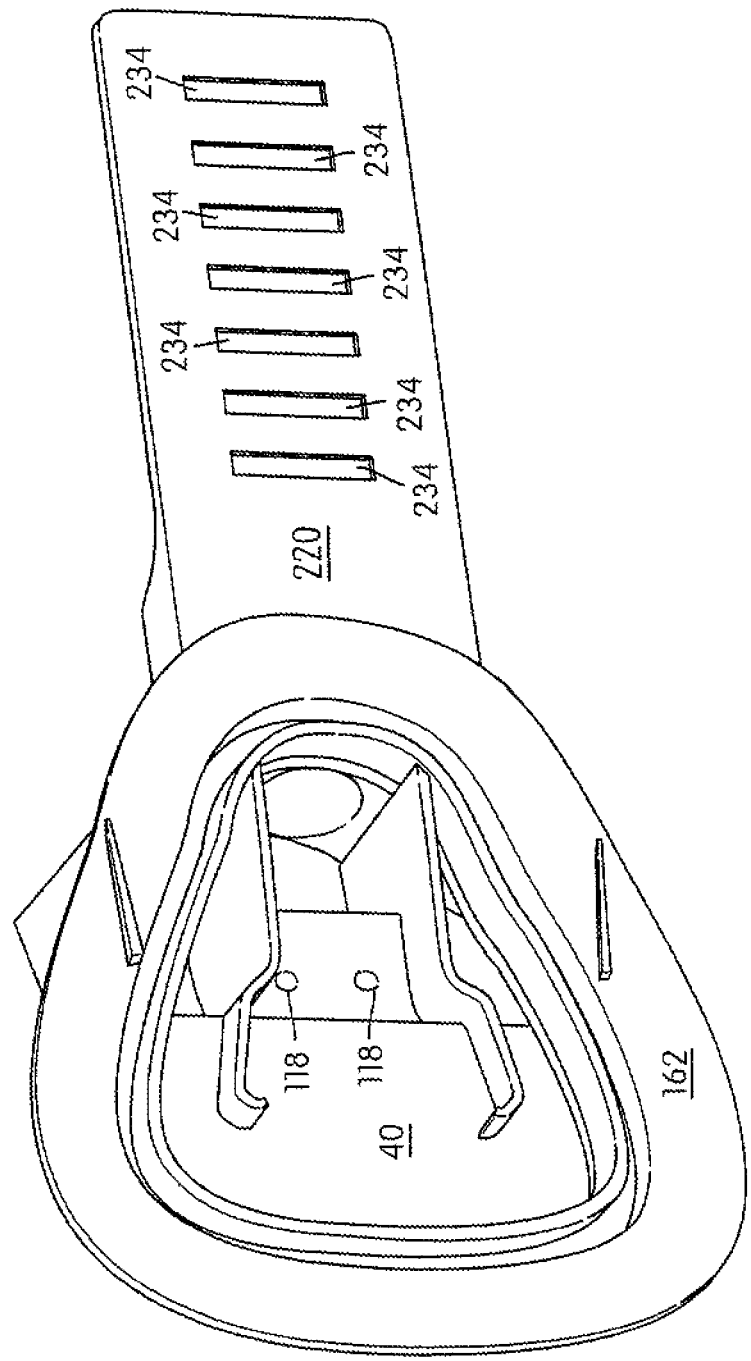
FIG. 26 shows a rear perspective view of a shell of the mask assembly of FIG. 22.

In FIGS. 25 and 26, the head strap 224 also includes a pair of raised projections 232 positioned in the retaining channel 222 adapted to engage any one of a plurality of detent slots 234 positioned along an under side of the extension bracket 220. When the head strap 224 is adjusted along the extension bracket 220 until the projections 232 engage one of the slots 234, the head strap 224 will be maintained in this adjusted position, under normal wearing conditions, until the user re-adjusts the head strap 224 with respect to the extension bracket 220. The height of the projections 232 is established in connection with the flexibility of the head strap 224 such that the projections 232 may be moved from one detent slot 234 to another without requiring undue force to make such an adjustment. In a preferred embodiment, one or both of the edges of the projections 232 and the detention slots 234 may be rounded to ease movement of the projections 232 out of the respective slots 234. Although two generally round projections 232 are shown in FIG. 25, other numbers and configurations of projections may also be used. The head strap 224 also includes a retaining loop 226 mounted above the retaining channel 222. In FIG. 24, the retaining loop 226 is sized to engage and retain a connector tube 228 connecting the air inlet tube 100 with a ball and socket joint 200. In this embodiment, the positioning of the ball and socket joint 200, with respect to the shell 40, is reversed as compared to the embodiments shown above. If desired, the positioning can be as discussed above. The retaining loop 226 thus supports both the connecting tube 228 and the ball and socket joint 200.

In FIG. 25, the head strap 224 includes a plurality of adjustment slots 230 and adjustment slots 231 on both free ends. The adjustment slots 230 are for connecting to side portions of a harness or retaining strap extending between the free ends of the head strap 224 and the adjustment slots 231 are for connecting to top portions of a harness or retaining strap extending between the free ends of the head strap 224 to secure the head strap 224 to the user's head. While the head strap 224 includes the retaining channel 222 on an outside surface thereof, the inner surface of the head strap 224 may be kept generally smooth.

In this embodiment, the head strap 224 does not actually contact the user's forehead but floats in front of the user's forehead. When the gusset portion of the cushion 30 is inflated, the shell 40 is pushed away from the user's face, placing tension on the head strap 224 being held in place by the harness extending between free ends of the head strap 224. This tension pulls the head strap 224 away from the user's forehead. This results in increased comfort for the user, since there is less contact with the user's face and also prevents unsightly pressure marks from occurring on the user's forehead due to contact with the mask assembly 10, as can occur with known mask assemblies.

Figure 27:
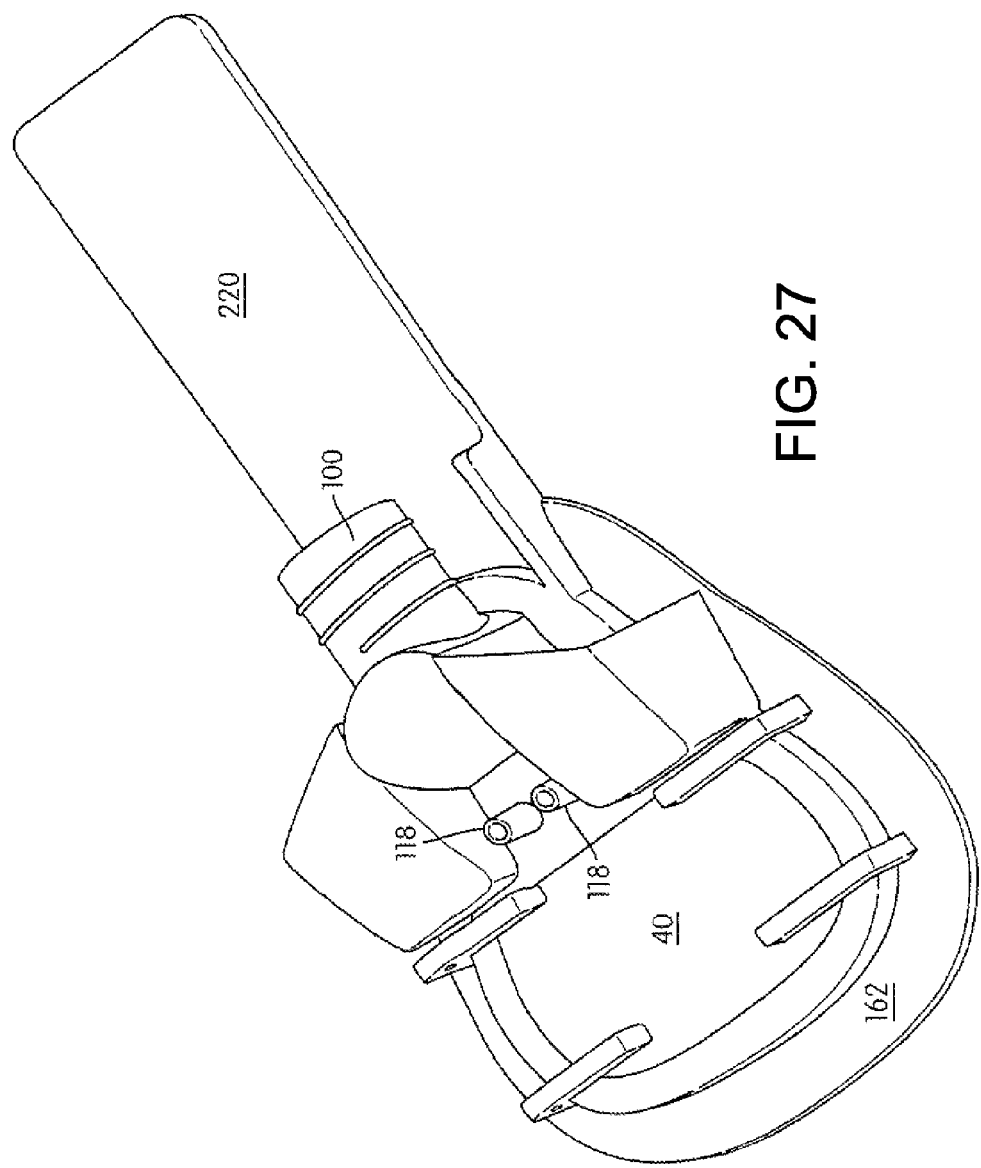
FIG. 27 shows a front perspective view of the shell of FIG. 26.
Figure 28:
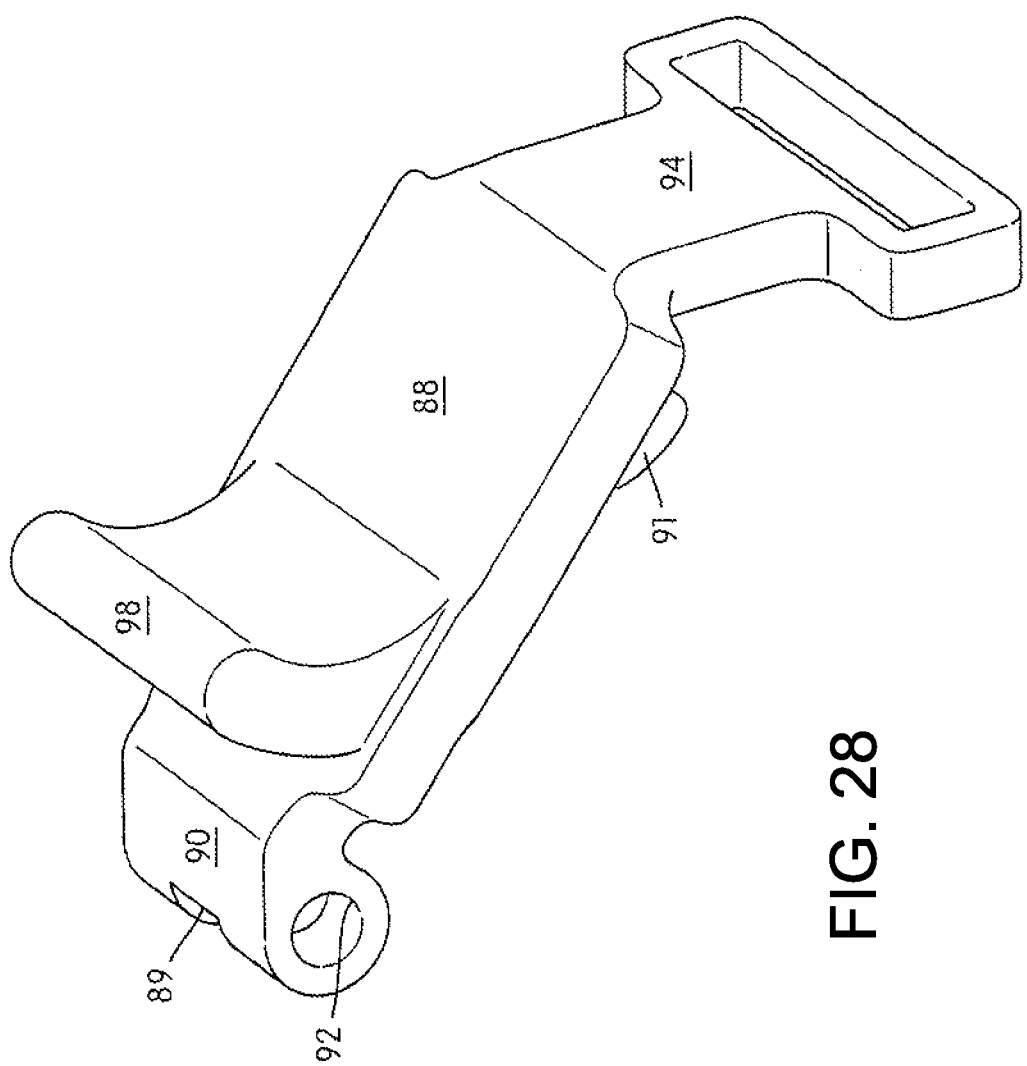
FIG. 28 shows a perspective view of a clip portion of a latching mechanism of the mask assembly of FIG. 22.

In FIG. 26, the access ports 118 are positioned closer together and more centrally on the shell 40 than in the previous embodiments. In FIG. 27, the access ports 118 also extend from a front of the shell 40, as opposed to a bottom of the shell 40. As with the embodiment shown in FIG. 17, the shell 40 in this embodiment also includes a flange 162 extending around its periphery to contact and support the gusset portion of the cushion 30 and stiffen the action of the gusset portion.

Figure 29:
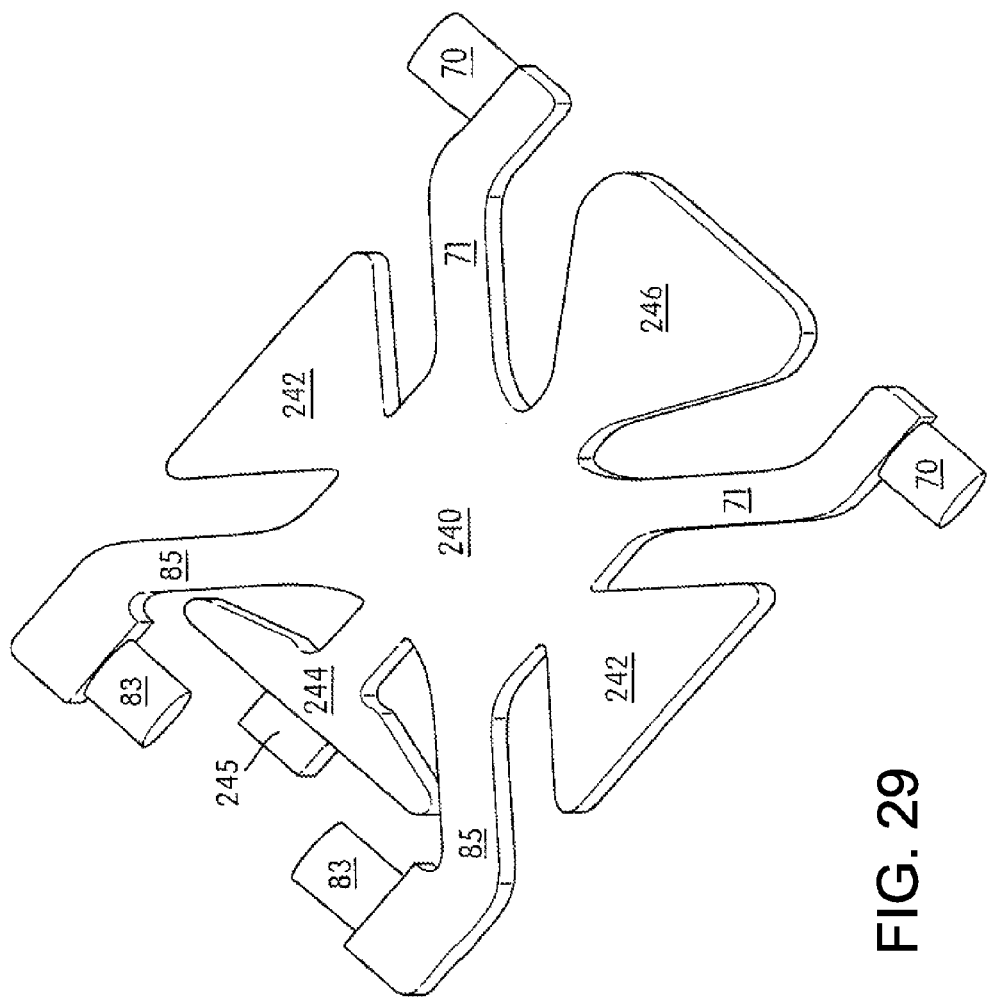
FIG. 29 shows a perspective view of a unitary clip link of the latching mechanism of the mask assembly of FIG. 22.

In FIG. 29, each latching mechanism 60 in this embodiment replaces the two clip links 62, 64 and pin 80 of the embodiment shown in FIGS. 1-7 with a unitary clip link 240. Each latching mechanism 60 also includes a clip 88, similar to the clip shown in FIGS. 1-7 except as described below. See FIG. 28.

The unitary clip link 240, depicted in FIG. 29, includes two pins 70 for engaging bore 50 of the respective flange assembly. The two pins 70 are mounted on pin arms 71 extending freely away from a central portion of the link 240 to provide a spring action so that they can be squeezed toward one another to allow clearance for inserting the pins 70 in the bore 50. Likewise, unitary clip link 240 includes two inwardly facing pins 83 for engaging bore 92 in clip 88. The pins 83 are mounted on pin arms 85 extending away from a central portion of the link 240 to provide a spring action so that they can be flexed outward to provide clearance for inserting the pins in the bore 92. The unitary clip link 240 also includes a pair of centrally positioned side extensions 242. These side extensions 242 engage inner surfaces of the flange assemblies when the latching mechanism 60 is latched to provide lateral stability to the latching mechanism 60.

The unitary clip link 240 also includes a third extension 244 extending between pin arms 85 toward pins 83 and a fourth extension 216 extending between pin arms 71. The third extension 244 includes an extending tab 245 that is adapted to engage a slot 89 on clip 88. The slot 89 is configured such that an end surface of the slot 89 contacts the tab 245 when the latching mechanism 60 has reached full extension in the open position to provide a positive stop to further movement of the latching mechanism 60. The slot 89 can also be configured to provide a positive stop to the tab 245 when the latching mechanism 60 is in the closed position. Extensions 242, 244 and 246 all act to limit excessive movement of adjacent pin arms 71 and 85 and provide underlying support to the clip 88 when the latching mechanism 60 is in the closed position. Clip 88 can also be optionally provided with a protrusion 91 on an underside surface to contact extension 246 and provide a further stop mechanism when the latching mechanism 60 is in the closed position.

Figure 30A:
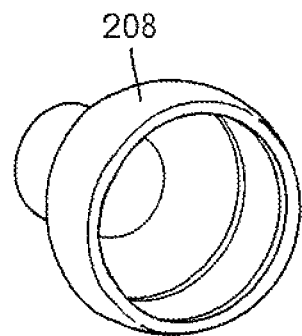
FIGS. 30A and 30B show, respectively, a perspective view of the socket and a side elevational view of the ball of the mask assembly of FIG. 22.
Figure 30B:
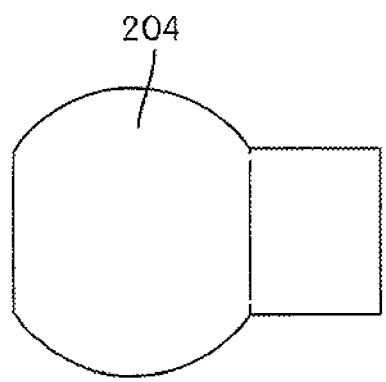

FIG. 30 shows the ball 204 and socket 208 of the embodiment of the ball and socket joint 200 shown in FIGS. 22-24.

Alternative Mask Assembly

Figure 66:
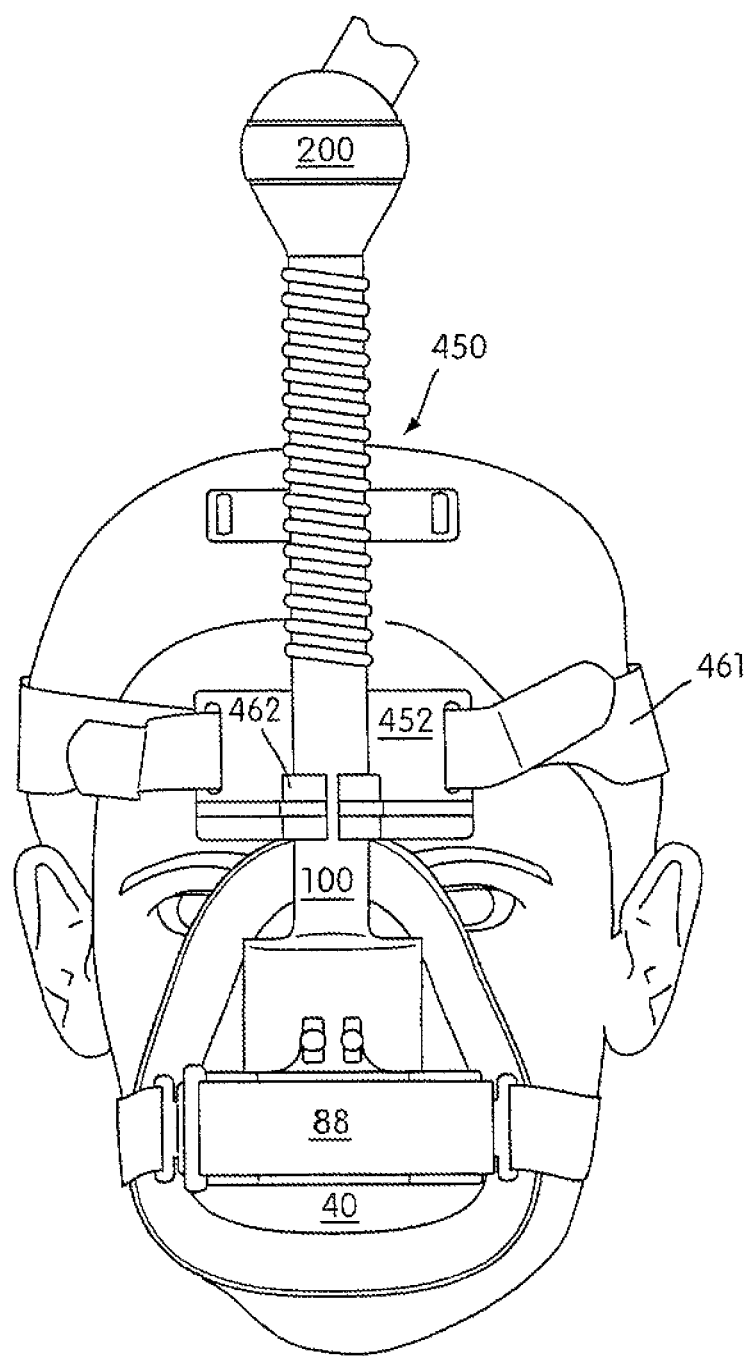
FIG. 66 shows a front view of the mask assembly of FIG. 59 installed on a user.
Figure 67:
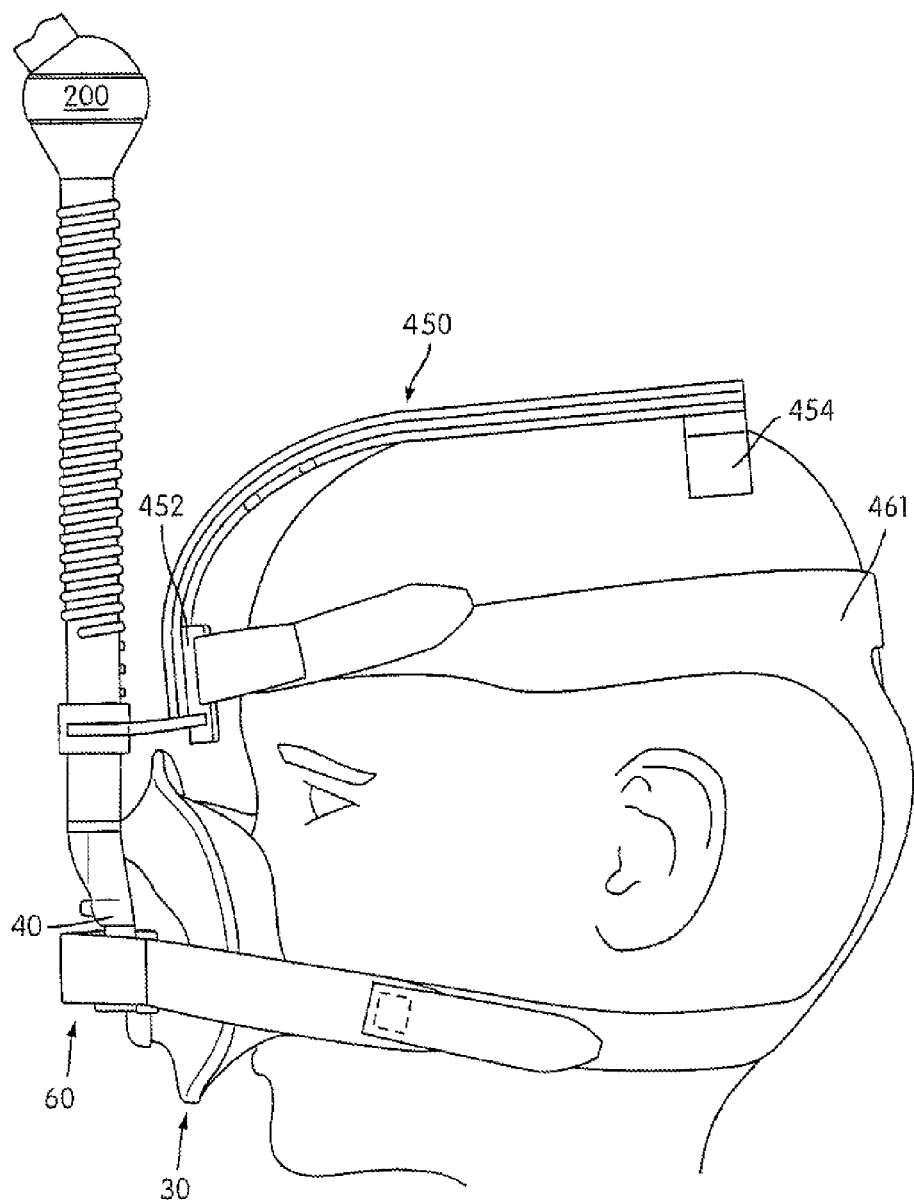
FIG. 67 shows a side view of the mask assembly of FIG. 59 installed on a user.

FIGS. 59-61 and FIGS. 66-77 show an alternative embodiment of the mask assembly 10 of the present invention. In this embodiment, the shell 40 includes an extended air inlet tube 100. A head strap 450 includes a connecting member 460 to which are connected a front harness mount 452 for connecting to a harness, an upper harness mount 456 for connecting to the harness and an upper head mount 454 for contacting an upper portion of the user's head to position and stabilize the head strap 450. Each of the harness mounts 452 and 456 include slots 458 for connecting to the harness 461 (see FIGS. 66 and 67), although other attachment mechanisms may also be used. Similarly to the embodiment shown in FIGS. 22-29, none of the front harness mount 452, the upper harness mount 456 or the shell 40 contact the user's head. Rather, when the gusset portion of the cushion is inflated, the shell 40 is pushed away from the user's face, placing tension on the front harness mount 452 and harness 461, and thus, pulling the front harness mount 452 and upper harness mount 456 away from the user's head. In the embodiment shown in FIGS. 66-67, the harness 461 is shown as only connecting to the front harness mount 452. However, in other embodiments, the harness 461 can be configured to connect to both harness mounts 452 and 456.

The front harness mount 452 includes a split retaining loop 462 that is adapted to slidingly connect to the extended air inlet tube 100. In this manner, the shell assembly 20 and cushion 30 are connected to the head strap 450 and can be adjusted vertically with respect to the head strap 450 to fit the mask assembly 10 to the particular user. The latching mechanisms 60 are similar to the latching mechanisms 60 discussed above with respect to FIGS. 22-29. However, in this embodiment of FIG. 59, each flip arm 98 of each clip 88 is configured so that when both latching mechanisms 60 are in the closed position, the flip arms 98 are positioned closely adjacent one another and upper and lower edges of each flip arm 98 are raised sufficiently to be readily grasped between the user's thumb and forefinger. Thus, both flip arms 98 can be grasped between the thumb and forefinger of the user and simultaneously manipulated with one hand to unlatch each latching mechanism 60 and quickly allow each latching mechanism 60 to move to the open position using only the one hand.

In an alternative embodiment, any of the latching mechanisms 60 described herein may be modified to include a positive latch that will hold the latching mechanism in the latched position. In one such embodiment, the positive latch can be a detent mechanism between the latching mechanism and the shell that positively holds the latching mechanism in the latched position until unlatched by the user. Such a positive latch mechanism may be configured to provide an audible indicator, such as a click, or other sensory indicator, that indicates that the latching mechanism is in the fully latched position.

The head strap 450 and air inlet tube 100 may be provided with a detent mechanism similar to the detent mechanism discussed above with respect to the embodiment shown in FIGS. 22-29 to maintain an adjusted position between the head strap 450 and the air inlet tube 100. Alternatively, the air inlet tube 100 and the retaining loop 462 may be threaded to provide an adjustable connection between the two components capable of maintaining the adjusted position.

Alternative Latching Mechanism

Figure 62:
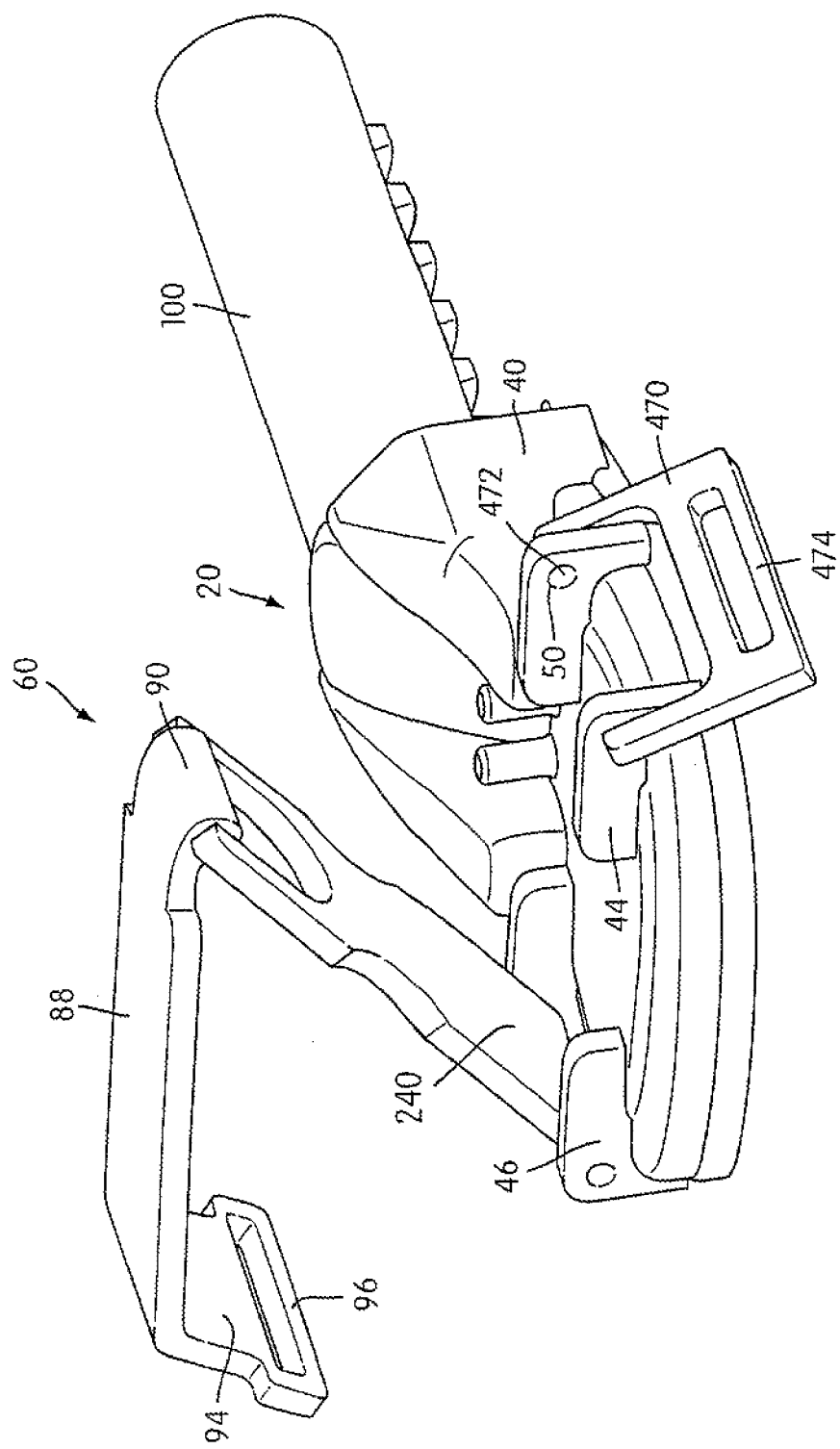
FIG. 62 shows a front perspective view of an alternative embodiment of a latching mechanism in a partially open position.
Figure 63:
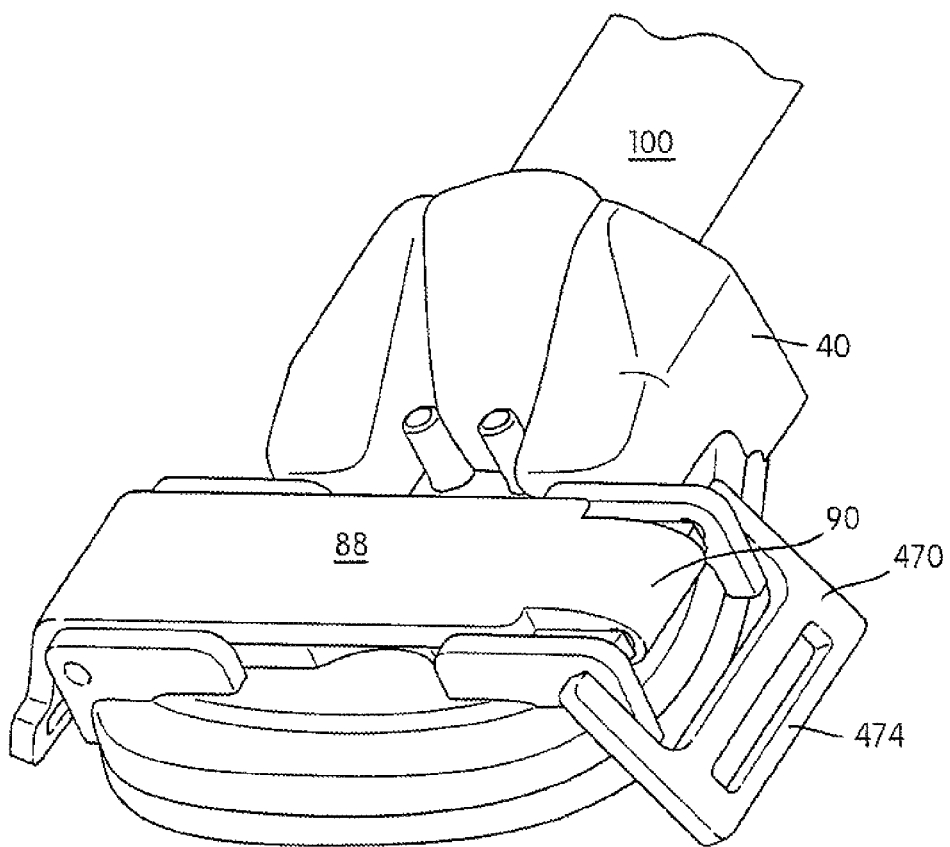
FIG. 63 shows a front perspective view of the latching mechanism of FIG. 62 in a closed position.
Figure 64:
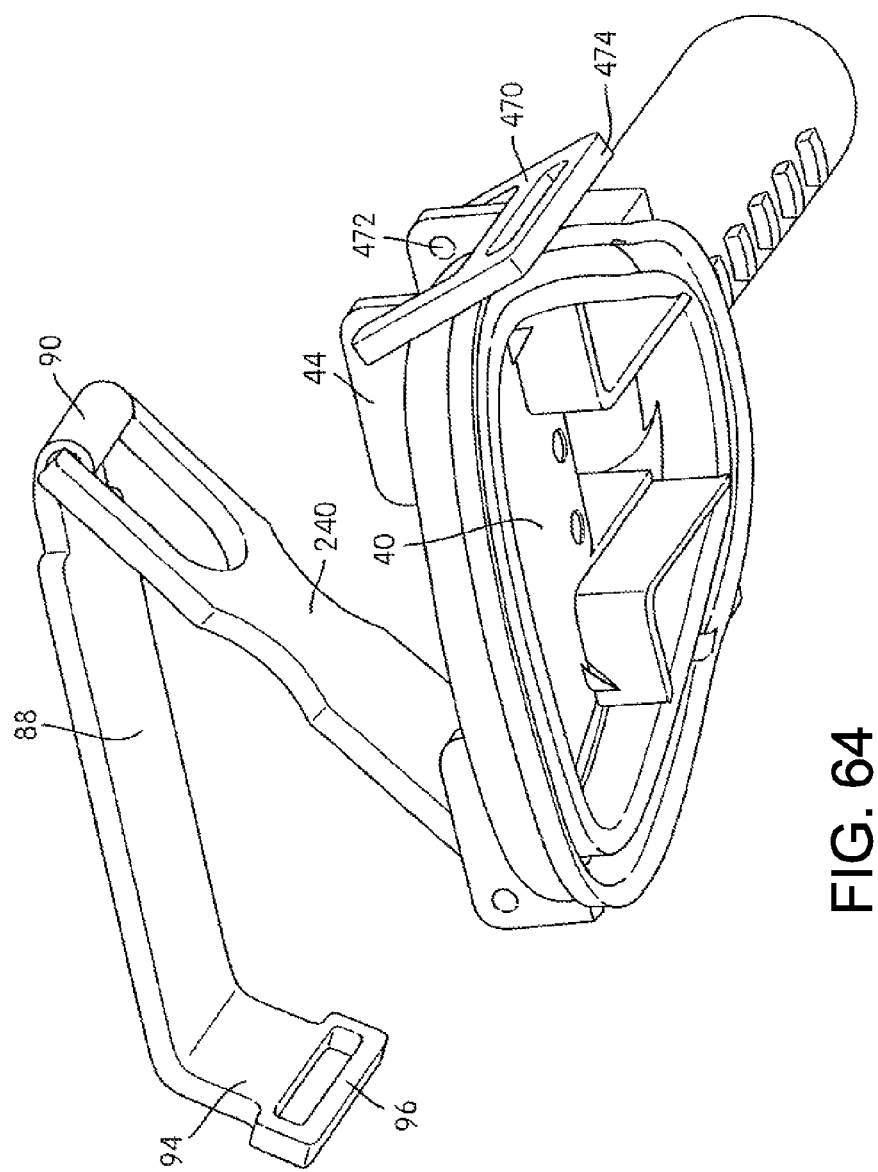
FIG. 64 shows a rear perspective view of the latching mechanism of FIG. 62 in a partially open position.

FIGS. 62-64 show an alternative embodiment of the latching mechanism 60 and shell assembly 20. In this embodiment, only one latching mechanism 60 is used. As above, the clip 88 is pivotally mounted to a clip link 240, which is pivotally mounted to the shell 40. The clip 88 includes a second end 94 having a mask harness-engaging portion 96. To provide the same amount of harness slack take-up as do the two latching mechanism embodiments disclosed above, the single latching mechanism 60 of the present embodiment is approximately twice as long as each latching mechanism discussed above. Thus, the clip 88 and the clip link 240 of this embodiment are approximately twice as long as each clip 88 and clip link 240 shown in the embodiment of FIGS. 22-29. The clip 88 can optionally include a flip arm 98 for manipulating the clip 88, similarly to the previous embodiments. However, since the first end 90 of the clip 88 extends generally to the other side of the shell 40 when in the closed position because of the increased length of the clip 88 and clip link 240, the latching mechanism 60 can also be unlatched by manipulating the exposed first end 90 of the clip 88.

In FIG. 63 since only one latching mechanism 60 is used, a harness-engaging clip 470 is provided in this embodiment to engage the second side of the harness. As depicted in FIG. 64, the harness engaging clip 470 includes a pair of inwardly extending pins 472 to pivotally engage the bore 50 of the shell 40, as does the left latching mechanism of the embodiments discussed above, and a mask harness engaging portion 474 for engaging the harness. Since the pins 472 engage the bore 50 from the outside of the flange assembly 44, the harness engaging clip 470 does not interfere with the latching mechanism 60 when in the closed position, even though the width of the clip link 240 is preferably set so as to engage the inner sides of the flange assembly 44 in the closed position to provide stability to the latching mechanism 60. Alternatively, a fixed harness-engaging portion can be provided on the shell itself, but with the present embodiment, the same shell 40 can be used in either a double or a single latching mechanism mode. Also, with the embodiment shown, the latching mechanism 60 can be attached to the shell 40 on either side of the shell 40, as can the harness engaging clip 470, to provide left and right handed mask versions, using the identical components.

In a modification of this embodiment, two latching mechanisms 60 of the increased length can be provided on the shell 40 with one latching mechanism positioned by an extended flange assembly to be further out from the shell 40 than the other latching mechanism such that the more outwardly positioned latching mechanism can overlay the inner latching mechanism. In a latching mode, the inner latching mechanism would first be manipulated to the closed position and then the outer latching mechanism. In an unlatching mode, the process would be reversed. Such an embodiment would provide approximately double the harness slack take-up ability, as compared to the embodiments described above. Alternatively, the inner latching mechanism can be provided with a grasping member that does not interfere with movement of the outer latching mechanism such that manipulation of the grasping member by the user opens the inner latching mechanism, which in turn, simultaneously opens the outer latching mechanism.

Each of the latching mechanisms described herein operate on the same over center principal as described with respect to FIGS. 8A and 8B.

Alternative Head Mount Adjustment Mechanism

Figure 31:
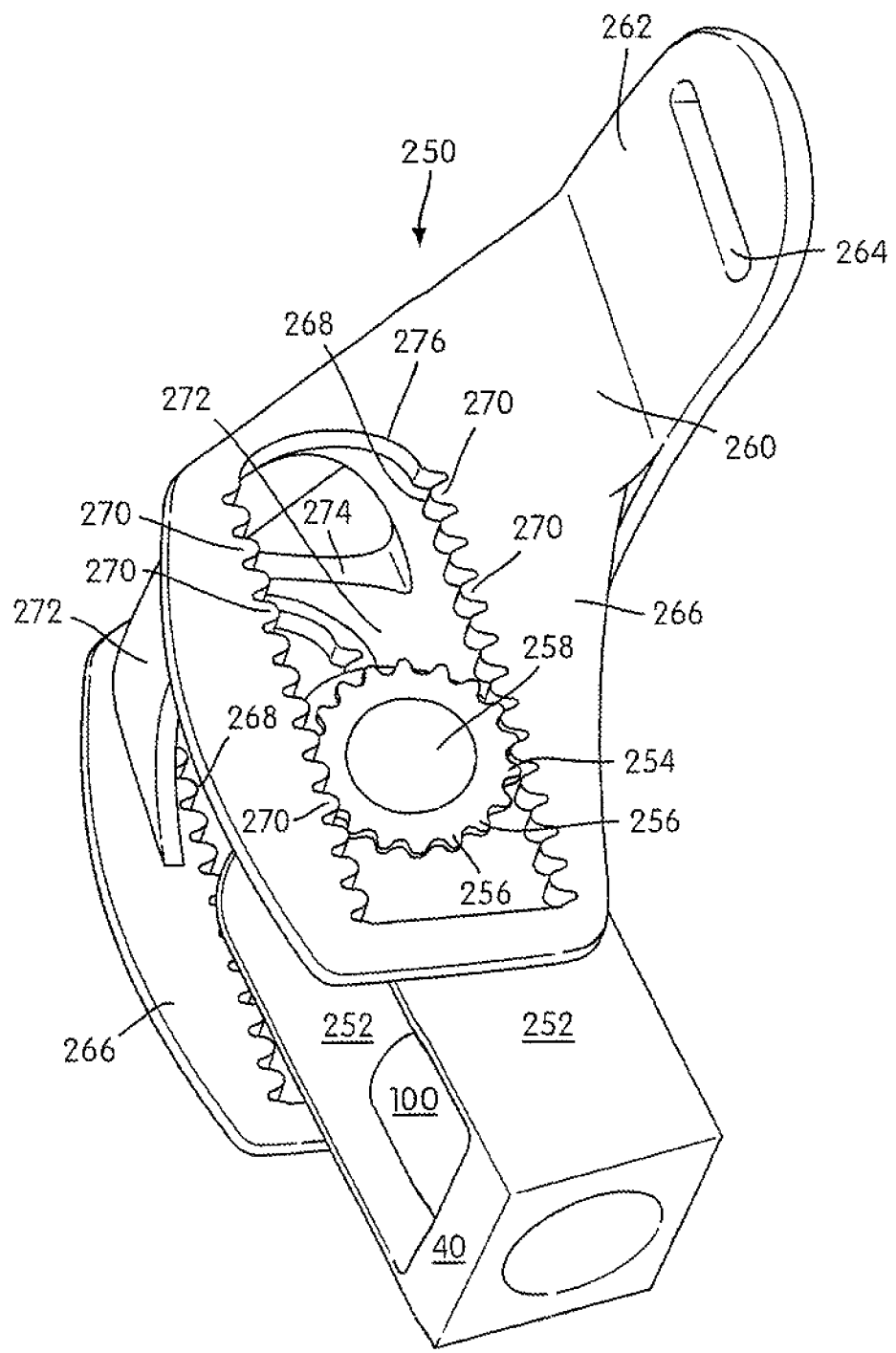
FIG. 31 shows a perspective view of an alternative embodiment of a head mount adjustment mechanism of the mask assembly of the present invention.
Figure 32:
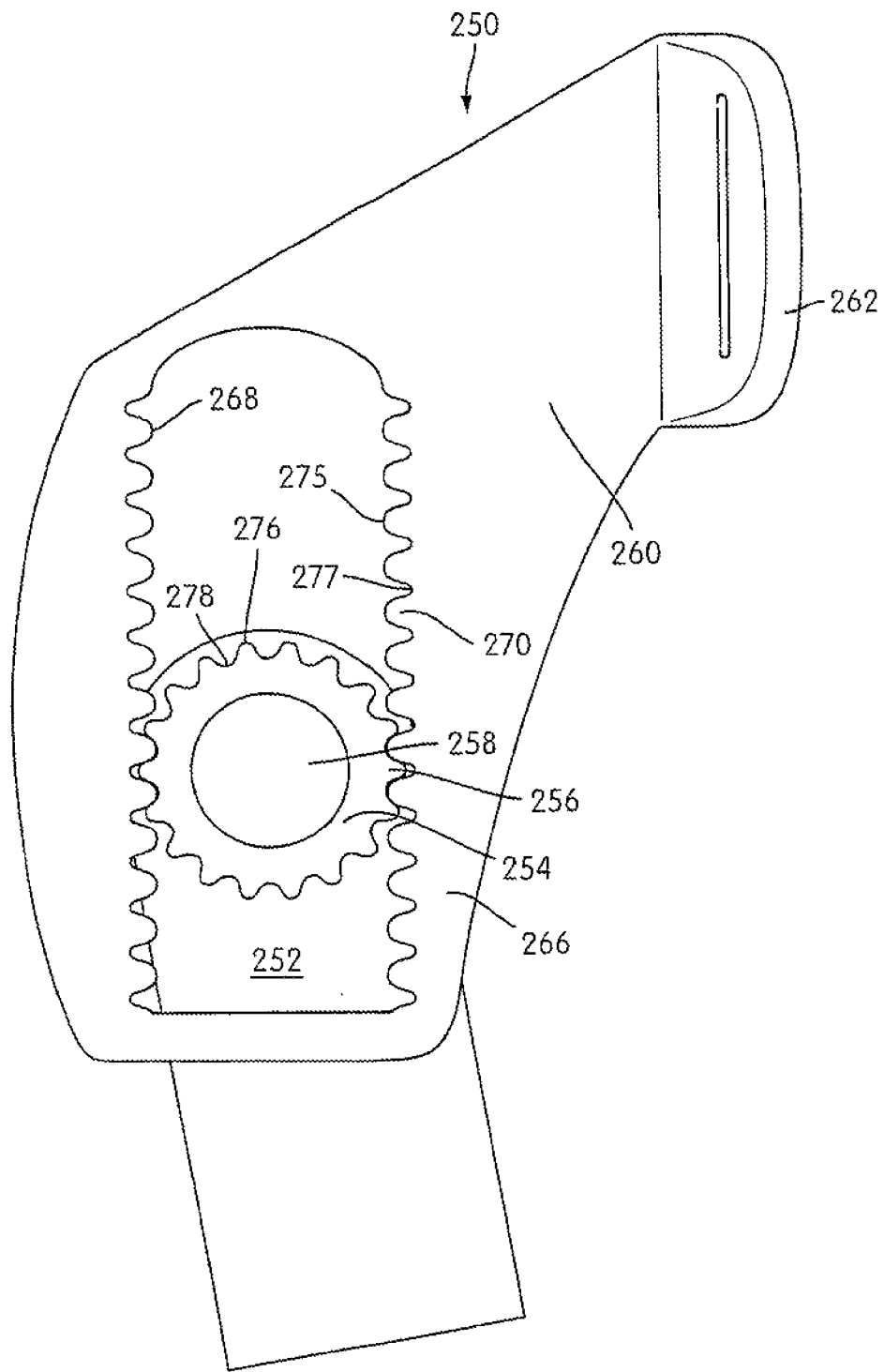
FIG. 32 shows a side elevational view of the head mount adjustment mechanism of FIG. 31.

FIGS. 31-32 show an alternative embodiment of a head mount adjustment mechanism 250. The mechanism includes a pair of generally parallel extending spring tabs 252 extending from the shell 40 (only a portion of which is shown) on opposite sides of the air inlet tube 100. A generally round locking gear 254 is fixedly mounted to a distal end of each spring tab 252 and, in the preferred embodiment, is integrally cast with the spring tab 252. A plurality of teeth 256 are evenly spaced around a periphery of each locking gear 254. In a referred embodiment, the locking gears 254 are coaxial with one another and each locking gear 254 has a raised projection 258 for manipulation of the locking gear/spring tab assembly by the user.

Head mount 260 includes a base 262 for engaging a user's forehead and slots 264 or other attachment mechanisms for attaching the head mount 260 to a head strap or harness. The head mount 260 also includes a pair of generally parallel extending brackets 266. Each extending bracket 266 includes an elongated slot 268 passing therethrough with longitudinal axes of the elongated slots 268 being generally parallel to one another. Each elongated slot 268 includes a pair of generally straight, parallel opposing rows of locking teeth 270. The locking teeth 270 and locking gear teeth 256 are each configured so that they can readily and stably engage each other. Likewise, the pitch of the locking teeth 270 is set to correspond to the pitch of the locking gear teeth 256 and the distance between the rows of teeth 270 is set to correspond to a diameter of the locking gear 254 to provide proper engagement between the teeth 270 and the gear 254. In the embodiment shown in FIGS. 31-32, the locking teeth 270 have generally rounded crowns 275 and more pointed roots 277 while the teeth 256 correspondingly have more pointed crowns 276 and generally rounded roots 278. Other gear shapes and configurations can also be used.

Since the opposing rows of teeth 270 are generally parallel and space apart a distance to readily mesh with the generally round locking gear 254, the locking gear 254 can be engaged with the rows of teeth 270 at a plurality of discrete points along substantially all of the length of the slot 268, thereby altering a distance between the head mount 260 and a main body of the shell 40. This configuration also allows the angle of the head mount 260 with respect to the shell 40 to be altered (again within the limitations imposed by the pitch of the teeth) by engaging the teeth 270 with different teeth 256 around the locking gear 254. This angle does not extend entirely around the locking gear 254 since, at some point, some portion of the head mount 260 will contact and be stopped by some portion of the shell 40 or cushion 30. However, this is of little concern because in most instances for most users, the desired angle of the head mount 260 with respect to the shell 40 will fall within a limited range of substantially less than 90°.

Figure 33:
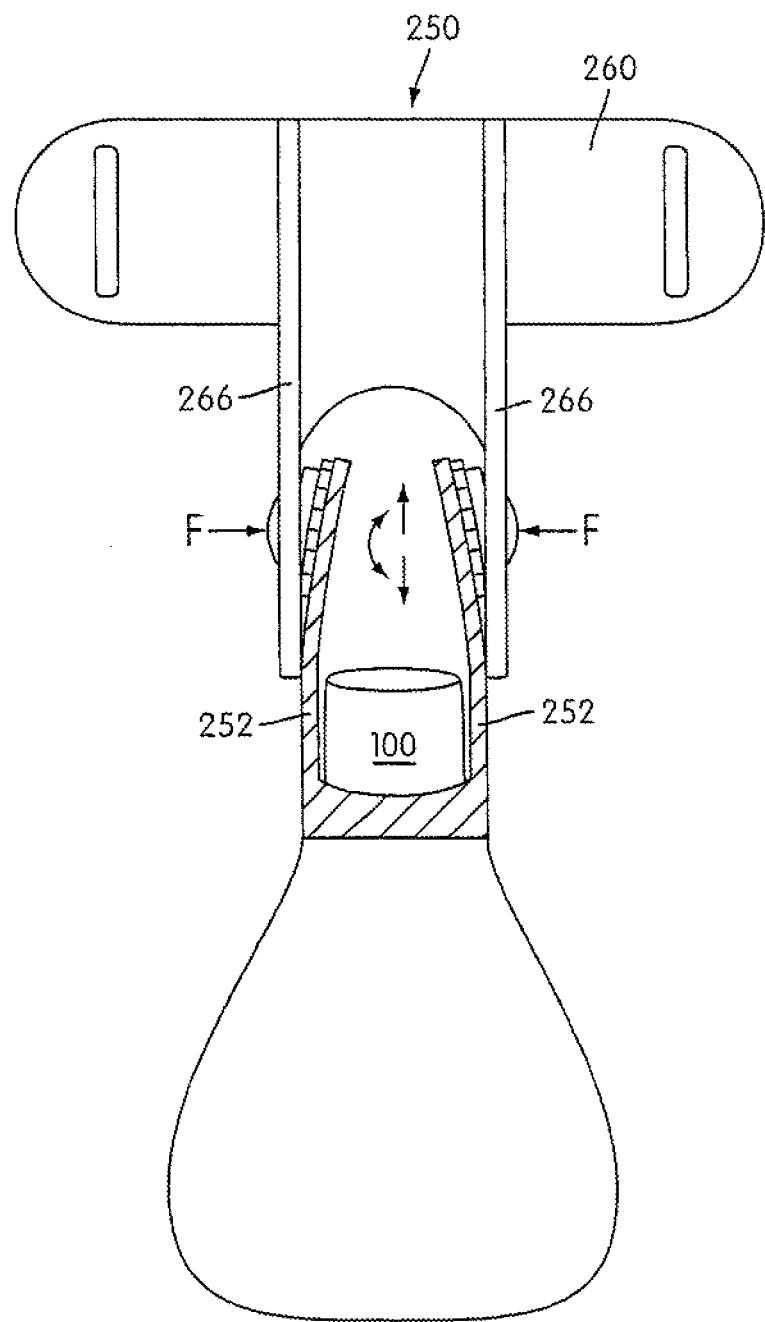
FIG. 33 shows a front elevational view of the operation of the head mount adjustment mechanism of FIG. 31.

Thus, by selecting which teeth 270 engage which teeth 256, both the distance and the angle between the head mount 260 and the shell 40 can either be altered simultaneously or altered independently of one another to provide the desired fit for the user. To this end, the spring tabs 252, while fairly rigid, are flexible enough such that when the user squeezes the opposing projections 258 extending above the slots 268, the spring tabs will move toward one another, thereby disengaging the locking gear 254 from the locking teeth 270. See FIG. 33. The desired distance and angle between the head mount 260 and shell 40 can then be set as desired and the spring tabs 252 released to engage the locking gear 254 with the locking teeth 270 and lock the head mount 260 in the desired position. The degree of flexibility of the spring tabs 252 can be altered by altering a thickness, material and/or shape thereof.

To facilitate engagement between the teeth 256 and teeth 270, an outer edge of the teeth 256 and/or an inner edge of the teeth 270 can be rounded. The thickness of the teeth 256 and 270, and thus the amount of engagement between the respective teeth, will be set based on the magnitude of forces that the adjustment mechanism is expected to encounter in use, with higher expected forces suggesting thicker teeth and greater engagement between the respective teeth. To increase the strength and stability of the head mount 260, one or more support members 272 can interconnect the extending brackets 266. In addition, the head mount includes a passageway 274 positioned between the extending brackets 266 so that an air supply tube can be routed therethrough for connection to the air inlet tube 100. Further, ends of the slots 268 can be radiused, as shown at 276, to provide increased clearance for the locking gear 254, thereby allowing an increased length of engagement between the locking gear 254 and the rows of teeth 270. Alternatively, the interacting structures on the head mount 260 and the shell 40 can be reversed.

Figure 34:
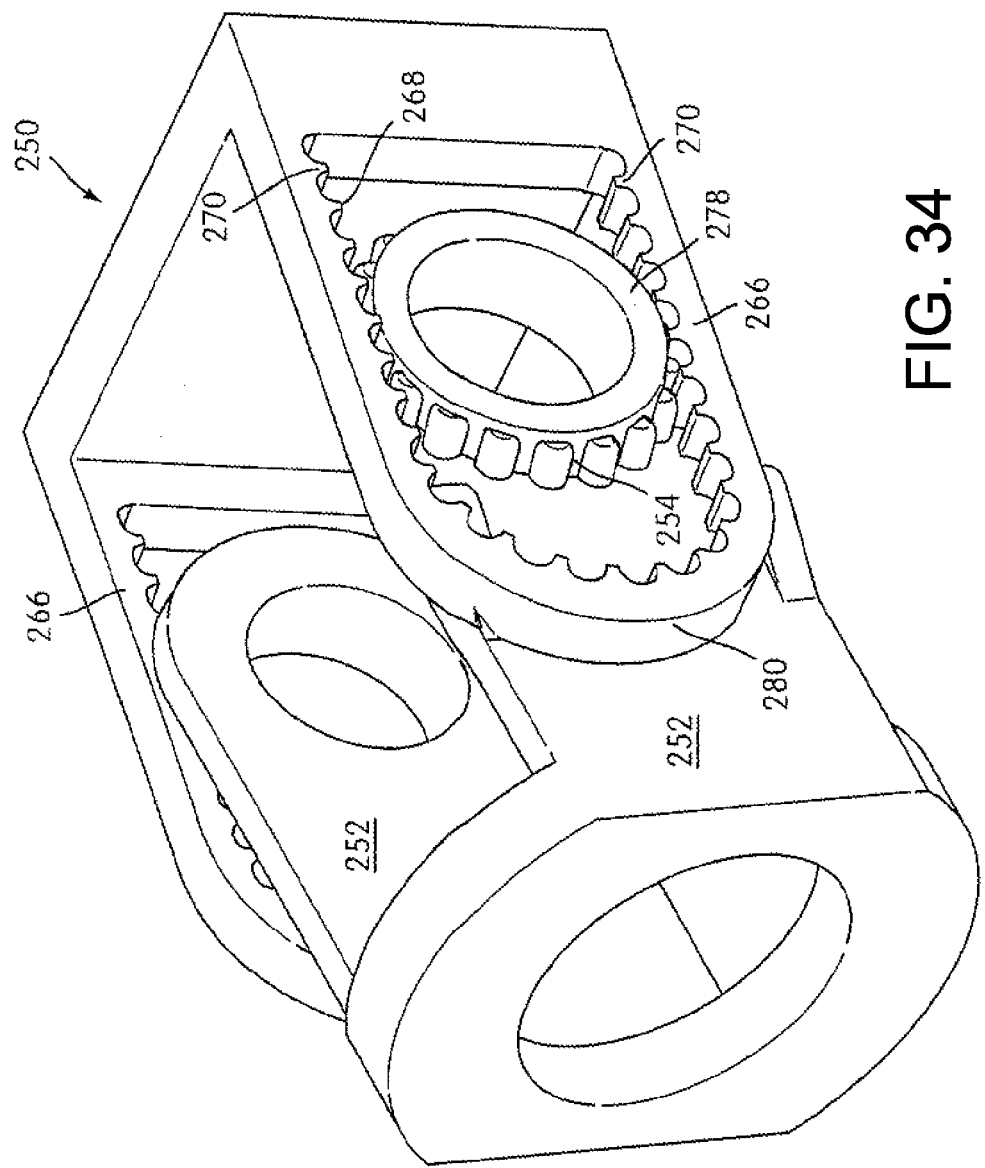
FIG. 34 shows a perspective view of an alternative embodiment of a head mount adjustment mechanism of the mask assembly of the present invention.
Figure 35:
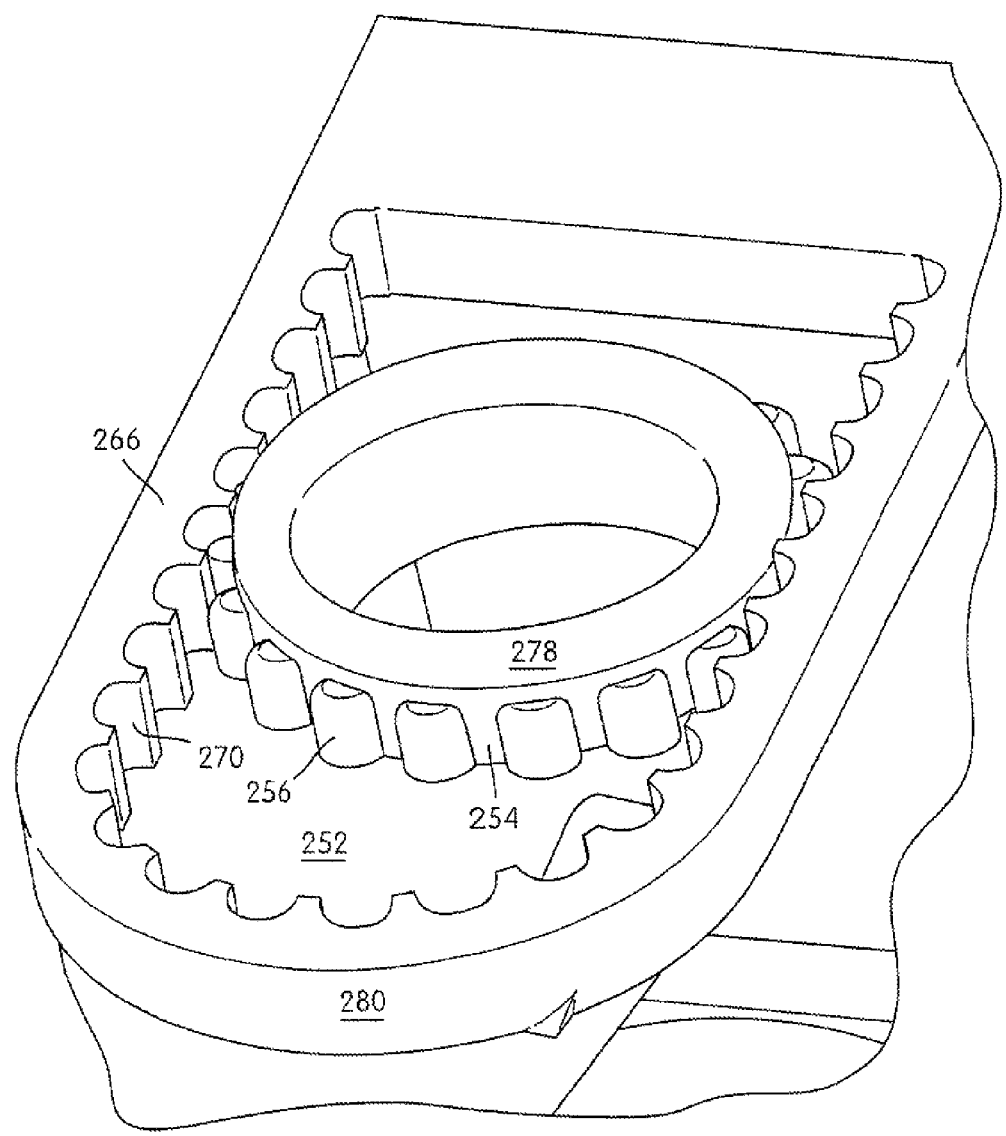
FIG. 35 shows an enlarged perspective detail view of the head mount adjustment mechanism of FIG. 34.
Figure 36:
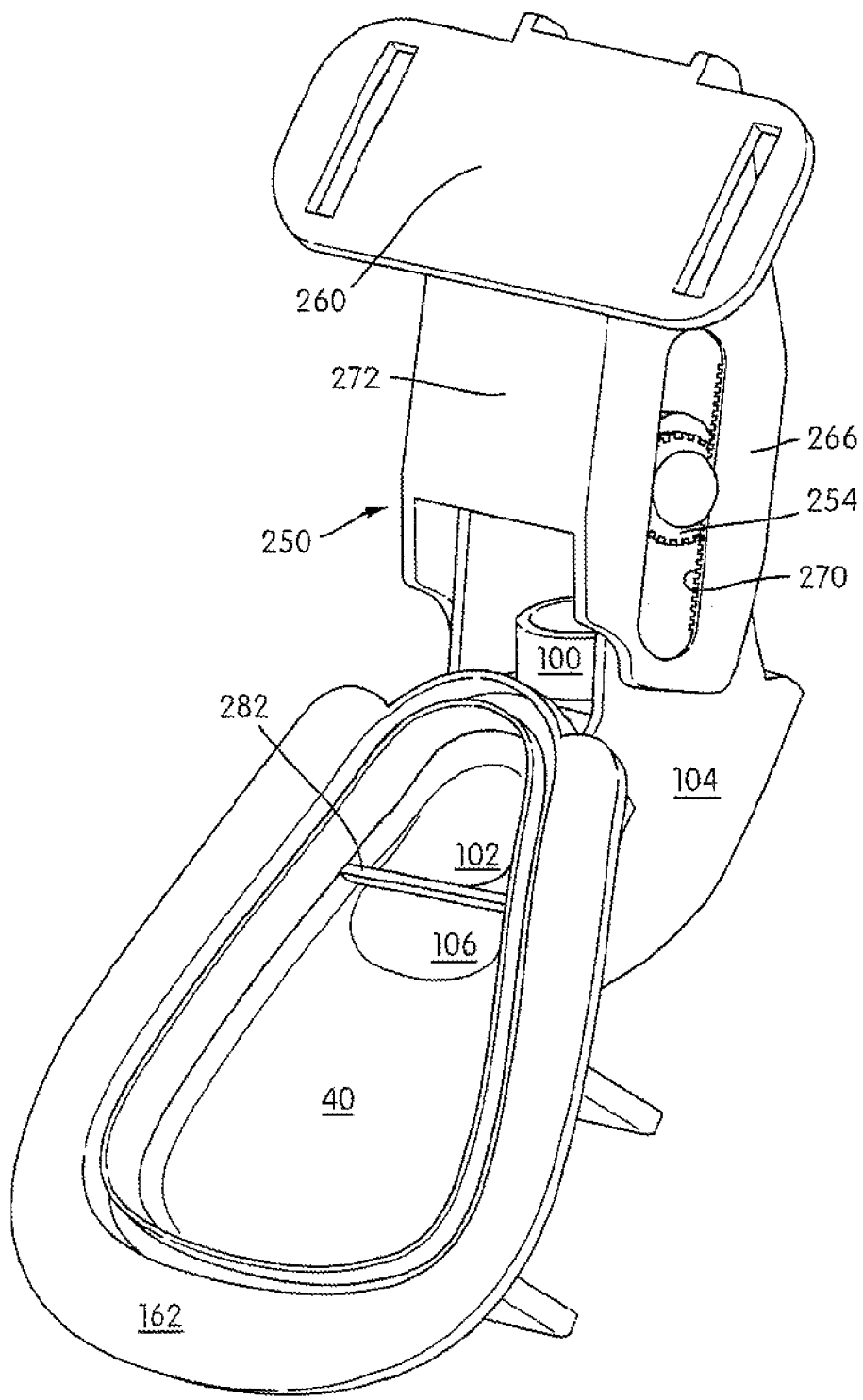
FIG. 36 shows a rear perspective view of the head mount adjustment mechanism of FIG. 34 mounted to an alternative embodiment shell of the mask assembly of the present invention.
Figure 37:
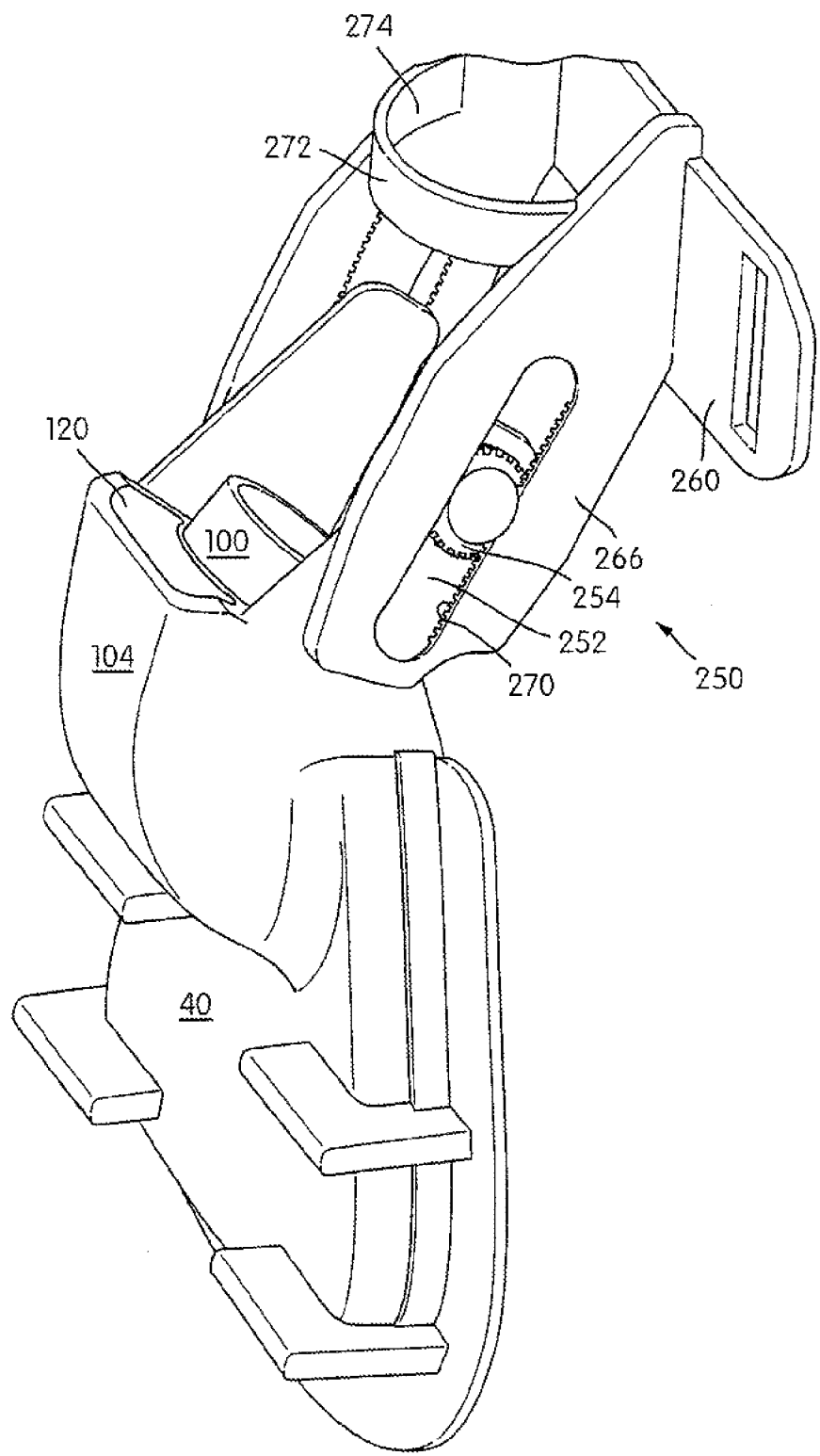
FIG. 37 shows a side perspective view of the head mount adjustment mechanism and shell of FIG. 36.
Figure 38:
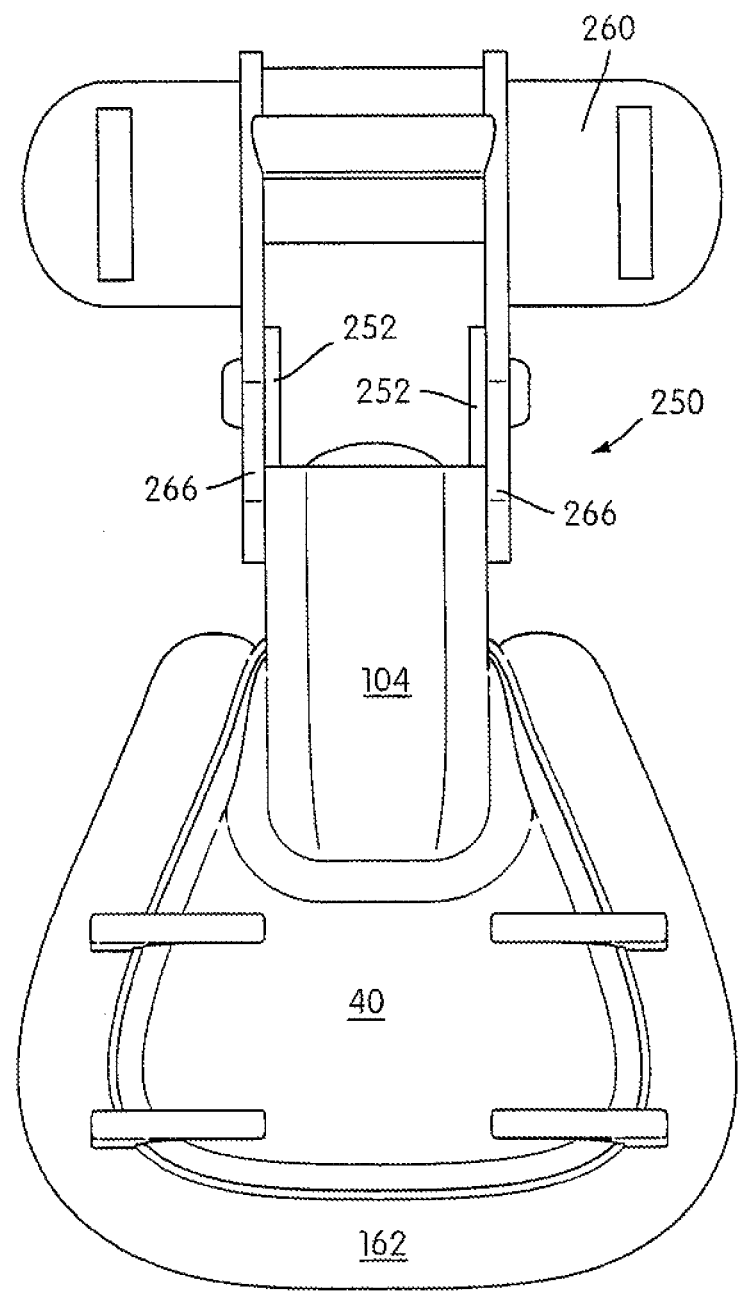
FIG. 38 shows a front elevational view of the head mount adjustment mechanism and shell of FIG. 36.
Figure 39:
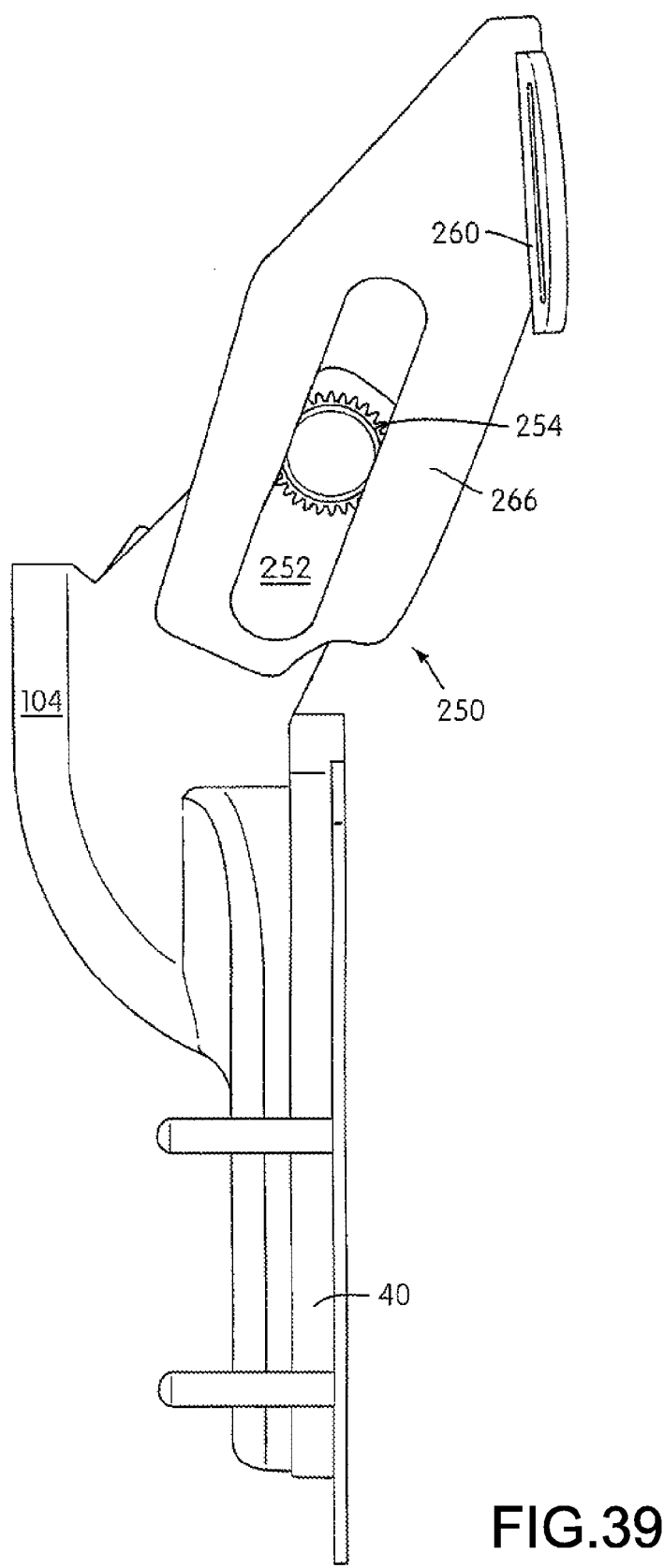
FIG. 39 shows a side elevational view of the head mount adjustment mechanism and shell of FIG. 36.
Figure 40:
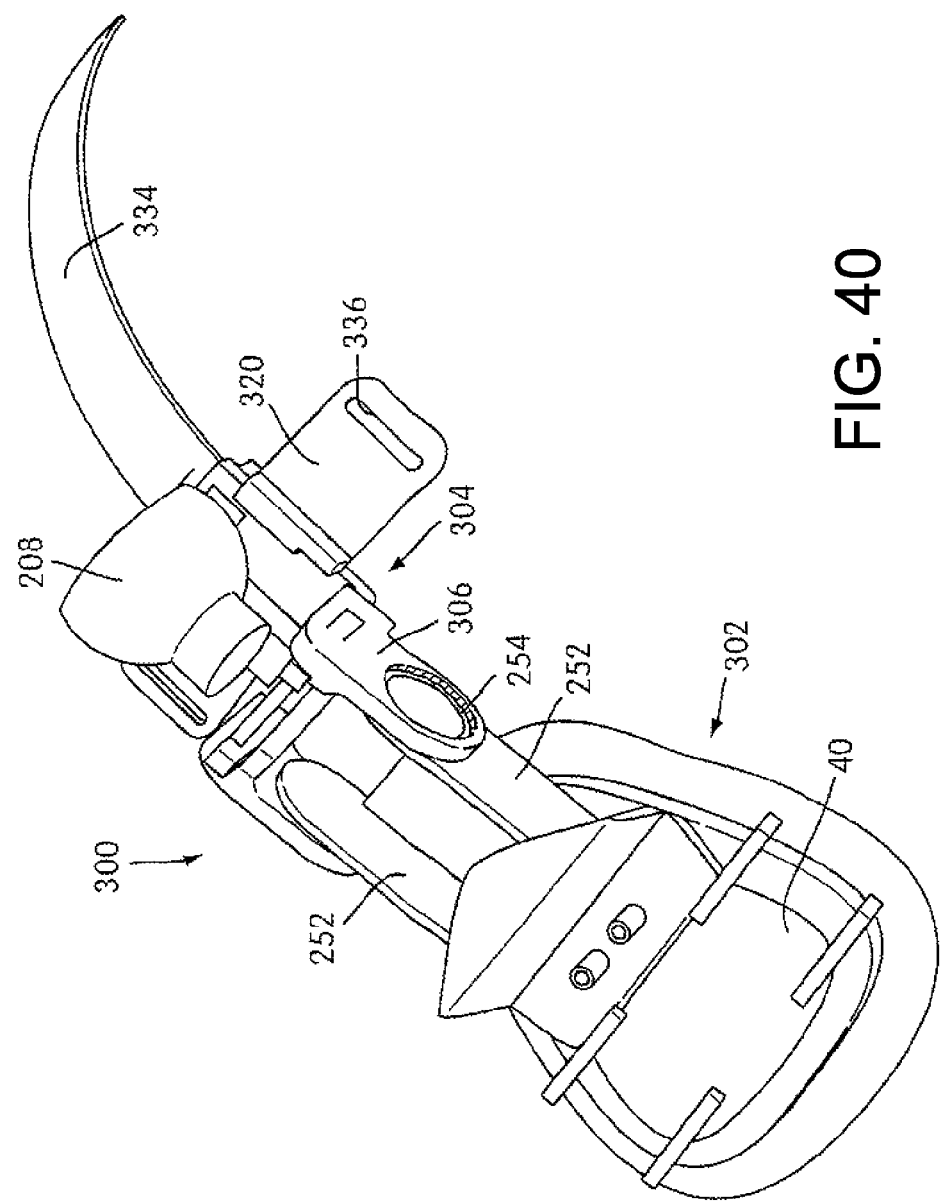
FIG. 40 shows a front perspective view of an alternative embodiment of a head mount adjustment mechanism mounted to an alternative embodiment shell of the mask assembly of the present invention.

In an alternative embodiment of the adjustment mechanism 250 shown in FIGS. 34-35, each locking gear 254 is provided with a generally cylindrical projection 278. The projection 278 has an outer diameter approximately the same or slightly less than the distance between the crowns of opposing rows of teeth 270 and a height that extends beyond the slot 268, preferably by a sufficient distance such that when the spring tabs 252 are squeezed together for adjustment of the mechanism 250, the projections 278 remain engaged with the teeth of their respective slots 268. In this way, increased stability is provided between the head mount 260 and the shell 40 during adjustment of the mechanism 250 since the projections 278 remain movably engaged with the rows of teeth 270 even though the locking gear 254 is disengaged from the rows of teeth 270.

In this embodiment depicted in FIGS. 34-35, a distal end 280 of each slot 268 is curved and provided with teeth 270 such that when the distance between the head mount 260 and the shell 40 is adjusted to its maximum, there is engagement between the teeth 270 and the teeth 256 around 180° of the locking gear 254. This increased engagement provides additional stability to the adjustment mechanism 250 at a time when the increased distance between the head mount 260 and the shell 40 is acting to decrease stability of the adjustment mechanism 250. The curved, toothed distal end 280 of the slot 268 also continues to provide angular adjustment ability to the mechanism 250 at the maximum adjustment distance of the mechanism 250. In this embodiment, further raised projections 258 are not needed for manipulation by the user and the projections 278 can optionally be dished or hollow for material savings. In this embodiment, the teeth 256 and 270 have a slightly different configuration than in the previous embodiment and the outer diameter of each projection is approximately the same as the root diameter of the locking gear 254.

FIGS. 36-39 show perspective views of the adjustment mechanism 250 with an alternative embodiment of the shell 40. In this embodiment, one exhalation duct port 106 is provided below air inlet tube port 102 with a laterally extending baffle 282 extending therebetween to separate the two gas flows through these ports. In this embodiment, the duct port 106 connects to a single exhalation duct 104 that extends upward and partially surrounds the air inlet tube 100 with exhalation gases exiting through a single exhaust port 120.

Alternative Head Mount Adjustment Mechanism

FIGS. 40-51 show an alternative embodiment of a head mount adjustment mechanism 300. A shell portion 302 of the adjustment mechanism may be the same as any of the shell embodiments shown in FIGS. 31-39 and includes spring tabs 252, locking gears 254 and a plurality of locking teeth 256 positioned around a periphery of the locking gear 254. The shell 40 may be changed if desired.

Figure 41:
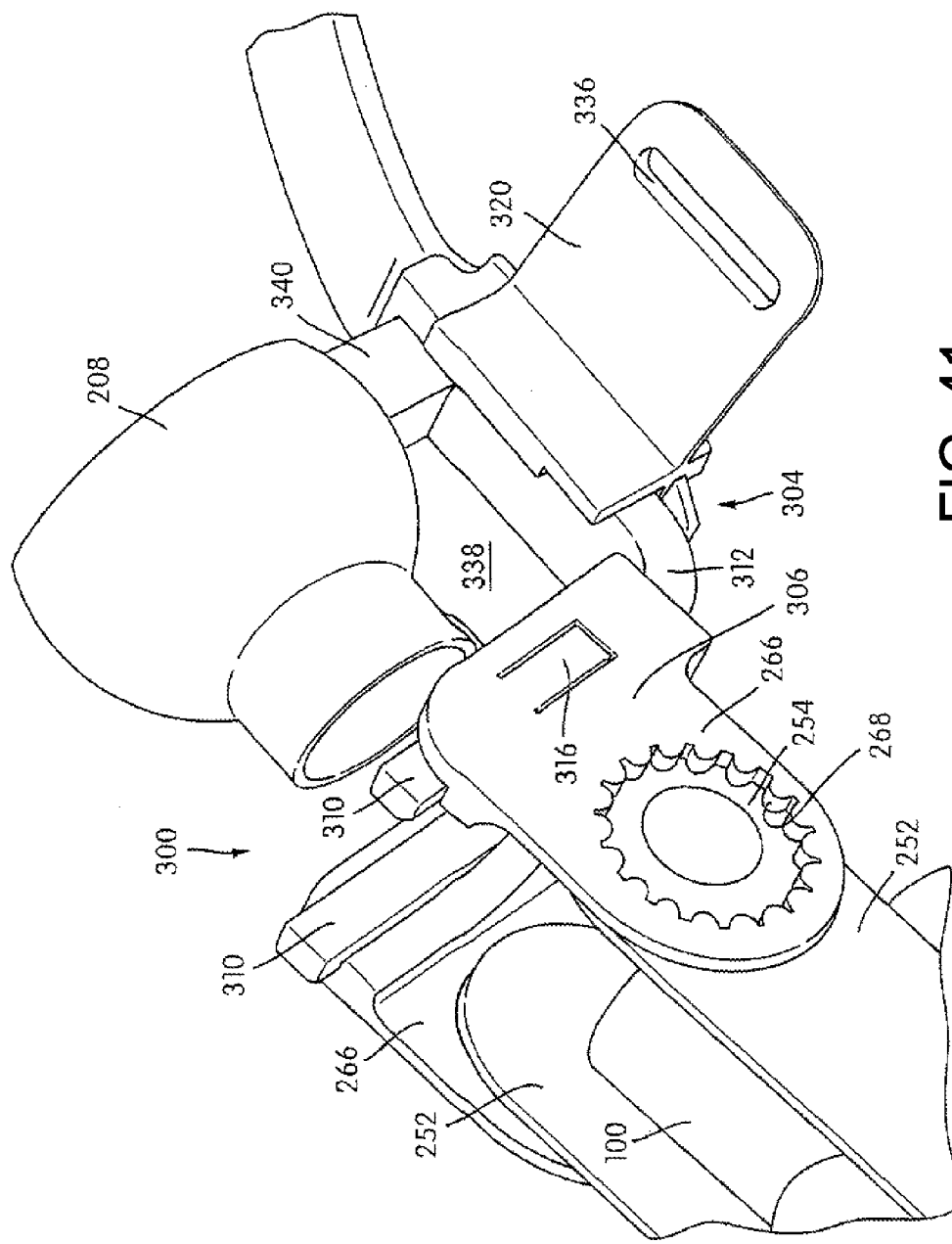
FIG. 41 shows a perspective detail view of the head mount adjustment mechanism and shell of FIG. 40.
Figure 42:
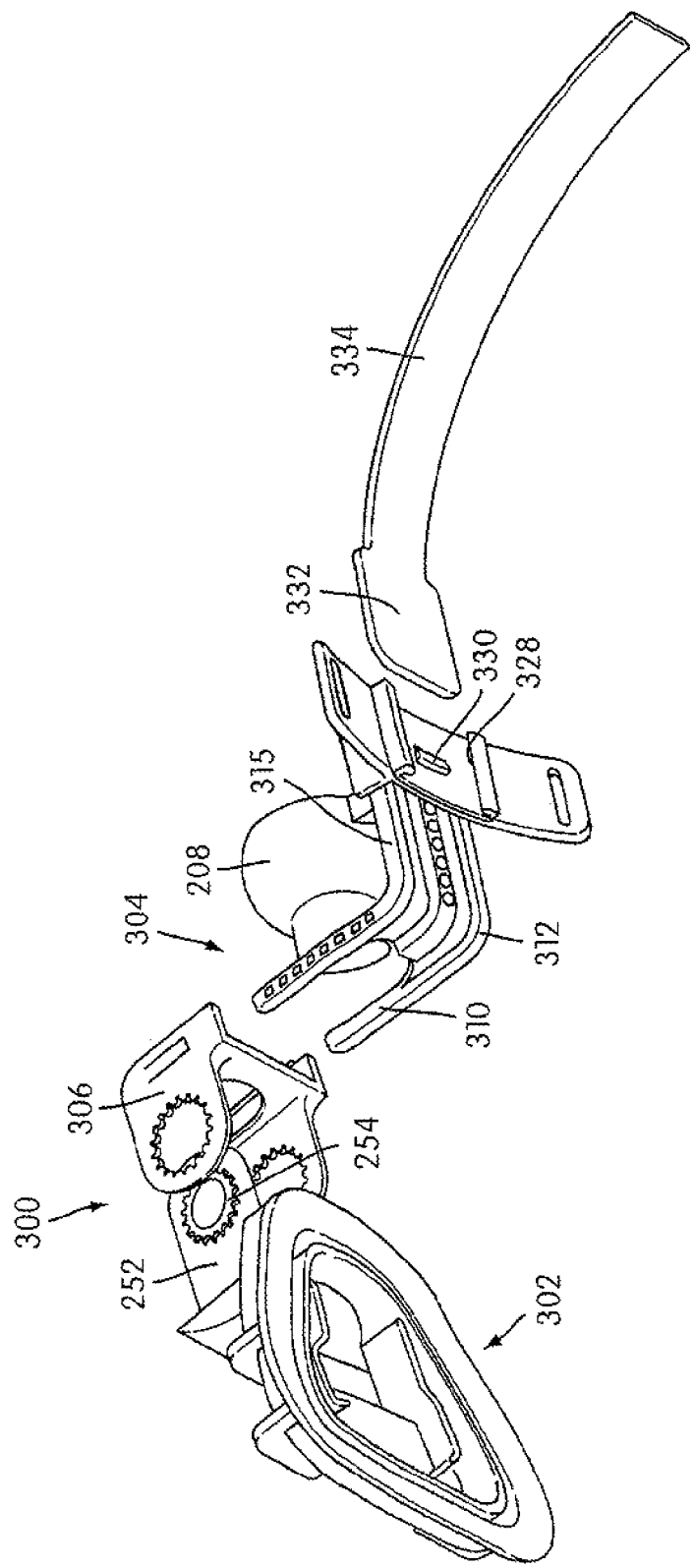
FIG. 42 shows a rear exploded view of the head mount adjustment mechanism and shell of FIG. 40.

In FIG. 41, a head mount portion 304 of the adjustment mechanism 300 is different from the previous embodiments. The head mount portion 304 includes a locking bracket 306 having a pair of generally parallel extending brackets 266. Each extending bracket 266 includes a generally round slot 268 passing therethrough with the two slots 268 being generally coaxial to one another. Each slot 268 includes plurality of locking teeth 270 positioned around an inner circumference of the slot positioned and configured to engage the teeth 256 in a locking manner. Since each slot 268 is round, the engagement between the teeth 270 and the teeth 256 of this embodiment only allow for changes of an angle between the locking bracket 306 and the shell 40 and does not allow for a height adjustment between the two components. This angle can be adjusted by depressing the spring tabs 252 and rotating the locking bracket 306 in the same manner as was described above with respect to the previous embodiments.

Figure 43:
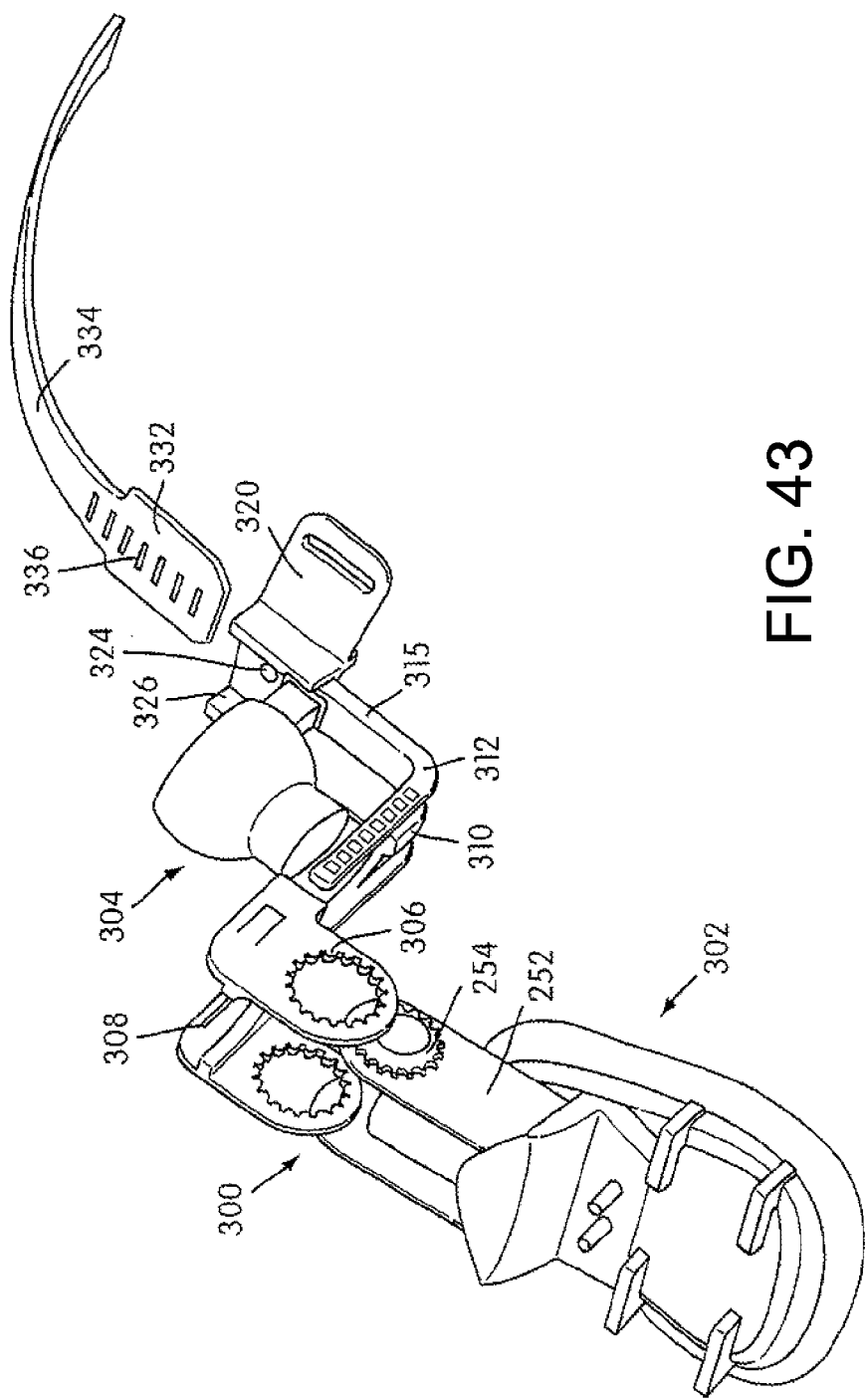
FIG. 43 shows a front exploded view of the head mount adjustment mechanism and shell of FIG. 40.

In FIG. 43, the locking bracket 306 includes a retaining channel 308 sized and configured to slidingly receive a first extending tab 310 of a connecting bracket 312. The connecting bracket 312 includes a second extending tab 315 extending at an angel with respect to the first extending tab 310. The connecting bracket 312 is generally L-shaped, although the angle between the first and second extending tabs need not be 90°, and in the preferred embodiment, is closer to 100°. However, any angle can be chosen that provides the best fit for the intended user. In the embodiment shown, the first extending tab 310 is relieved for much of its distal extent to provide clearance for an air tube although such clearance can also be provided by an enclosed slot on the tab 310. Each side of the tab 310 includes a plurality of spaced apart detent slots 314. Correspondingly, locking bracket 306 includes a pair of detent spring arms 316, each having a raised detent projection 318 projecting into the retaining channel 308 from opposing sides and adapted to engage respective pairs of the detent slots 314 to lock the connecting bracket 312 in a desired adjusted position with respect to the locking bracket 306. While the locking bracket preferably uses two detent spring arms 316, one or more spring arms can optionally be used. Further, while it is preferred that the raised detent projections 318 be positioned at the end of spring arms to ease movement, adjustment and longevity of the components, the raised detents need not be on spring arms and can be merely positioned on opposing interior walls of the retaining channel 308.

With this construction, the position of the connecting bracket 312 can be adjusted fore and aft with respect to the locking bracket/shell/cushion, which in turn, adjusts the fore and aft position of a head mount 320 attached to the connecting bracket 312 with respect to the locking bracket/shell/cushion, by sliding the tab 310 within the retaining channel 308 until the raised projections 318 engage the detent slots 314 in the desired position and lock the connecting bracket 312 with respect to the locking bracket 306. The raised detent projections 318 and/or the detent slots 314 can be chamfered to lessen the amount of force required to move the connecting bracket 312 with respect to the locking bracket 306. Likewise, the size, shape and configuration of the spring arms 316 can be altered to vary a spring force imparted by the spring arms 316 on the raised projections 318 to adjust the force required to move the connecting bracket 312 within a desired range. The distal end of tab 310 can be chamfered for ease of insertion into retaining channel 308.

The second extending tab 315 of connecting bracket 312 includes a centrally positioned row of spaced apart detent slots 322 that are adapted to engage a detent projection 324 positioned in a first retaining channel 326 of head mount 320. Although the detent projection 324 is not shown positioned on a spring tab, it can be where desired. Similarly to the engagement between first extending tab 310 and retaining channel 308 of connecting bracket 312, second extending tab 315 is adapted to engage retaining channel 326 of head mount 320 to provide a generally vertical adjustability to the head mount 320 with respect to the connecting bracket/shell/cushion. The engagement of the detent projection 324 with one of the plurality of detent slots 322 maintains the head mount 320 in the adjusted position until readjusted.

Head mount 320 may also includes a second retaining channel 328 in which a detent projection 330 is positioned. The second retaining channel 328 is positioned adjacent the first retaining channel but on an opposite side of the head mount 320. The second retaining channel 328 is adapted to engage an extending tab 332 on a head strap 334. The extending tab 332 includes a row of detent slots 336 adapted to selectively engage the detent projection 330 and maintain and adjusted position of the head strap 334 with respect to the head mount 320, similarly to manner in which the detent slots 322 and the detent projection 324 maintain the adjusted position of the head mount 320 with respect to the connecting bracket. 312. In this way, the head strap 334 can be adjusted with respect to the head mount 320, shell 40 and cushion 30. Head strap 334 is adapted to engage further straps or a harness to secure the mask to the head. The head mount 320 can also include a foam or other soft liner on its underside for comfortable engagement with the user's head. The head mount 320 includes slots 336 or other attachment devices for connection to other head straps or a harness.

Figure 44:
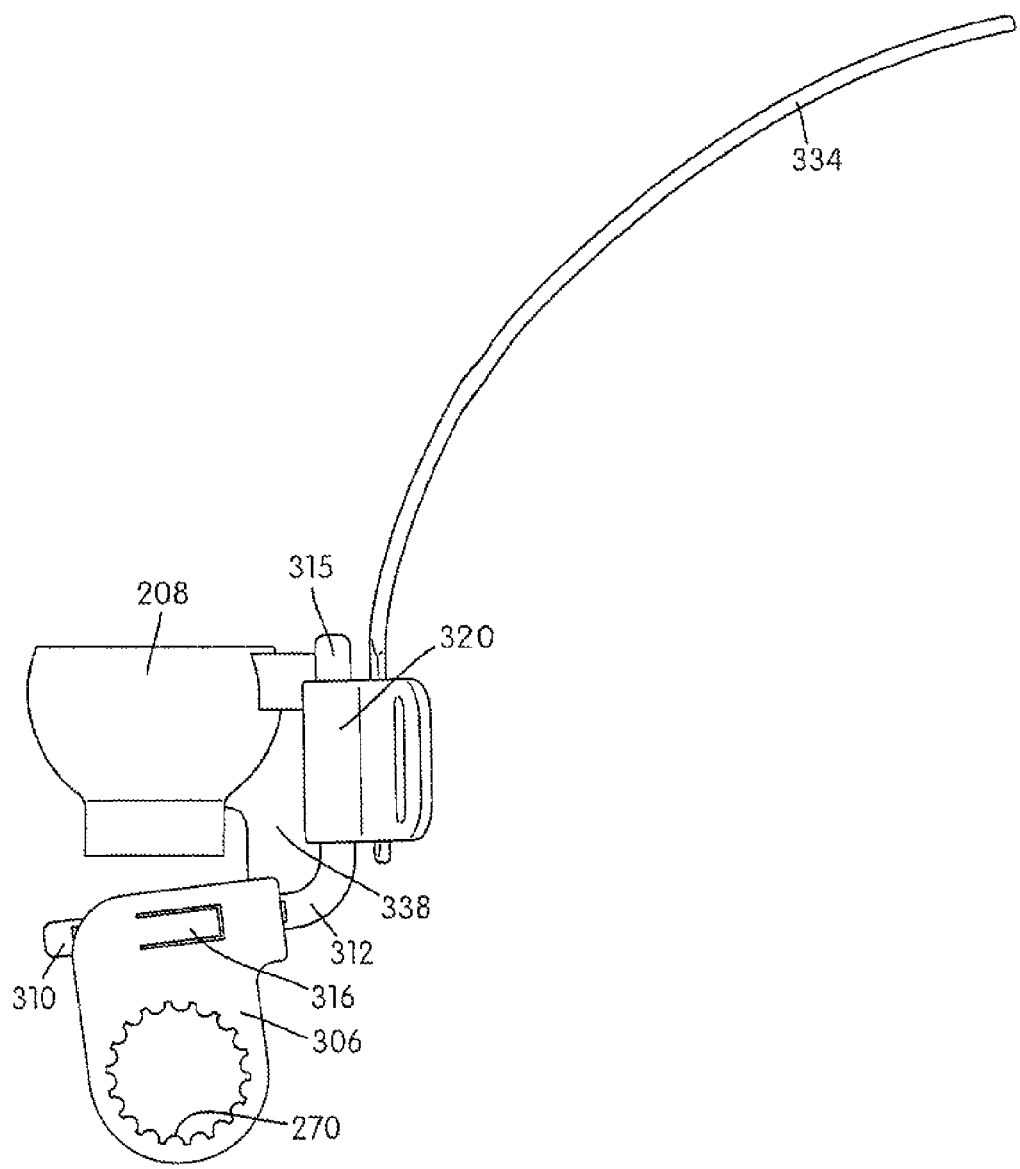
FIG. 44 shows a side elevational view of a portion of the head mount adjustment mechanism of FIG. 40.
Figure 45:
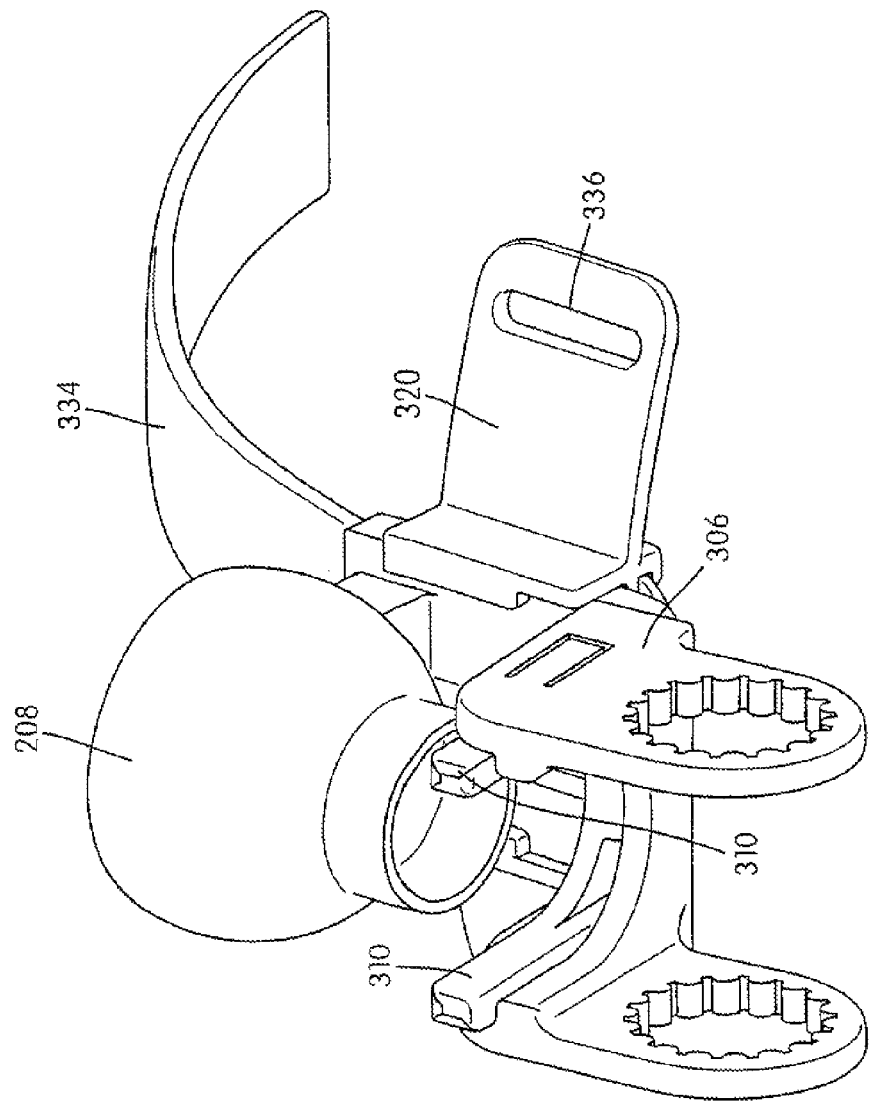
FIG. 45 shows a front perspective view of a portion of the head mount adjustment mechanism of FIG. 40.
Figure 46:
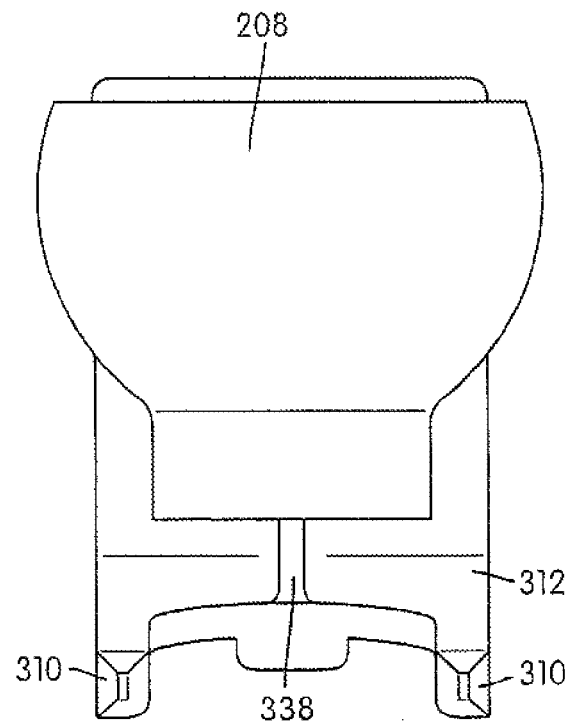
FIG. 46 shows a front elevational view of a connecting bracket of the head mount adjustment mechanism of FIG. 40.
Figure 47:
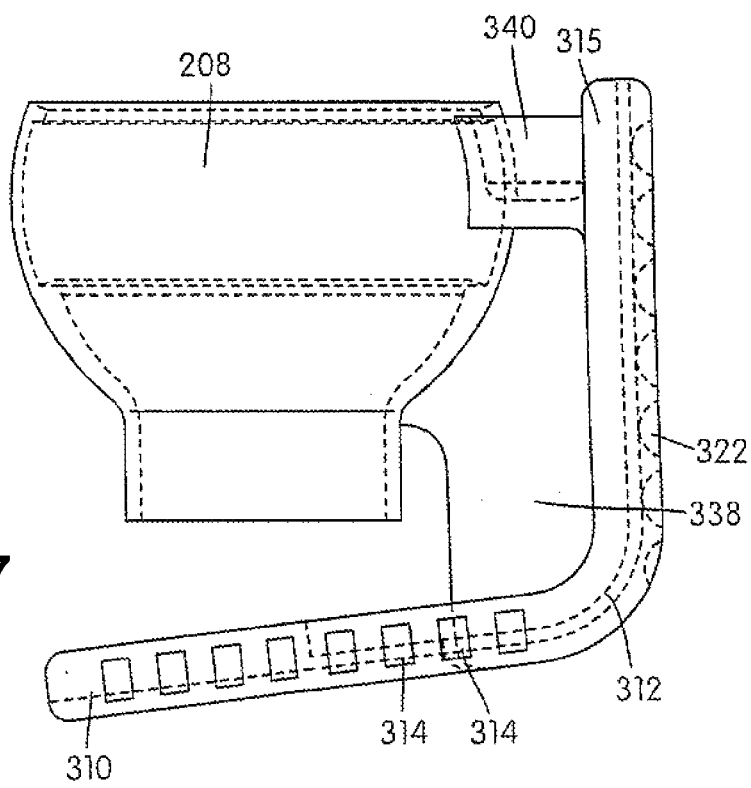
FIG. 47 shows a side elevational view of the connecting bracket of FIG. 46.
Figure 48:
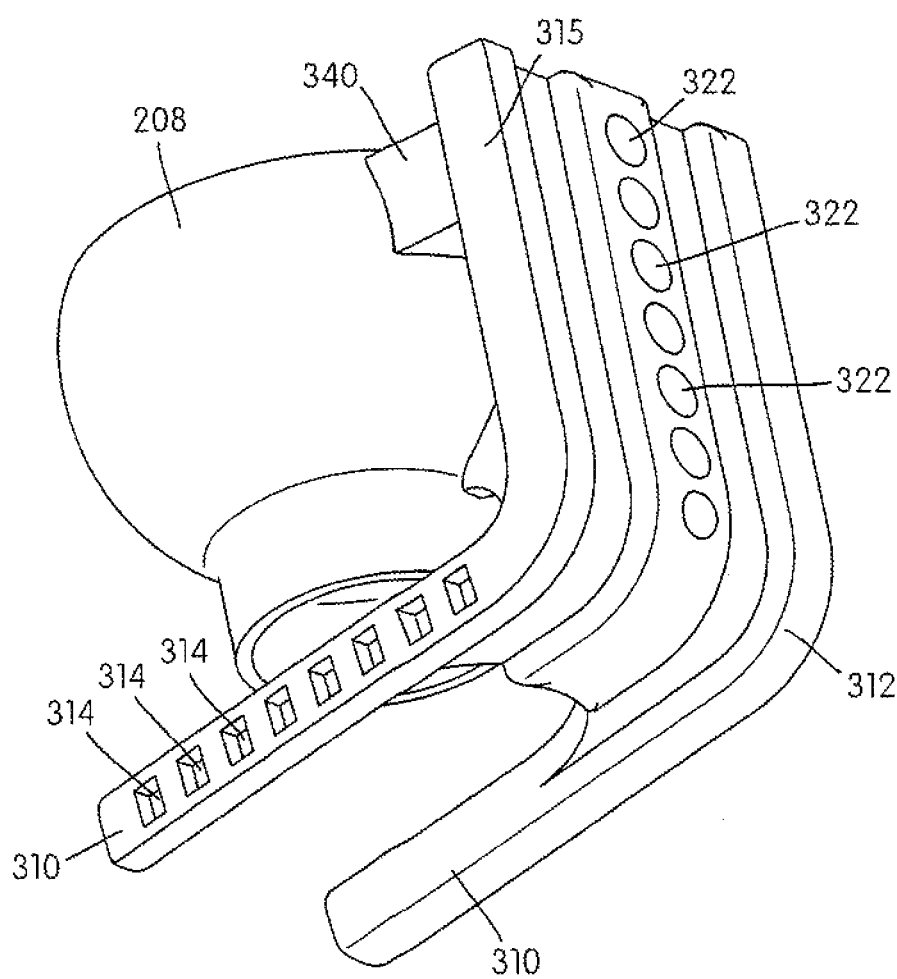
FIG. 48 shows a rear perspective view of the connecting bracket of FIG. 46.
Figure 49:
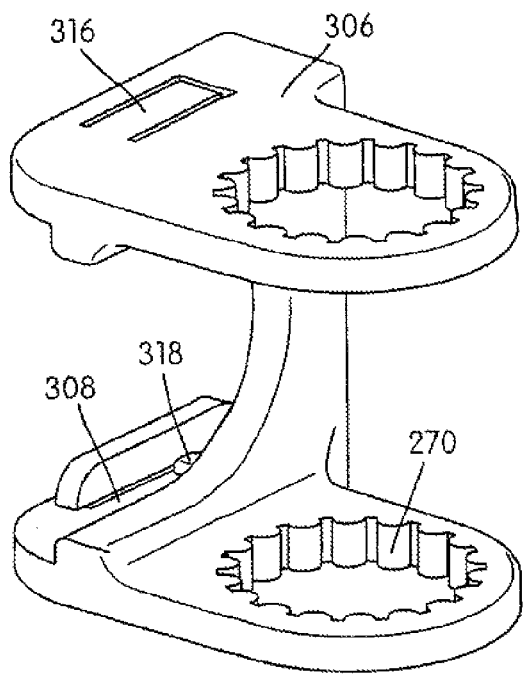
FIG. 49 shows a front perspective view of a locking bracket of the head mount adjustment mechanism of FIG. 40.
Figures 50, 51:
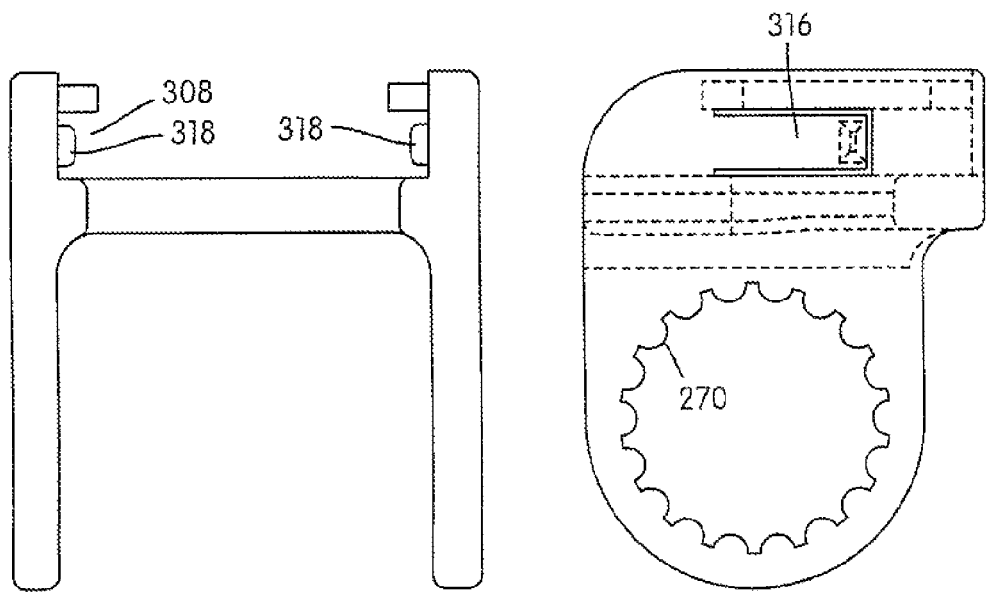
FIG. 50 shows a front elevational view of the locking bracket of FIG. 49.
FIG. 51 shows a side elevational view of the locking bracket of FIG. 49.

In FIG. 44, a socket portion 208 of a ball and socket joint 200 described above is connected to the second extending tab 315 of the connecting bracket 312 by a connecting flange 340 and is interconnected between the first extending tab 310 and the second extending tab 315 with a support flange 338 to provide stability to the socket 208.

The embodiments shown in FIGS. 31-51 may also be configured such that no portion of the mask assembly contacts the user's forehead, similarly to the embodiments of FIGS. 22-29 and FIGS. 59-67 described above.

Alternative Mask Assembly

Figure 52:
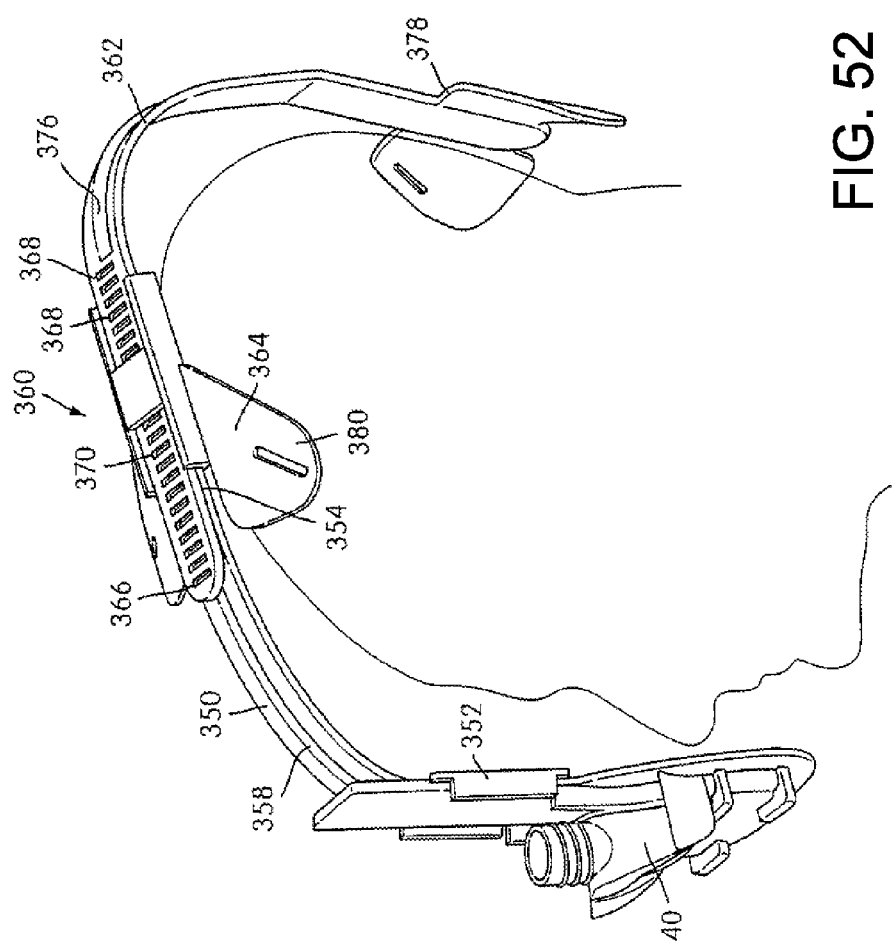
FIG. 52 shows a perspective view of an alternative embodiment of the mask assembly of the present invention.
Figure 53:
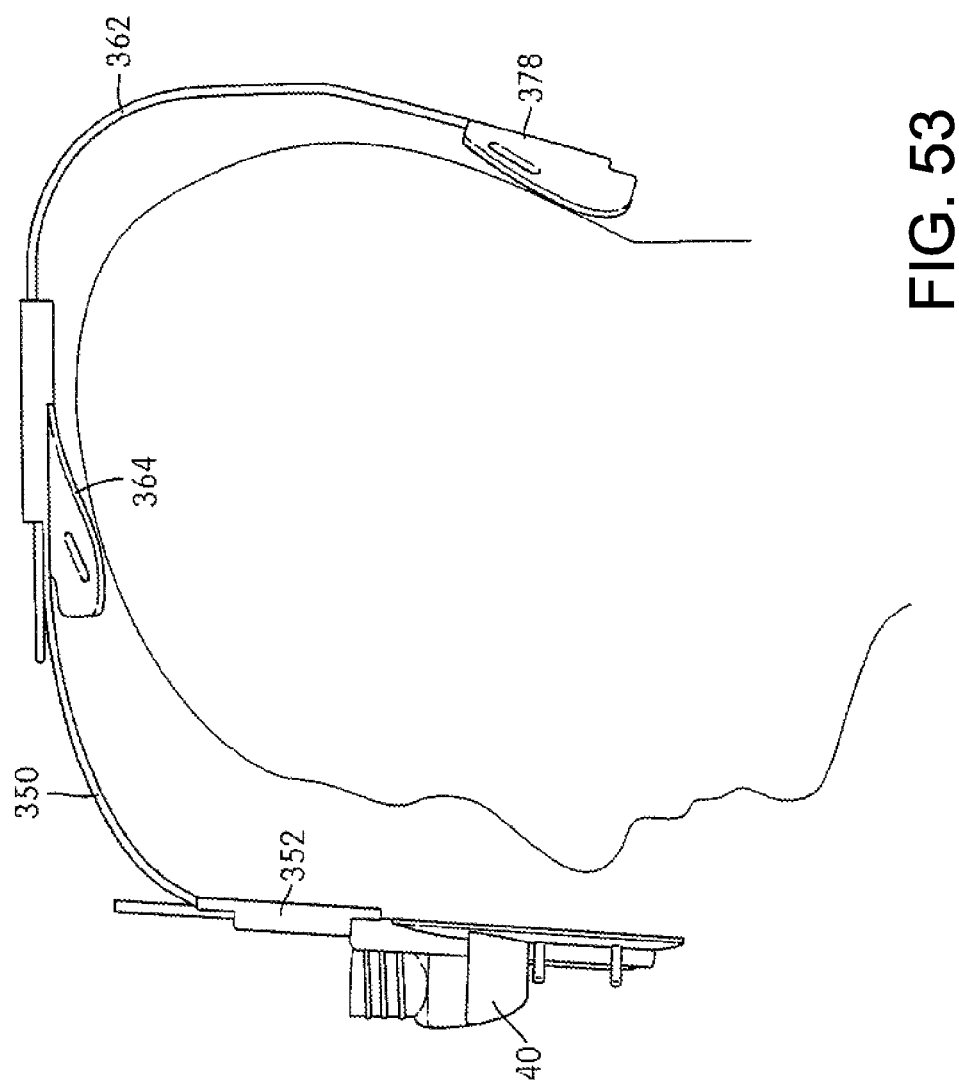
FIG. 53 shows a side elevational view of the mask assembly of FIG. 52.

FIGS. 52 and 53 show an alternative embodiment of the mask assembly 10. This embodiment uses a shell 40 similar to the shell 40—shown in FIGS. 22-27. In FIG. 52, a head strap assembly 360 includes a front head strap 350 which includes a retaining channel 352 adapted to slidingly engage the extension bracket 220 of the shell 40 in the same manner as does the head strap 224 discussed above with respect to FIGS. 22-27. The head strap assembly 360 further includes a rear head strap 362 and a crown mount 364 that interconnects the front and rear head straps. The rear head strap 362 includes a distal portion 366 having a plurality of spaced apart detent slots 368 positioned on an upper surface thereof and a strengthening groove 376 extending along a length thereof. The rear head strap also includes a rear mounting plate 378 for engaging a rear portion of the user's head and attaching to a retaining harness. The front head strap 350 similarly includes a distal portion 354 having a plurality of spaced apart detent slots 356 positioned on a lower surface thereof and a strengthening groove 358 extending along a length thereof.

The crown mount 364 includes a retaining channel 370 adapted to simultaneously receive and engage the distal portions of both the front head strap 350 and the rear head strap 362. The lower surface of rear head strap 362 and upper surface of front head strap 350 are smooth so as to be readily movable over one another when both head straps are inserted in the retaining channel 370. The retaining channel 370 includes a first detent projection 372 projecting downward to selectively engage the detent slots 368 of the rear head strap 362. The retaining channel 370 also includes a second detent projection 374 projecting upward to selectively engage the detent slots 356 of the front head strap 350. The crown mount 364 further includes a mounting plate 380 for engaging a top portion of a user's head and attaching to the retaining harness.

With the structure depicted in FIGS. 52 and 53, the front head strap 350, rear head strap 362 and the crown mount 364 are all adjustable with respect to one another to adjust the extending lengths of both head straps as well as the positioning of the crown mount atop the user's head.

Alternative Latching Mechanism

Figure 54:
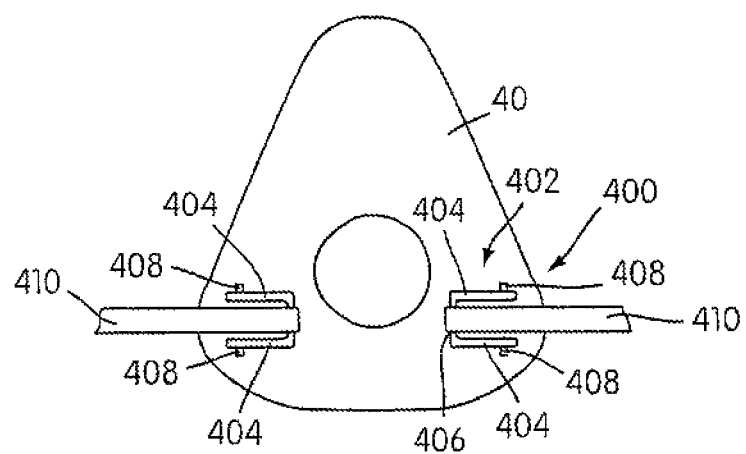
FIG. 54 shows a front elevational view of an alternative embodiment of a latching mechanism of the present invention.
Figure 55:
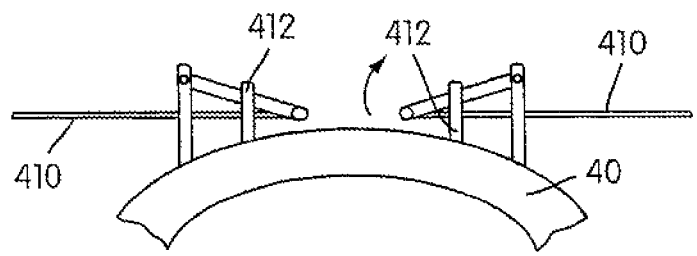
FIG. 55 shows a bottom elevational view of the latching mechanism of FIG. 54 with the latching mechanism in a closed position.
Figure 56:
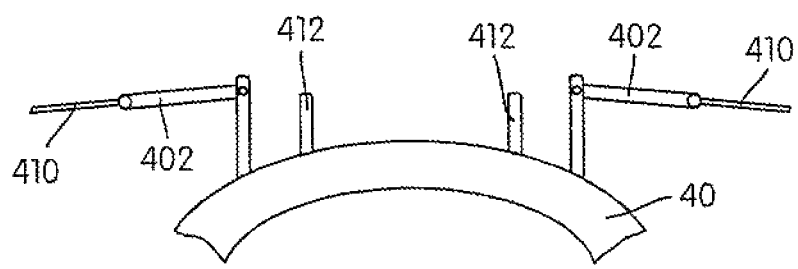
FIG. 56 shows a bottom elevational view of the latching mechanism of FIG. 54 with the latching mechanism in an open position.

FIGS. 54-58 disclose alternative embodiments of the latching mechanism discussed above. The latching mechanism 400 shown in FIGS. 54-56 is a simplified version of the latching mechanism 60 discussed above. In FIGS. 54-58, each latching mechanism 400 includes a unitary link 402 having a pair of link arms 404 interconnected by a transverse shaft 406. Each link arm 404 includes a pivot pin 408 adapted for pivotal engagement in bores in the shell, as with the latching mechanism 60. A harness strap 410 is connected to each shaft 406. The link 402 can be pivoted about the pins 404 between a latched position as depicted in FIGS. 54 and 55 where slack in the harness is taken up by the latching mechanism and an unlatched position as depicted in FIG. 56 where the harness strap 410 is loosened. This embodiment does not include the clip 88 of latching mechanism 60 but otherwise operates in the same manner as the latching mechanism 60. Positive stops 412 may be provided on the shell 40 to stop movement of the latching mechanism in the latched position. In the preferred embodiment, the stops 412 are positioned inward from the shaft 406 so that the shaft end of the link 402 hangs free and can be manipulated by a finger to unlatch the mechanism. In an alternative embodiment, a lever mechanism can be installed on the mask to unlatch both latching mechanisms 400 simultaneously. A latching mechanism may also be used on any other straps connecting to the shell 40.

Figure 57:
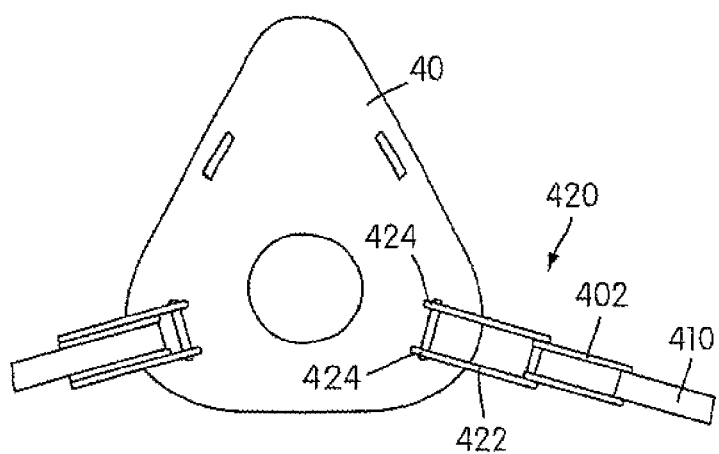
FIG. 57 shows a front elevational view of an alternative embodiment of a latching mechanism of the present invention.
Figure 58:
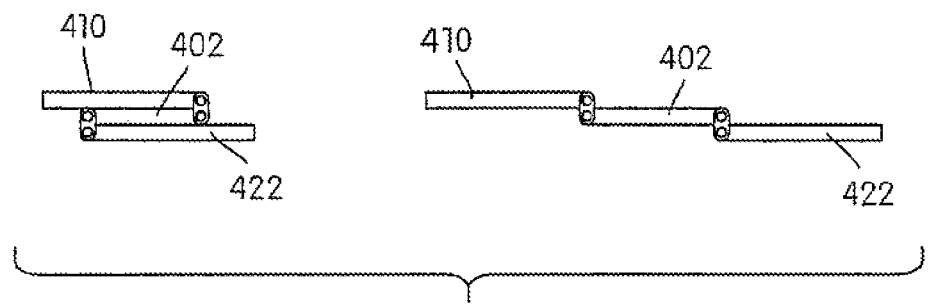
FIG. 58 shows a bottom elevational view of the latching mechanism of FIG. 57 with the latching mechanism in closed and open positions.

In FIG. 57, the latching mechanism 420 is similar to the latching mechanism 400 but includes an extension link 422 that interconnects the link 402 with the shell 40. The extension link 422 includes a pair of hooks 424 for connecting to the shell 40 and while the extension link can pivot somewhat with respect to the shell 40, it does not pivot between a latched position and an unlatched position as does the link 402. This latching mechanism 420 otherwise operates in the same manner as latching mechanism 400 discussed above.

Cushion Connecting Mechanism

A further aspect of the mask assembly of the present invention is a connecting mechanism for connecting the cushion 30 to the shell 40. In many known masks, the cushion is provided with a lip around its shell side periphery which engages a flange running around a cushion side periphery of the shell. The cushion lip can be either single sided, wherein it engages an outer edge or an inner edge of the shell flange, or it can be double sided, wherein it engages both sides of the shell flange. While such a mechanism is effective in retaining the cushion to the shell, it can require finger strength and dexterity to assemble and disassemble the cushion/shell assembly. Since the shell and cushion should preferably be disassembled periodically for cleaning, it is desirable to provide a connection mechanism between the cushion and the mask that is easier to assemble and disassemble. This is especially important where the user may lack finger strength and/or dexterity due to injury, impairment or advanced age.

Figure 65:
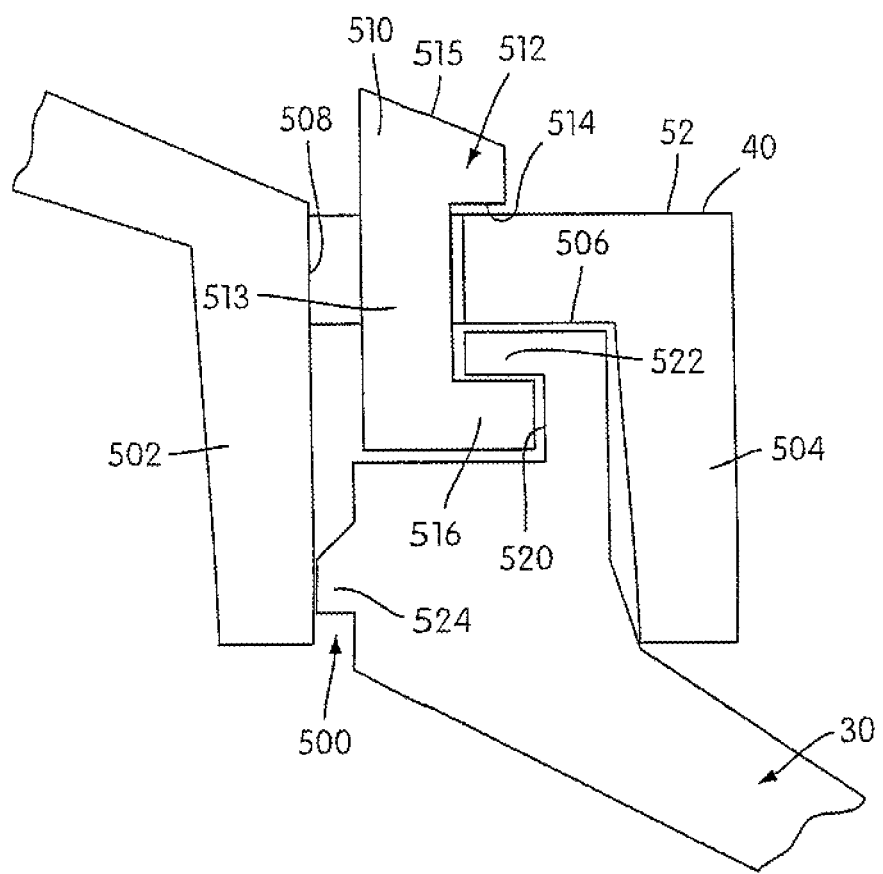
FIG. 65 shows a sectional view of the mechanism used to secure the cushion to the shell.

An improved cushion/shell connection mechanism is shown in FIG. 65, with reference to FIGS. 1 and 9A. The shell 40 of the present invention includes a channel 500 running around a cushion side periphery. The channel 500 is surrounded by an inner wall 502, an outer wall 504 and a channel floor 506 formed by the surface 52 of shell 40. The channel 500 is configured in the generally triangular shape of the shell 40 or any other suitable shape and is preferably wide enough that the cushion can be inserted in the channel without rubbing against the side walls of the channel. See FIG. 9A. The channel 500 includes two slots 508 that pass through the channel floor 506 to allow access to the surface 52 of the shell 40.

The mechanism includes a retaining ring 510 configured to have a similar general shape as the channel 500. The retaining ring 510 has two clips 512 positioned on two respective spring arms 513. The clips 512 are positioned and configured to pass through the respective slots 508 such that an underside lip 514 of each clip engages the surface 52 or a suitable section on shell 40 when the retaining ring 510 is positioned in the channel 500. An upper surface 515 of each clip 512 is beveled to provide easier passage through the slot 508 upon assembly. While only two slots 508 and clips 512 are shown, the mechanism may have a different number of such components. The retaining ring 510 has a cushion retaining lip 516 that runs around a periphery of the retaining ring 510 and extends outward from a bottom portion of the retaining ring 510.

The cushion 30 includes a retaining channel 520 and a retaining lip 522 extending outward from the channel 520. The retaining channel 520 and retaining lip 522 are configured to snugly engage the cushion retaining lip 516 of the retaining ring 510 when the cushion 30 is installed on the retaining ring 510. The cushion 30 also includes a sealing lip 524 that extends from the cushion 30 to engage the channel 500 or other portion of the shell 40 around an entire periphery of the cushion 30 to provide a continuous airtight seal between the cushion 30 and the shell 40. In the embodiment shown in FIG. 65, the sealing lip 524 engages an outer surface of the inner wall 502, i.e., the surface forming a portion of the channel 500. In alternative embodiments, the sealing lip 524 may also be configured to sealingly engage a top surface of the inner wall 502 and/or an inner surface of the wall 502.

To assemble the cushion 30 to the shell 40, the cushion is first mounted on the retaining ring 510 by engaging the channel 520 and lip 522 with the retaining lip 526 around the periphery of the lip 526. This procedure requires some finger strength and dexterity, but it has been found that the required strength and dexterity is less than for assembling the known cushions and shells together. Alternatively, this assembly step can be performed at the factory prior to shipment of the cushion or the cushion 30 can be integrally molded to the retaining ring 510. Next, the assembled retaining ring/cushion assembly is placed in the channel 500 such that the retaining clips 512 align with their respective slots 508 and the retaining ring/cushion assembly is pressed toward the shell 40 such that the spring arms 513 bend back slightly to allow the clips 512 to pass through the slots 508. Once the clips 512 clear the slots 508, the spring arms 513 will spring back, engaging the surfaces 514 of the clips 512 with the surface 52 of the shell 40 and retaining the cushion 30 to the shell 40. This clamps the lip 522 of the cushion 30 to the channel floor 506 and engages the sealing lip 524 with the inner wall to provide a secure, sealed connection between the cushion 30 and the shell 40.

To disassemble the cushion 30 from the shell 40, the user need only press the two clips 512 toward one another until they are no longer engaging the surface 52 such that the clips 512 can pass back through the slots 508. In this regard, it is preferable to have only two clips 512 positioned across from one another with a sufficiently small distance therebetween such that the user can grasp both clips 512 between the thumb and forefinger of one hand so that disassembly is a one-handed procedure. In this manner, the cushion/retaining ring assembly can easily be disassembled from the shell 40 for cleaning or other purposes. Although not necessary, the cushion 30 can also be disassembled from the retaining ring 510 for cleaning.

In a preferred embodiment, the retaining ring is made of acetal, although other materials can be used. Further, the channel 500 and/or retaining ring 510 may be provided with a keyway feature for assisting in the alignment of the retaining ring 510 with the shell 40 upon assembly.

While subassembly between cushion 30 and retaining ring 510 that engages two parts internally through retaining channel 520 and retaining lip 522 is shown, in alternative embodiments, the retaining ring 510 can be subassembled to cushion 30 externally through outer or top walls of the cushion with suitable channel and lip arrangements.

Figure 72:
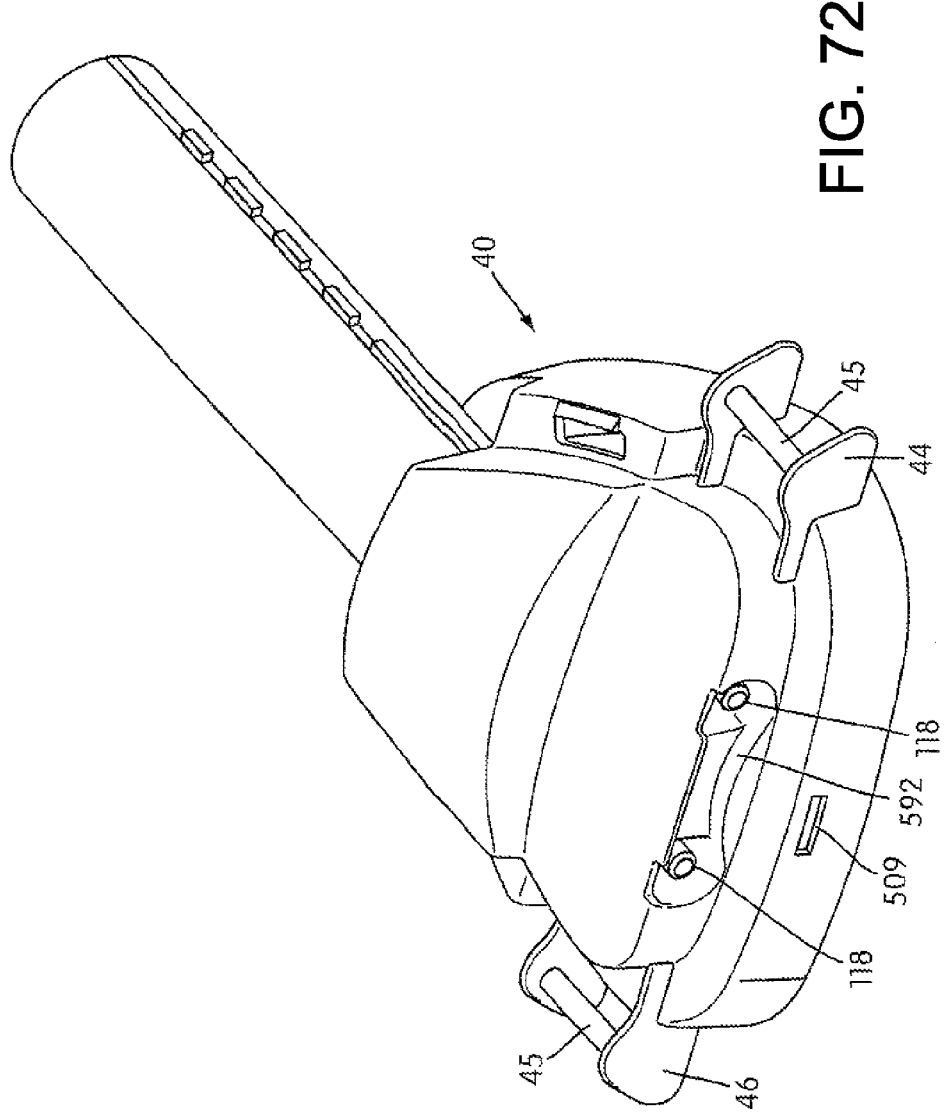
FIG. 72 shows a front perspective view of a mask shell of the embodiment of FIG. 68.
Figure 73:
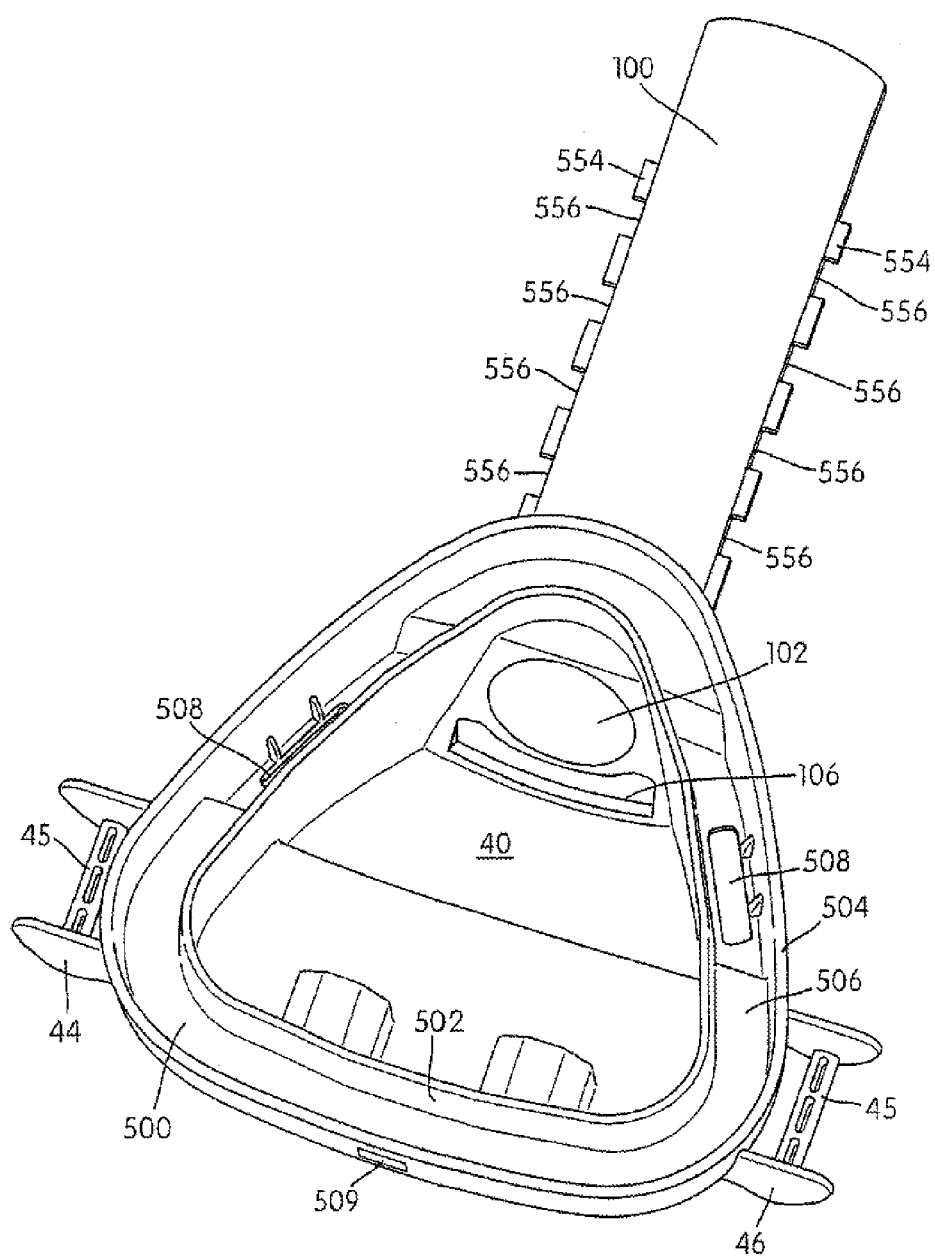
FIG. 73 shows a rear perspective view of the mask shell of the embodiment of FIG. 68.

FIGS. 68-89 illustrate an alternative embodiment of the mask assembly 10 of the present invention utilizing a single latching mechanism 60 similar to the latching mechanism shown in FIGS. 62-64. The mask assembly includes a shell 40 and a cushion 30. In FIGS. 72 and 73, the shell 40 includes a pair of flanges assemblies 44 and 46. Each flange assembly 44 and 46 includes an integrally molded pivot pin 45, with the two pivot pins 45 being generally parallel to one another in a preferred embodiment.

Figure 76:
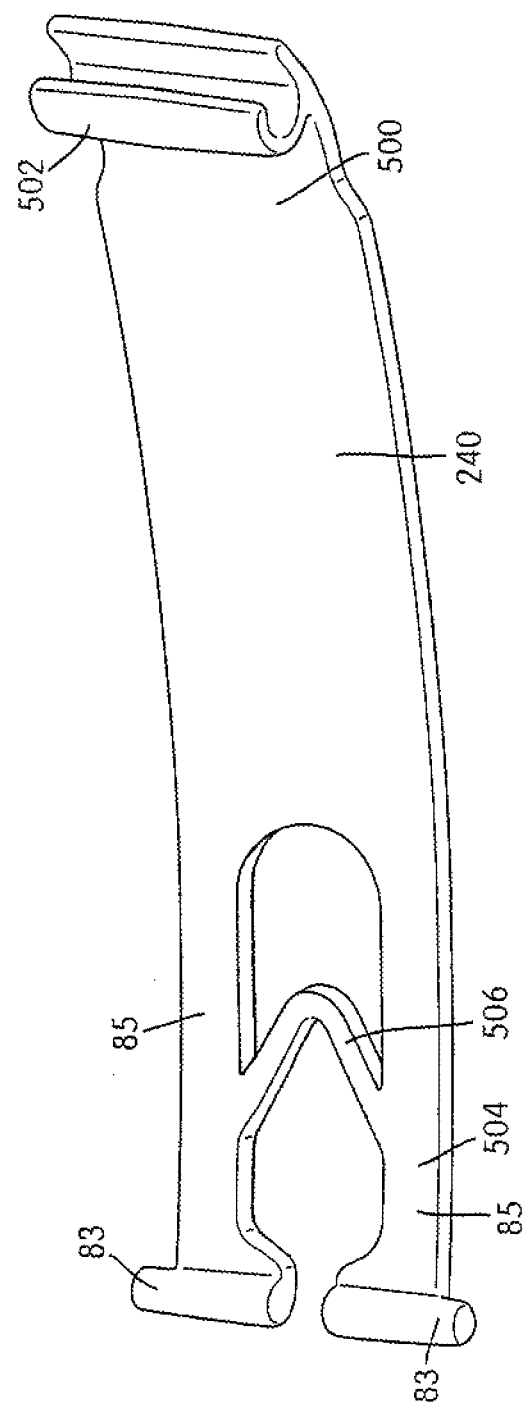
FIG. 76 shows a rear perspective view of a clip link of a latching mechanism of the embodiment of FIG. 68.
Figure 79:
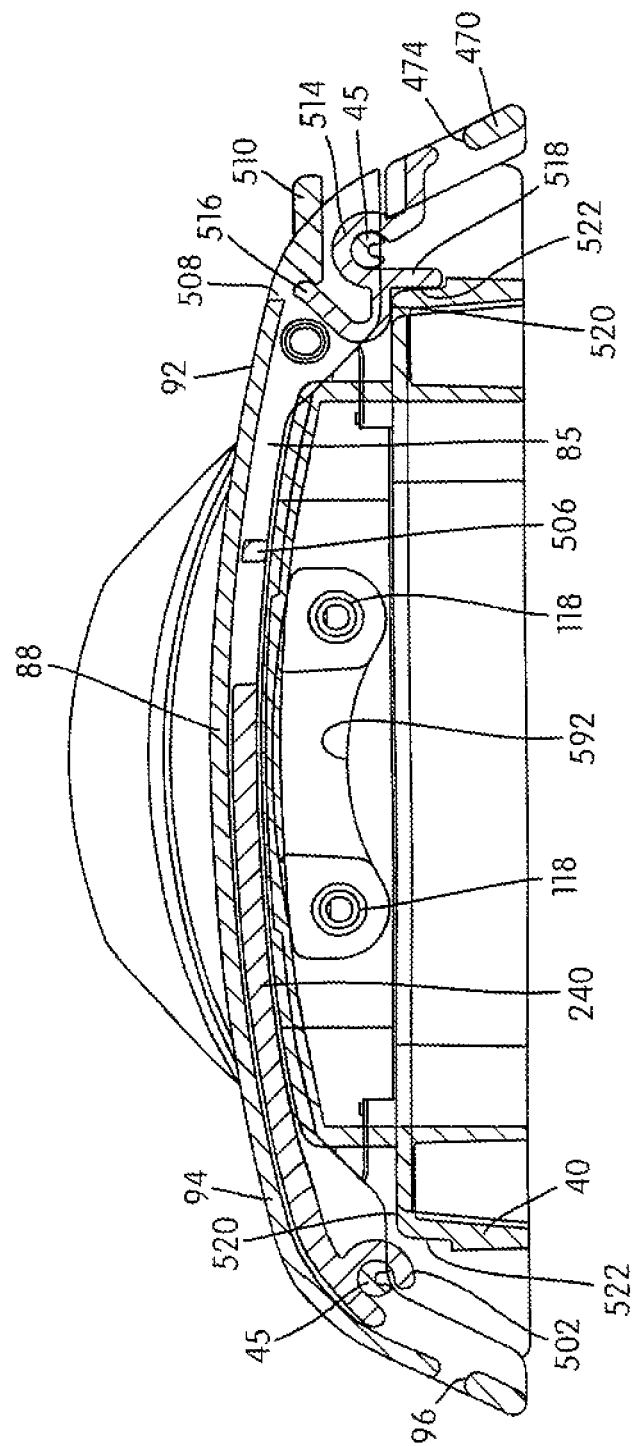
FIG. 79 shows a sectional view of the latching mechanism and mask shell of the embodiment of FIG. 68.

In FIGS. 79 and 76, the latching mechanism 60 further includes a clip 88 and a clip link 240. The clip link 240 includes a first end 500 having a gripping mechanism 502 adapted for fitting over and grasping one of the selected pins 45 to pivotally attach the clip link 240 to the shell 40. The clip link 240 further includes a second end 504 having a pair of pins 83 for engaging bores 92 in a first end 90 of clip 88 to pivotally attach the clip 88 to the clip link 240. The pins 83 are mounted on pin arms 85 extending away from a central portion of the clip link 240 to provide a spring action so that they can be flexed toward each other for inserting the pins 83 into the bores 92 of the clip 88. A spring member 506 interconnects the two pin arms 85 to provide additional spring force to the pin arms 85, as well as to provide lateral stability to the pin arms 85 to resist twisting of the clip link 240. The effective spring force on the pin arms 85 can be varied as desired by altering the size and length of the pin arms 85 and/or the size and positioning of the spring member 506.

Figure 68:
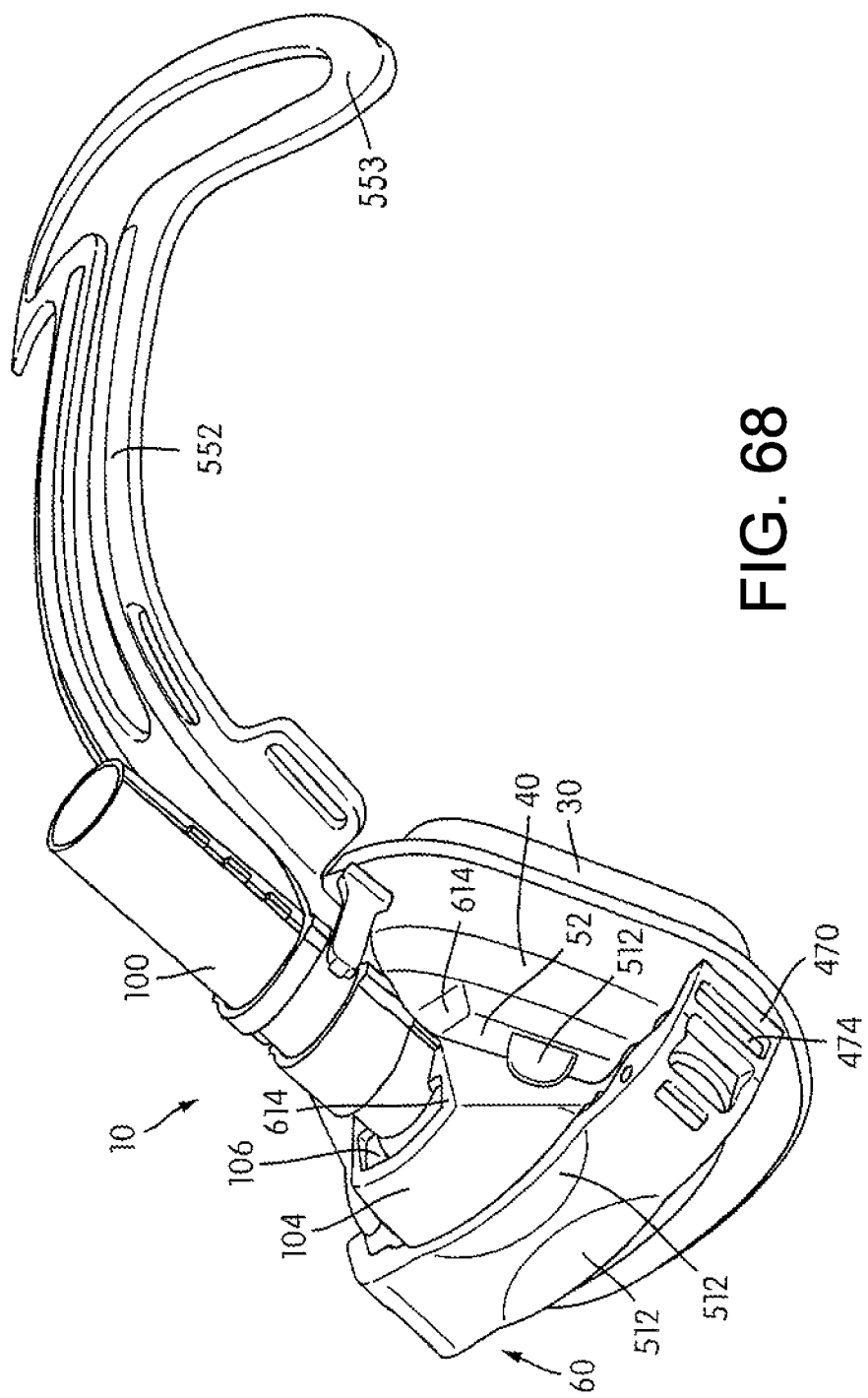
FIG. 68 shows a perspective view of an alternative embodiment of the mask assembly of the present invention.
Figure 69:
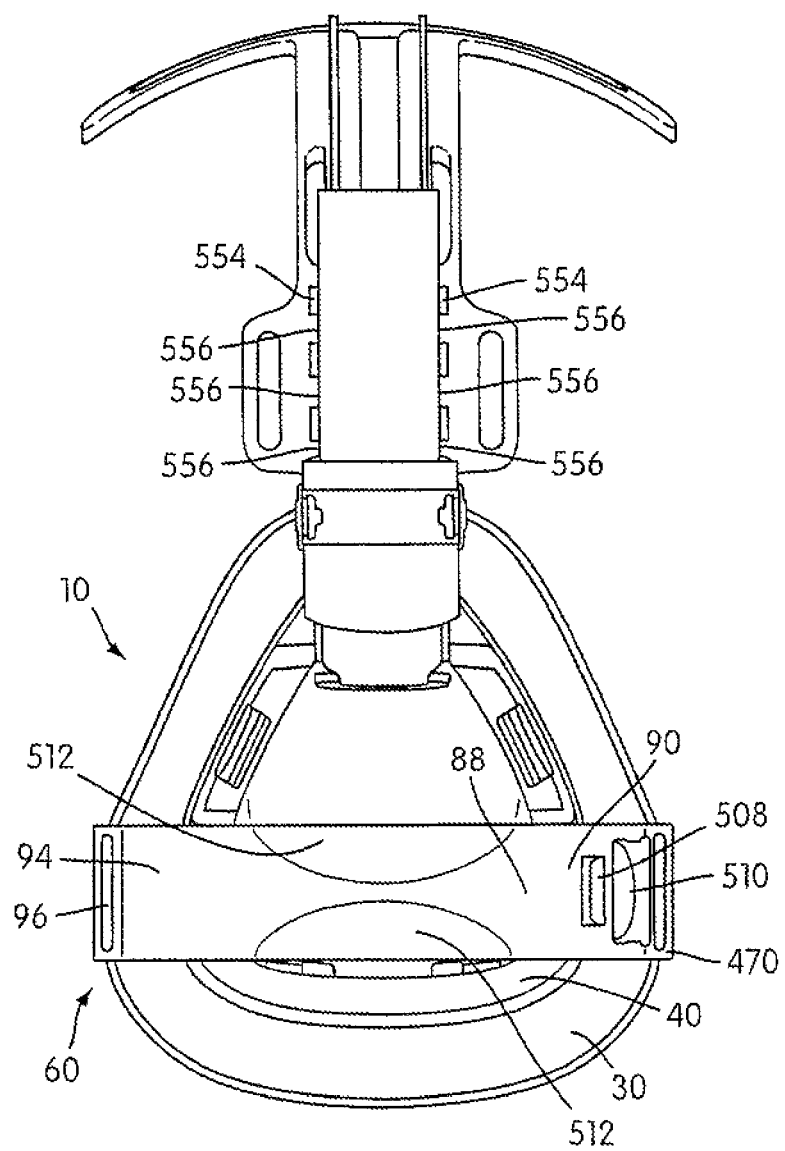
FIG. 69 shows a front elevational view of the embodiment of FIG. 68.
Figure 70:
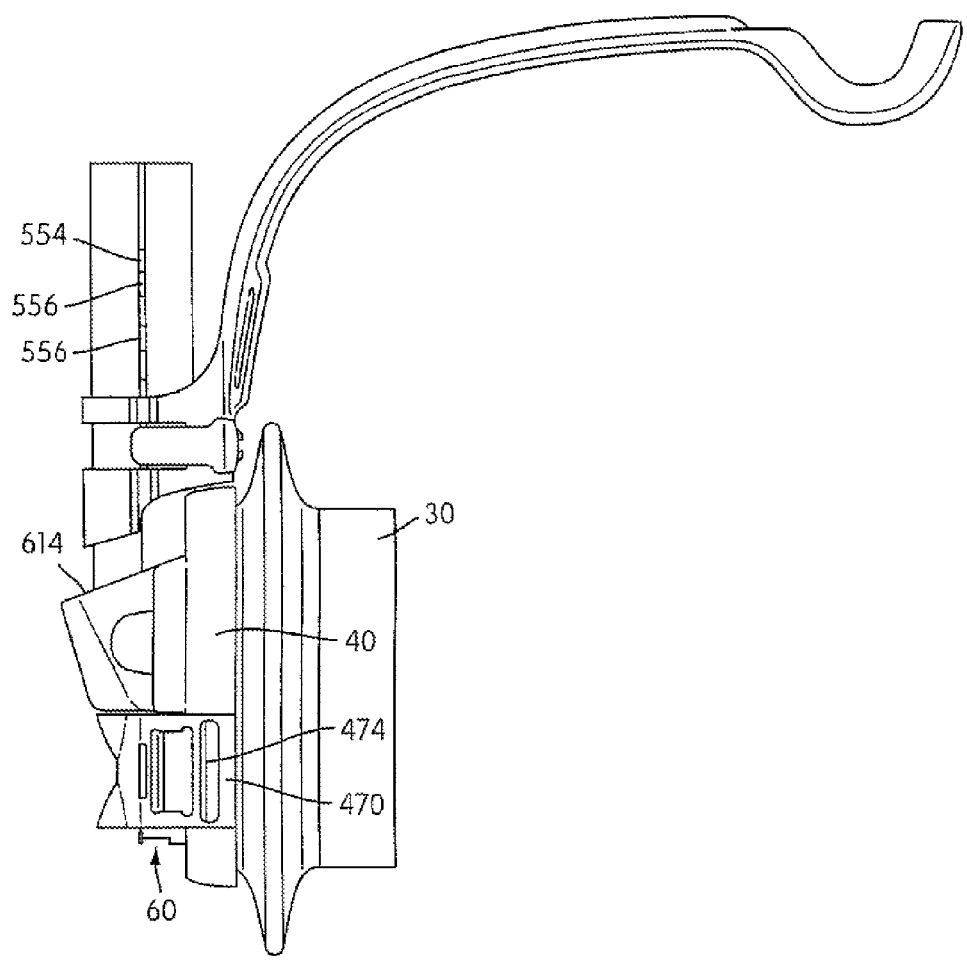
FIG. 70 shows a side elevational view of the embodiment of FIG. 68.
Figure 71:
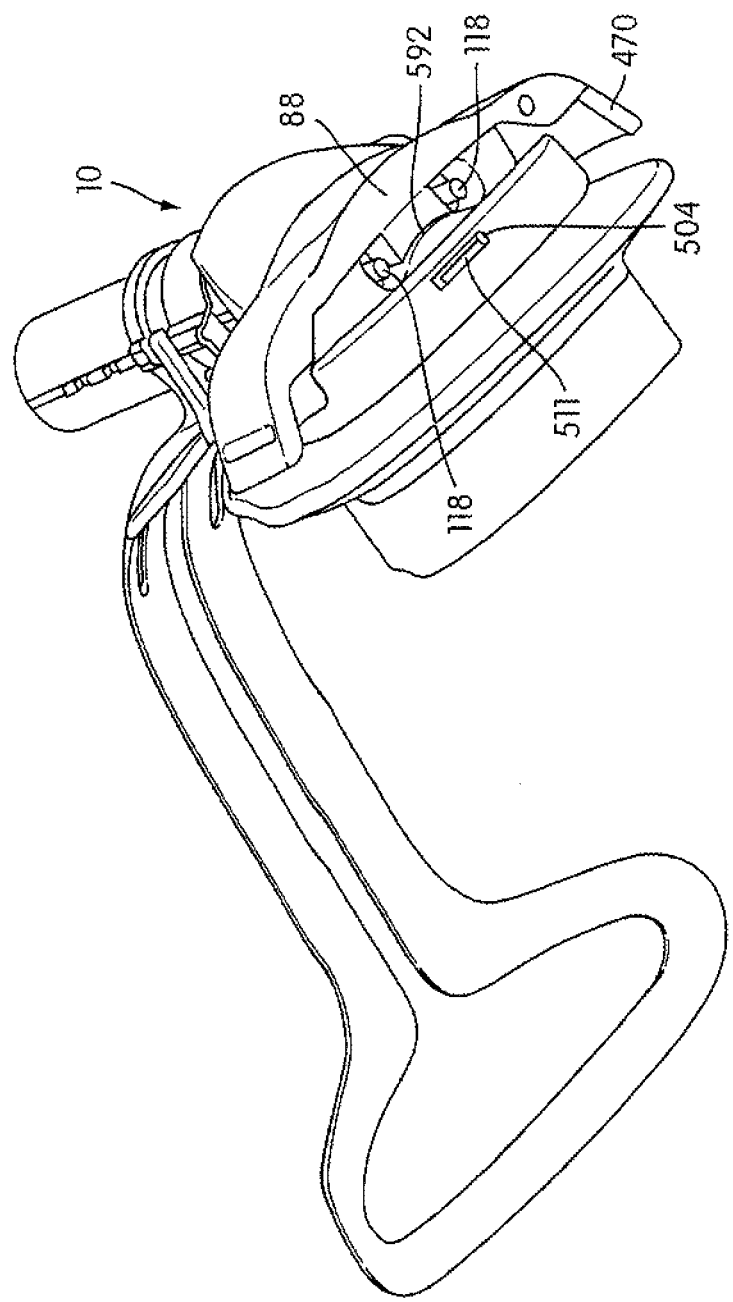
FIG. 71 shows a bottom perspective view of the embodiment of FIG. 68.

The clip 88 also includes a second end 94 having a mask harness-engaging portion 96 in the form of a transverse slot. The first end 90 includes a locking slot 508, discussed below, and a lifting member 510 for engagement and lifting by the user to unlatch the latching mechanism 60. Since the clip link 240 can be mounted on either of the pins 45, the latching mechanism 60 is reversible on the mask assembly 10 for easy manipulation by either right or left handed users. The latching mechanism 60 operates in the same manner as the embodiment shown in FIGS. 62-64, pivoting about the pin 45 when unlatched to an open position that releases tension on the harness. In FIGS. 68 and 69, the clip 88 includes can include a pair of opposing ornamental raised portions 512 for providing a smooth, aesthetic transition between the clip 88 and the shell 40, regardless of whether the latching mechanism 60 is mounted on the left or right side of the shell 40.

Figure 77:
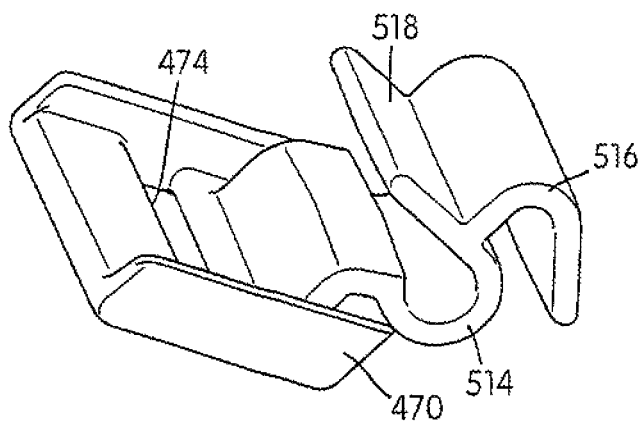
FIG. 77 shows a rear perspective view of a harness engaging clip of a latching mechanism of the embodiment of FIG. 68.
Figure 78:
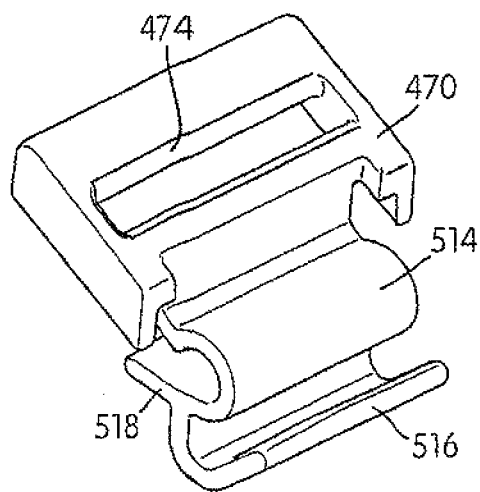
FIG. 78 shows a front perspective view of a harness engaging clip of a latching mechanism of the embodiment of FIG. 68.

In FIGS. 77 and 78, the latching mechanism 60 also includes a harness engaging clip 470. The harness engaging portion 470 includes a gripping mechanism 514 adapted for fitting over and grasping the other of the pins 45 to attach the harness engaging clip 470 to the shell 40. The harness engaging clip 470 also includes a mask harness engaging portion 474 in the form of a transverse slot, a locking tab 516 and a stop tab 518. In this embodiment, the harness engaging clip 470 is not intended to pivot about the pin 45. This is accomplished by engagement of the locking tab 516 and stop tab 518 with adjacent surfaces 520 and 522, respectively, of shell 40 when the clip 470 is mounted over the desired pin 45. In FIG. 79, the harness engaging clip 470 cannot pivot about the pin 45 and must be installed over the pin 45 by use of a generally vertical movement of the clip 470 downward over the pin 45. The locking tab 516 is adapted to engage and disengage the locking slot 508 of the clip 88.

In a preferred embodiment, the locking tab 516 only partially engages the locking slot 508 in the locked position. In this manner, the clip 88 is inhibited from lifting during use, but due to the natural elasticity of the clip 88 and the harness engaging clip 470, the locking engagement can be overcome without pivoting the harness engaging clip to the up position by applying a direct lifting force to the lifting member 510. The amount of lifting force needed to overcome the locking engagement can be varied by altering the extent of engagement between the locking tab 516 and the locking slot 508 and/or the rigidity of the clip 88 and/or the clip 470. The locking tab 516 and a locking engagement surface 524 of the locking slot 508 are angled away from horizontal to allow easier engagement and disengagement of the locking mechanism.

In an alternative embodiment, the stop tab 518 can be removed and the locking tab 516 reconfigured so as not to engage the shell 40 so that the clip 470 can pivot about pin 45. With this alternative configuration, the mechanism can also be locked and unlocked by pivoting locking tab 516 and harness engaging clip 470 about the pin 45 between an unlocked up position (away from the user's face) where the locking tab 516 does not engage the locking slot 508, and a locked down position (toward the user's face) where the locking tab 516 does engage the locking slot 508 and inhibits lifting of the clip 88. In such an embodiment, the harness engaging clip 470 is naturally pulled into the locked down position when the mask assembly 10 is being worn by the tension in the mask harness. In such an embodiment, the locking tab 516 and locking slot 508 can be configured such that the locking engagement cannot be readily overcome unless the harness engaging clip 470 is pivoted to the unlocked up position. In the preferred embodiment, the harness engaging clip 470, clip 88 and clip link 240 are each unitarily molded from a suitable plastic.

Head Support Adjustment Mechanism

Figure 80:
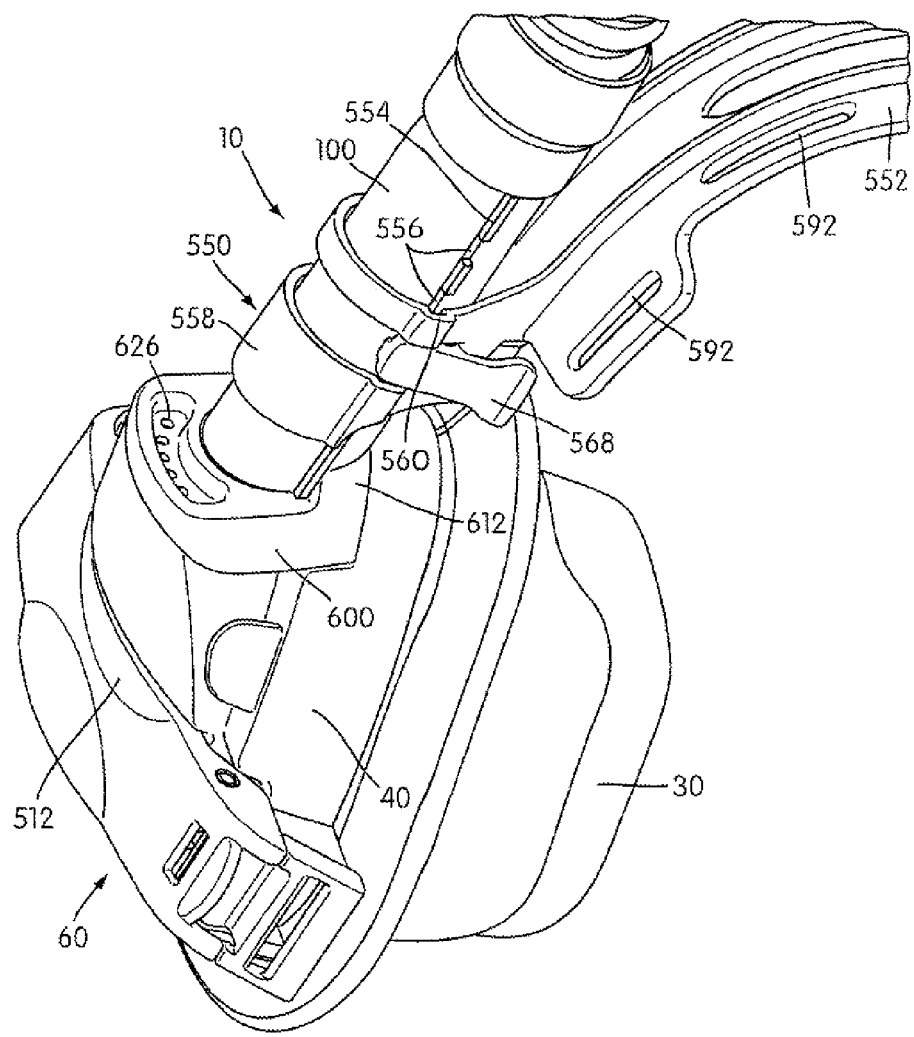
FIG. 80 shows a perspective view of the embodiment of FIG. 68.

In FIG. 80, the mask assembly 10 of this embodiment also includes a head support adjustment mechanism 550 that vertically adjustably mounts a head support 552 to air tube 100 of the shell 40. The head support adjustment mechanism 550 includes a pair of detent portions 554 connected to opposite exterior sides of the air tube 100 and running axially along the air tube 100. The detent portions 554 each include a plurality of slots 556 spaced along the detent portions 554 to define locating positions along the air tube 100 with corresponding pairs of slots 556 of the two detent portions 554 being generally positioned at the same height along the air tube 100.

Figure 83:
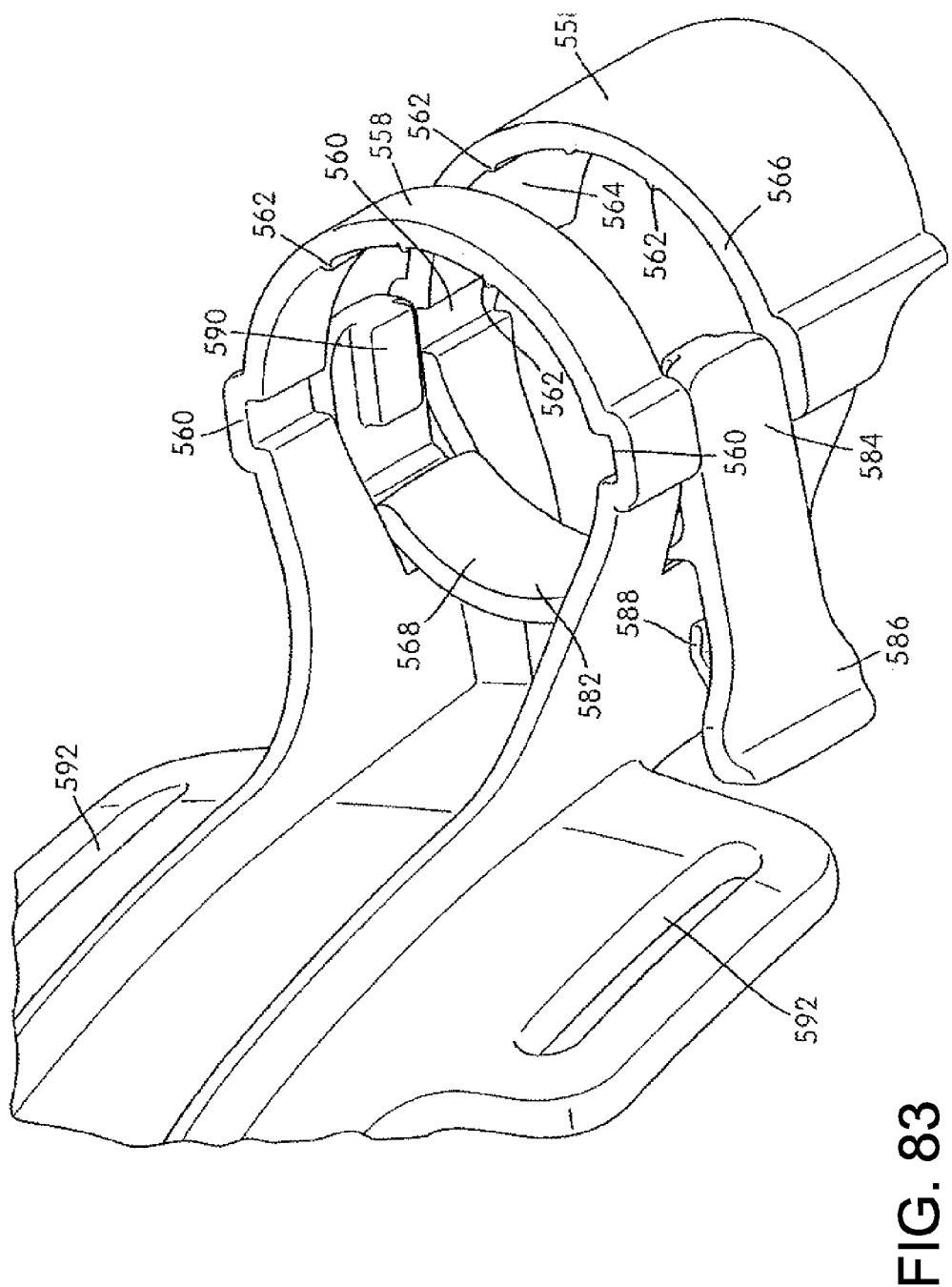
FIG. 83 shows a perspective view of a portion of a head support adjustment mechanism of the embodiment of FIG. 68.

The head support adjustment mechanism 550 also includes a loop portion 558 connected to the head support 552 that is adapted to slideably fit over the air tube 100 and detent portions 554. The fit between the loop portion 558 and the air tube 100 is preferably such that the loop portion 558 can readily slide over the air tube 100 without allowing so much clearance that there is excessive movement and play between the head support 552 and the shell 40 once the head support 552 is adjusted. In FIG. 83, to provide the desired fit without too much clearance, the loop portion 558 includes a pair of slot portions 560 to receive the corresponding detent portions 554. This engagement between the detent portions 554 and the slot portions 560 prevents undesired rotational movement between the loop portion 558/head support 552 and the air tube 100/shell 40. Further, the loop portion 558 includes a plurality of raised ridges 562 running axially along an interior surface 564 of the loop portion 558. These raised ridges 562 contact the air tube 100 and assist in providing the desired fit between the loop portion 558 and the air tube 100 while reducing the amount of friction causing contact area between the loop portion 558 and the air tube 100 that can prevent easy movement of the loop portion 558 along the air tube 100 during adjustment of the adjustment mechanism 550.

Figure 82:
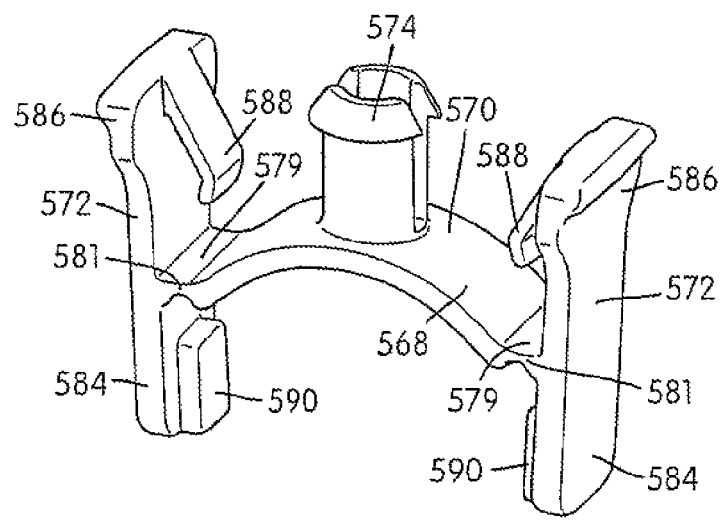
FIG. 82 shows a perspective view of an adjustment clip of a head support adjustment mechanism of the embodiment of FIG. 68.
Figure 84:
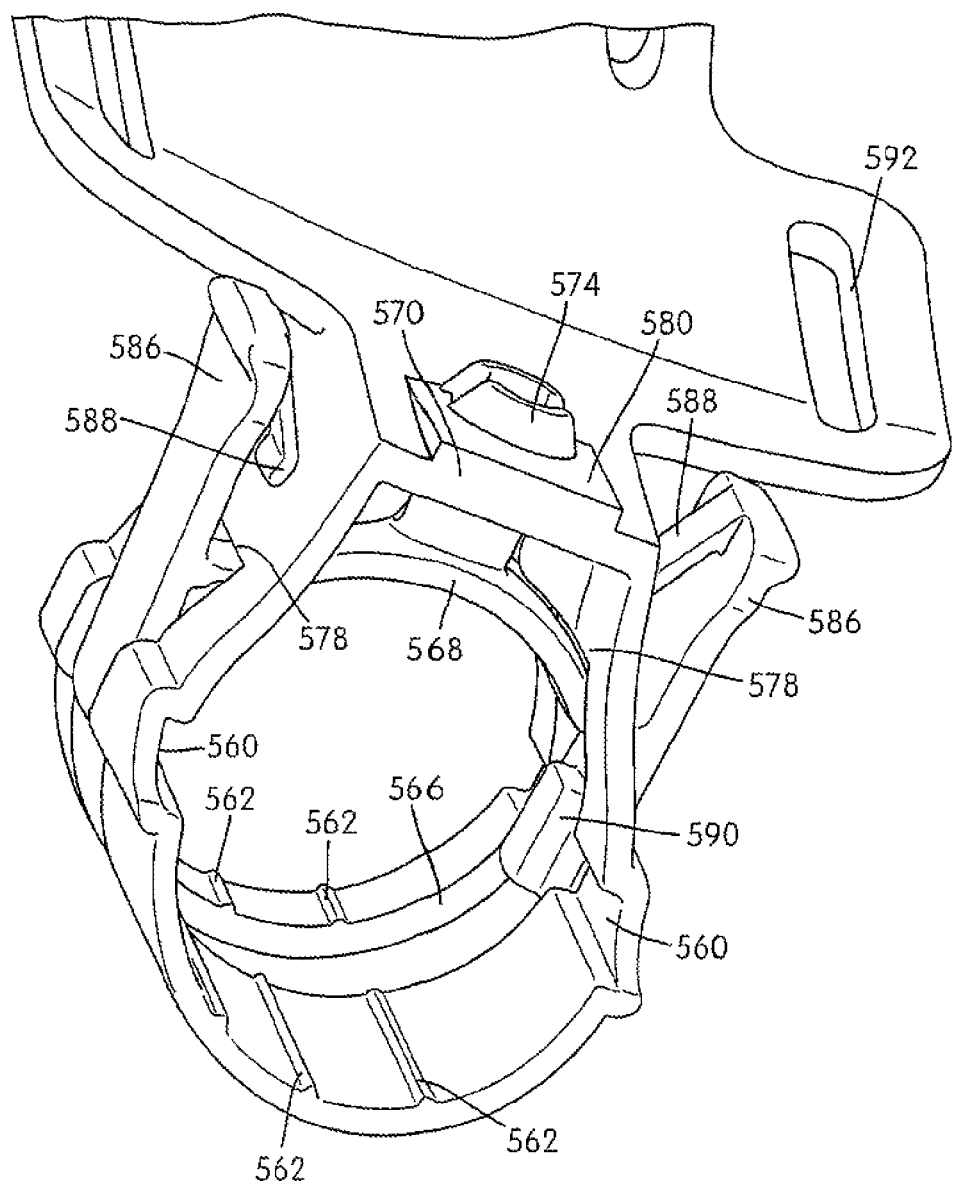
FIG. 84 shows a bottom perspective view of a portion of a head support adjustment mechanism of the embodiment of FIG. 68.
Figure 85:
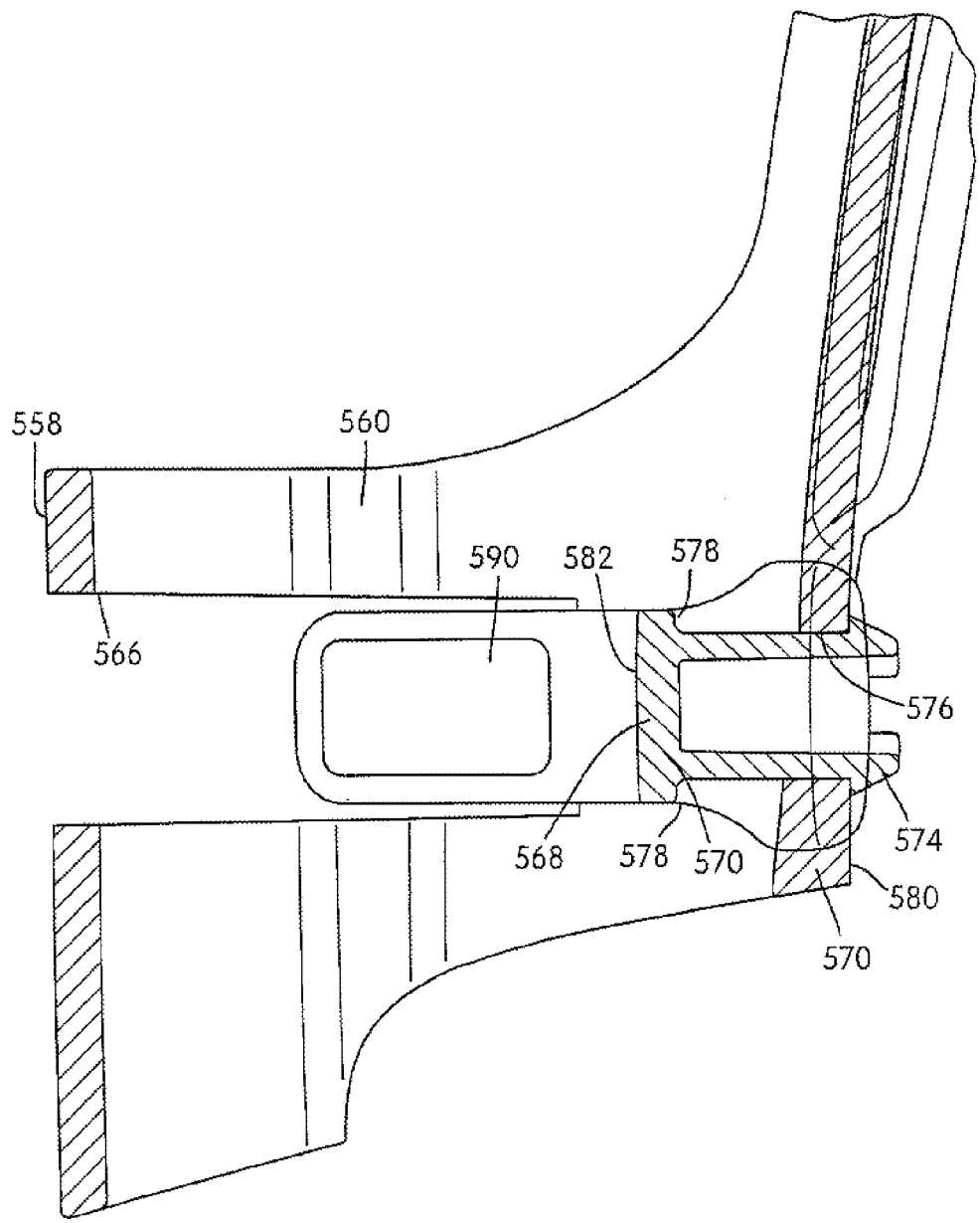
FIG. 85 shows a sectional view of a portion of a head support adjustment mechanism of the embodiment of FIG. 68.

In FIG. 82, the loop portion 558 includes a transverse slot 566 adapted to receive an adjustment clip 568. The adjustment clip 568 includes a semi-circular body 570 interconnecting a pair of spring tabs 572. A split flange projection 574 is mounted to a back side of the semi-circular body 570 for insertion into a bore 576 on a back portion 579 of the loop portion 558 and engagement with an exterior surface 580 of the loop portion 558 to removably mount the adjustment clip 568 to the loop portion 558. In FIG. 84, the transverse slot 566 includes a pair of forward facing shoulders 578 for engaging corresponding outboard rear surfaces 579 of the semi-circular body 570 to stabilize the adjustment clip 568 when it is mounted to the loop portion 558 by means of the projection 574. Upper and lower surfaces of the transverse slot 566 engage upper and lower surfaces of the adjustment clip 568 to provide vertical stability to the adjustment clip 568. The clip 568 and loop portion 558 can alternatively be molded as a single unitary component but the two piece construction described is easier to manufacture. In FIG. 85, a front side 582 of the semi-circular body 570 is adapted to engage a back side of the air tube 100 to provide stability between the air tube 100 and the adjustment clip 568/loop portion 558.

In FIG. 82, each of the spring tabs 572 includes a grasping portion 586 positioned rearward of the body 570 and a detent engagement portion 584 positioned forward of the body 570. In this manner, the body 570 acts as a fulcrum to each spring tab 572 such that when the grasping portions 586 are grasped by the user and pressed together, the detent engagement portions 584 move apart. When the grasping portions 586 are released, the natural spring action of the clip 568 moves the detent engagement portions 584 closer together. The body 570 can be thinned at its outboard edges 581 to increase the flexibility of the spring tabs 572 with respect to the body 570. When the adjustment clip 568 is mounted to the loop portion 558, the grasping portions 586 are positioned outside of the loop portion 558 for manipulation by the user while the detent engagements portions are positioned in the transverse slot 566.

Each grasping portion 586 includes a spring arm 588 mounted thereto for engaging an exterior surface of the loop portion 558 to assist in spring biasing the grasping portions 586 away from each other and the detent engagement portions 584 toward each other. Each detent engagement portion 584 includes an engagement tab 590 sized and adapted to engage corresponding slots 556 of the detent portions 554 to vertically lock the loop portion 558/head support 552 with respect to the air tube 100/shell 40. The positioning of the loop portion 558/head support 552 can be adjusted with respect to the air tube 100/shell 40 by squeezing together the grasping portions 586 to release the engagement tabs 590 from the slot 556, moving the loop portion 558 to the desired position on the air tube 100 and releasing the grasping portions 586 so that the engagement tabs engage the corresponding slots 556 of the detent portions 554. In the embodiment shown, there are four sets of slots 556, and thus, four vertical positions to which the loop portion 558 can be adjusted with respect to the air tube 100. The number of slots can be altered to provide an alternative number of adjustment positions.

Figure 81:
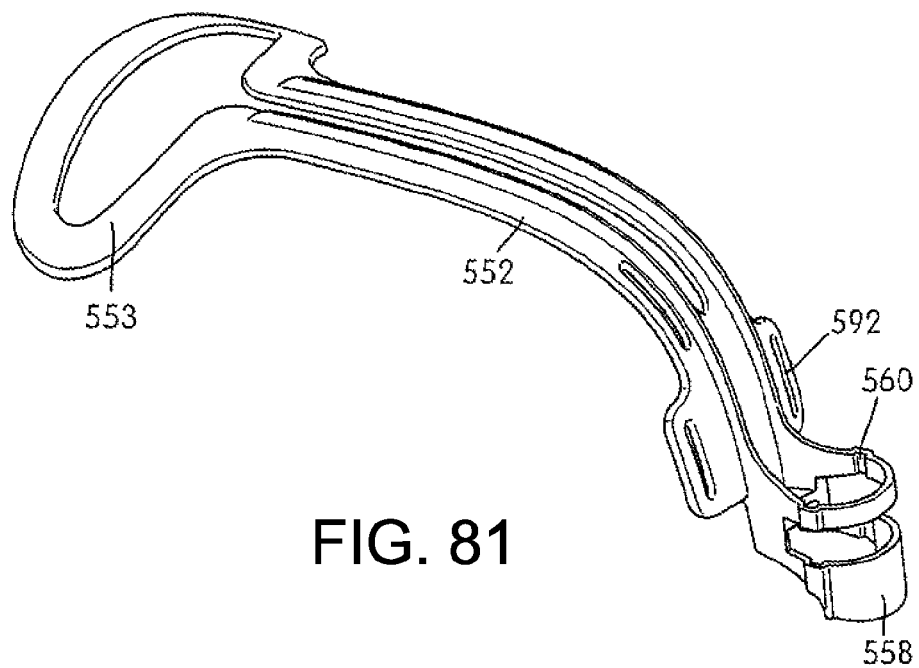
FIG. 81 shows a perspective view of a head support of the embodiment of FIG. 68.

In FIG. 81, the head support 552 includes a plurality of slots 592 or other engagement mechanisms for attaching the head support 552 to a corresponding mask harness and a loop portion 553 for engaging the patient's head and stabilizing the head support 552. Although not shown, the head support 552, especially the loop portion 553, and other components of the mask 10 may be covered in foam, fabric or other soft material to provide a cushioned and more comfortable fit for the patient.

Although the air tube 100 is shown as being aligned generally parallel with a plane of the shell 40, the air tube 100 can be angled backward somewhat toward the user to provide a better alignment for connection to an air supply conduit. It has been found with this embodiment, angling the air tube 100 back by up to 18°, and preferably by about 10°, provides a desired alignment with the air supply conduit and a comfortable fit for the user. Other angles can also be used as the situation warrants.

Exhalation Port

Figure 86:
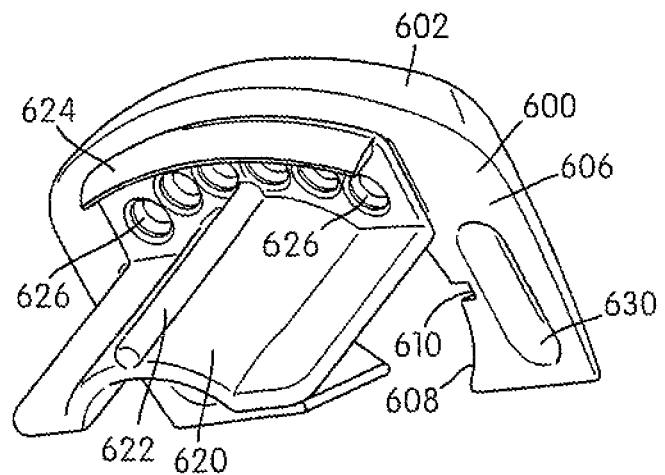
FIG. 86 shows a bottom perspective view of a vent of the embodiment of FIG. 68.
Figure 87:
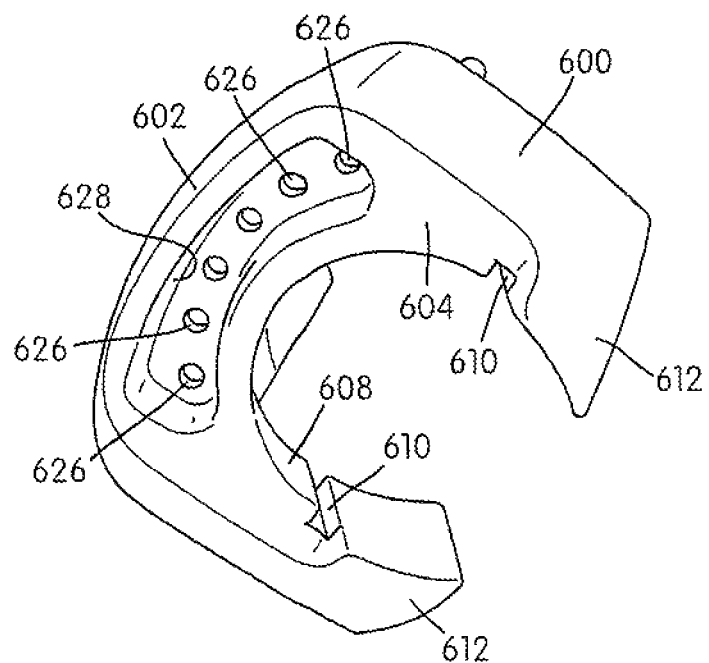
FIG. 87 shows a top perspective view of the vent of FIG. 86.

In FIG. 73, the shell 40 includes a single exhalation port 106 positioned centrally outboard of the intake port 102. Unlike the embodiment shown in FIG. 9B, in this embodiment, there is no exhalation duct, as the exhalation passage in the shell 40 is only as long as the thickness of the shell. An exterior of the exhalation port 106 is directed upwardly and partially surrounding the air tube 100. See FIG. 68. Although the exhalation port 106 can be used alone if sized properly for a desired flow rate, it is preferred that it be used in conjunction with an additional exhalation vent 600 as depicted in FIGS. 86 and 87 or in FIG. 80 showing the vent 600 installed on the shell 40. The vent 600 is generally flexible and preferably molded of silicone, although other materials can be used.

The vent 600 includes a body 602 having an upper surface 604 and a lower surface 606. The body 602 includes a generally semi-circular cutaway 608 configured and sized to receive and grip the air tube 100 to secure the vent 600 to the shell 40. The semi-circular cutaway 608 includes a pair of axially extending slots 610 configured to receive the two detent portion 554 and provide additional gripping force between the vent 600 and the air tube 100. The body 602 also includes a pair of tapered raised wings 612 positioned at outboard ends of the semi-circular cutaway 608 to contact the air tube 100 to provide additional gripping force and an aesthetic transition between the air tube 100 and the shell 40. When installed on the shell 40, the lower surface 606 is adapted to sit on an upwardly facing vent platform 614 of the shell 40.

A baffle 620 is connected to and extends downwardly from the lower surface 606 of the vent 600. The baffle 620 extends into the exhalation port 106 and the interior of the shell 40 to assist in keeping intake and exhaust flows in the mask separate. This reduces cyclic noise and improves the removal of exhaust gas from the mask. The baffle 620 includes an axially extending rib 622 that adds rigidity and strength to the baffle 620. The baffle 620 is shown as having a generally semi-circular cross-section with flat outboard portions but the configuration can be altered as desired for different flow characteristics. In FIG. 86, a flange 624, spaced apart from the baffle 620, also is connected to and extends downwardly from the lower surface 606 of the vent 600. The flange 624 and baffle 620 are configured to contact the interior sides of the exhalation port 106 to correctly position the vent 600 with respect to the shell 40 and exhalation port 106, as well as to help secure the vent 600 to the shell 40.

A plurality of vent apertures 626 are positioned between the baffle 620 and the flange 624 for venting the exhalation gases to the atmosphere. The number of vent apertures 626, and their size and configuration can be altered as desired to achieve different flow properties. However, in a preferred embodiment shown, there are six apertures 626 that each taper along at least a portion of their length from an interior side to an exterior side of the vent 600. That is, the interior side of the vent apertures 626 is larger than the exterior side of the apertures 626. Such a configuration helps reduce noise generated by the exhalation flow.

The length of each vent aperture 626 can affect the flow characteristics of the aperture and is determined by the thickness of the vent body 602 in the region of the vent apertures 626. In order to reduce the length of the vent apertures 626 to a preferred 3.6 mm, the vent body 602 includes a recess 628 on the upper surface 604 of the vent body 602 surrounding the vent apertures 626 that reduces the thickness of the vent body 602 in the region of the vent apertures 626. The recess 628 can have other configurations and be positioned on the lower surface 606 of the vent body 602 or even be positioned on both upper and lower surfaces of the vent body 602. The length of the vent apertures 626 can be altered as desired by using one or more recesses on either side of the vent body 602 to vary the thickness of the vent body 602 in the region of the vent apertures 626. The overall thickness of the vent body 602 can also be altered as desired to affect the length of the vent apertures, but a certain minimum thickness is generally preferred to provide the necessary rigidity to the vent 600 to remain in the desired position on the shell 40. Thus, the use of a recess allows the overall vent thickness to meet the desired minimum thickness while still providing a desired vent aperture length. The configuration of the recess can also be altered to operate in conjunction with the vent apertures 626 to provide different flow characteristics to the vent 600. Other recesses 630 can also be positioned elsewhere on the vent body 602 where the rigidity of the vent 600 is less critical to reduce the amount of material needed to mold the vent 600.

Cushion/Shell Connection Mechanism

The mask assembly of this embodiment uses a cushion/shell connection mechanism similar to the mechanism shown in FIG. 65. See especially, FIGS. 68, 73, 88 and 89. In FIG. 73, the shell 40 includes a channel 500 running around a cushion side periphery. The channel 500 is surrounded by an inner wall 502, an outer wall 504 and a channel floor 506 formed by the surface 52 of shell 40. The channel 500 is configured in the generally triangular shape of the shell 40. The channel 500 includes two slots 508 that pass through the channel floor 506 to allow access to the surface 52 of the shell 40 and a third slot 509 in the outer wall 504 at the bottom of the triangle. The third slot 509 extends through the outer wall 504 of the channel 500 generally at an angle of 90° to the slots 508.

Figures 74, 75:
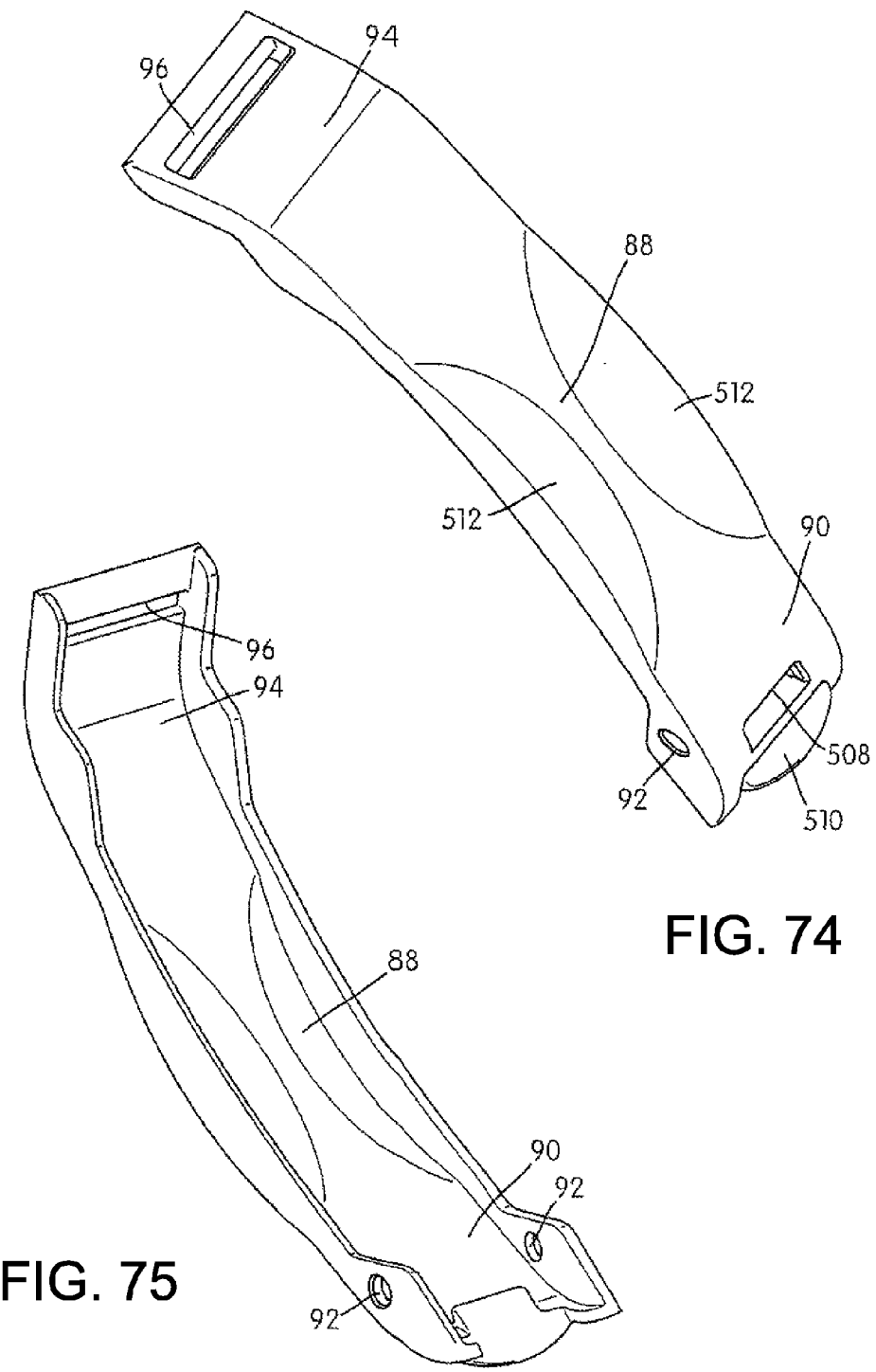
FIG. 74 shows a front perspective view of a clip of a latching mechanism of the embodiment of FIG. 68.
FIG. 75 shows a rear perspective view of the clip of FIG. 74.
Figure 88:
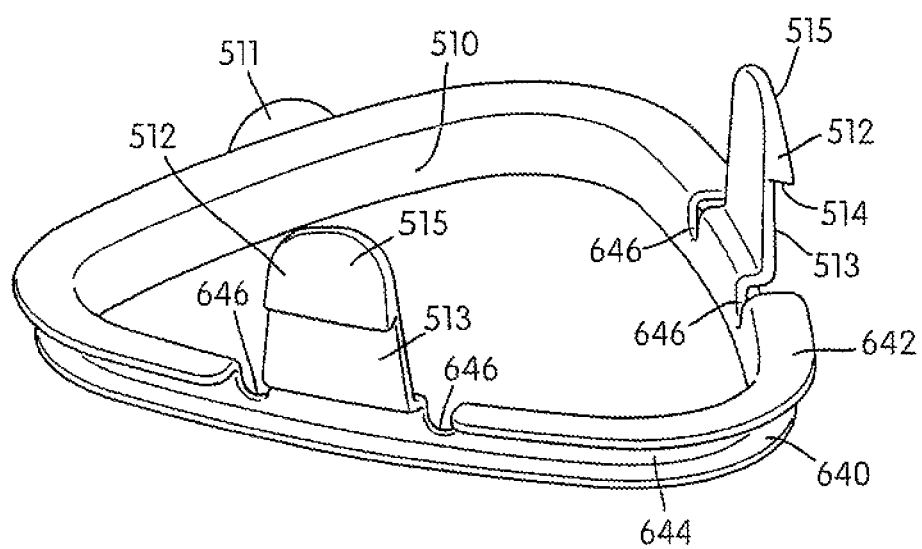
FIG. 88 shows a perspective view of a retaining ring of a cushion/shell connection mechanism of the embodiment of FIG. 68.

In FIGS. 74 and 69, the mechanism includes a retaining ring 510 configured to have a similar general shape as the channel 500. The retaining ring 510 has two clips 512 positioned on two respective spring arms 513. The clips 512 are positioned and configured to pass through the respective slots 508 such that an underside lip 514 of each clip 512 engages the surface 52 when the retaining ring 510 is positioned in the channel 500. In FIG. 88, an upper surface 515 of each clip 512 is beveled to provide easier passage through the slot 508. The retaining ring 510 also includes a retaining tab 511 positioned on the remaining third side of the retaining ring 510 that does not include a clip 512. The retaining tab 511 extends outward from the retaining ring 510, generally in a plane at 90° to the planes in which the clips 512 generally extend. The retaining tab 511 is adapted to engage the retaining slot 508.

In FIG. 88, the retaining ring 510 includes a lower retaining lip 640, an upper retaining lip 642 and a channel 644 positioned therebetween, all generally running around a periphery of the retaining ring 510. Notches 646 on the sides of each clip 512 cut through the upper lip 642 and into the channel 644 to increase the flexibility of the clips 512.

Figure 89:
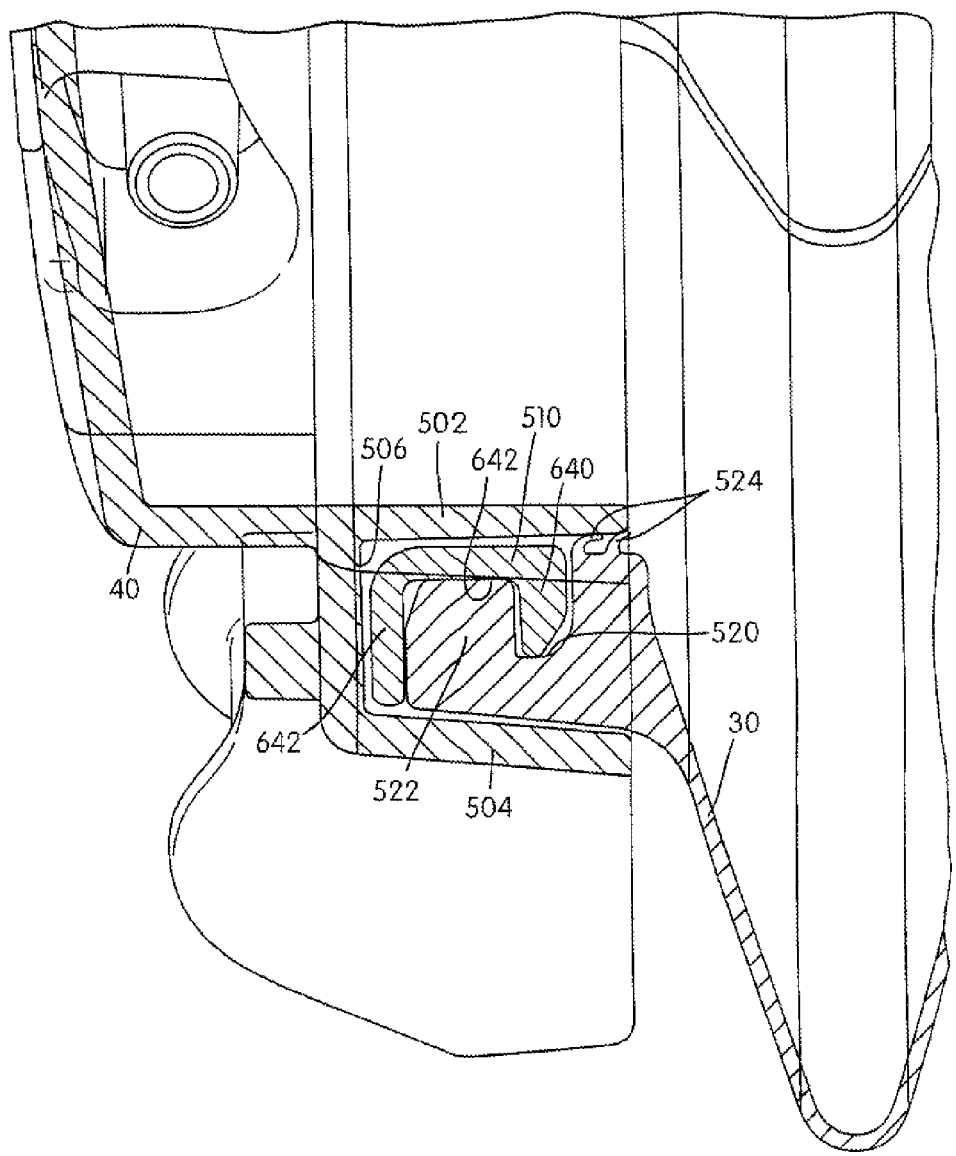
FIG. 89 shows a partial sectional view of a cushion/shell connection mechanism of the embodiment of FIG. 68.

In FIG. 89, the cushion 30 includes a retaining channel 520 and a retaining lip 522 extending outward from the channel 520. The retaining channel 520 is configured to snugly engage the lower retaining lip 640 of the retaining ring 510 and the retaining lip 522 is configured to snugly engage the retaining ring channel 644 between the lower lip 640 and the upper lip 642 when the cushion 30 is installed on the retaining ring 510. The cushion 30 also includes a pair of sealing lips 524 that extend from the cushion 30 to engage the inner wall 502 of the channel 500 around an entire inner periphery of the cushion 30 to provide a continuous airtight seal between the cushion 30 and the shell 40. The sealing lips 524 are flexible to assure a sealing contact with the shell 40. The sealing lips 524 are shown in the position they would assume when the cushion 30 is mounted to the shell but would return to a relaxed state when the cushion 30 is disassembled from the shell 40. This deformation of the flexible sealing lips 524 also applies a tension to the cushion/retaining ring/retaining clips when installed to help maintain a secure connection between the connection mechanism and the shell 40. One or more sealing lips 524 may be employed.

This embodiment does not clamp a portion of the cushion 30 between the retaining ring 510 and the channel floor 506, as does the embodiment shown in FIG. 65, but relies only on the contact between the sealing lips 524 and the shell 40 to provide an airtight seal between the cushion 30 and the shell 40. In this embodiment, the retaining ring/cushion assembly is positioned at an angle in the channel 500 with the bottom side of the triangle in the channel 500 and the top two sides of the triangle pivoted slightly out of the channel 500 so that the retaining tab 511 can engage the retaining slot 508. Then, the retaining ring/cushion assembly 510 is pivoted upward toward the shell 40 so that the remaining portions of the retaining ring move into the channel 500 and the clips 512 engage the slots 508 to lock the retaining ring 510 into place with respect to the shell 40. In this manner, the retaining tab 511 and retaining slot 508 provide additional clamping force between the retaining ring 510 and shell 40 at the bottom side of the retaining ring 510, as compared to the embodiment shown in FIG. 65. Disassembly is performed by squeezing the clips 512 together, as in the embodiment shown in FIG. 65, and pivoting the retaining ring 510 out of the channel 500 until the retaining tab 511 can be disengaged from the retaining slot 509 and the retaining ring/cushion assembly can be completely disengaged from the shell 40.

Figure 92:
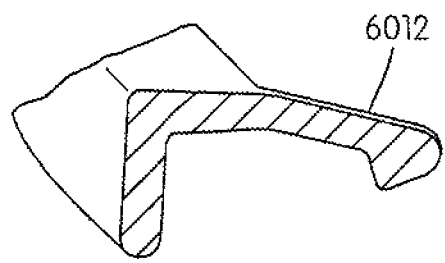
FIG. 92 shows a detailed view of the clip portion of the retaining ring of FIGS. 90A-90D.

In FIG. 92, the shell 40 also includes a pair of spaced apart, downwardly projecting access ports 118, as described above, positioned in a recess 592 located at a bottom portion of the shell 40.

FIGS. 90A-90D illustrate multiple views of retaining ring 6010 in an alternate embodiment of the present invention. As shown in the front view of FIG. 90C, the retaining ring 6010 is of a generally triangular shape and includes two (2) clip portions 6012 and a retaining tab 6013. The retaining ring 6010 has a base 6014 and two sides 6016. Shapes other than the generally triangular shape depicted in FIG. 90C may be used, as well as a number of sides 6016 other than two.

As illustrated in FIGS. 90B and 90D, clip portion 6012 extends out from the retaining ring 6010. The clip portions 6012 may be adapted to resiliently flex outwardly or inwardly in the direction of arrows 6020 or 6022 respectively. FIG. 90B shows the retaining ring 6010 along the reference line 90A-90B of FIG. 90C. FIG. 90D shows a right side view of the retaining ring 6010. FIG. 90A shows the retaining ring 6010 along the reference line 90A-90A of FIG. 90C.

Figure 91A:
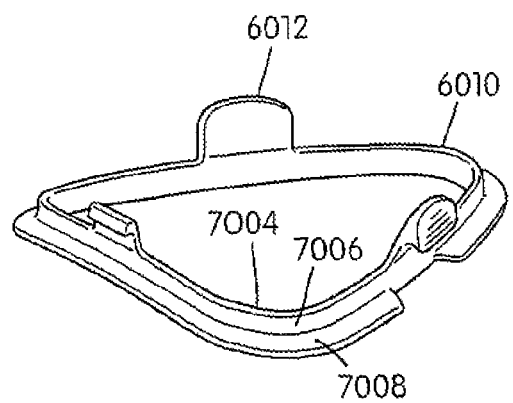
FIGS. 91A-91C shows isometric views of the retaining ring of FIGS. 90A-90D.
Figure 91B:
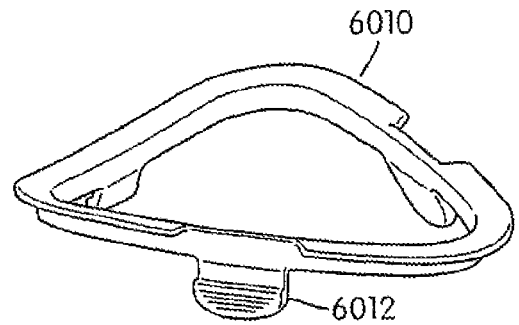
Figure 91C:
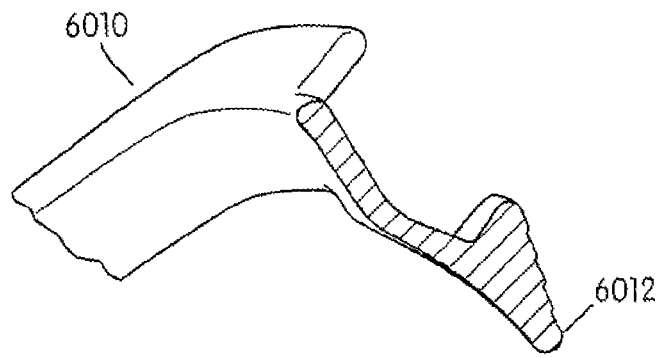

FIGS. 91A-90C illustrate multiple isometric view of the retaining ring 6010. In FIG. 91A, retaining ring 6010 has a frontwardly projecting wall 7004 with an outer surface 7006 and an inner surface 7008. In the underside, isometric view of FIG. 91B, the clip portion 6012 includes a ribbed surface to provide a gripping surface for the finger of the user. FIG. 91C shows an enlarged detail view of the ribbed surface of clip portion 6012.

FIG. 92 shows a detailed view of the clip portion 6012. Clip portion 6012 may protrude from the retaining ring at an angle in a range between 77°-97°, preferably 87°.

Figure 93:
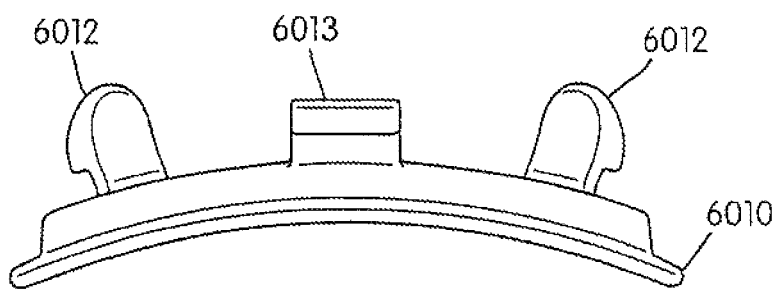
FIG. 93 shows on underside view of the retaining ring and clip of FIGS. 90A-90D.

FIG. 93 shows the underside view of the retaining ring 6010 having two clip portions 6012, a retaining tab 6013 and a radius of curvature in a range of 94.00 mm-114.00 mm, preferably 104.00 mm.

Figure 94A:
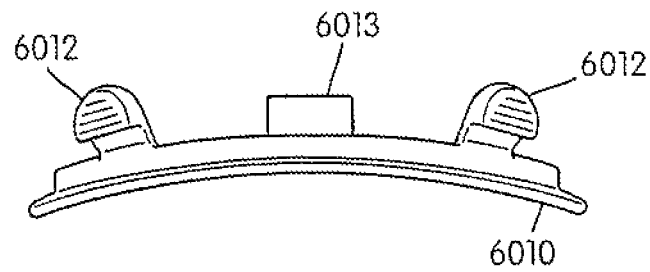
FIGS. 94A-94B show top and back view of the retaining ring of FIGS. 90A-90D.
Figure 94B:
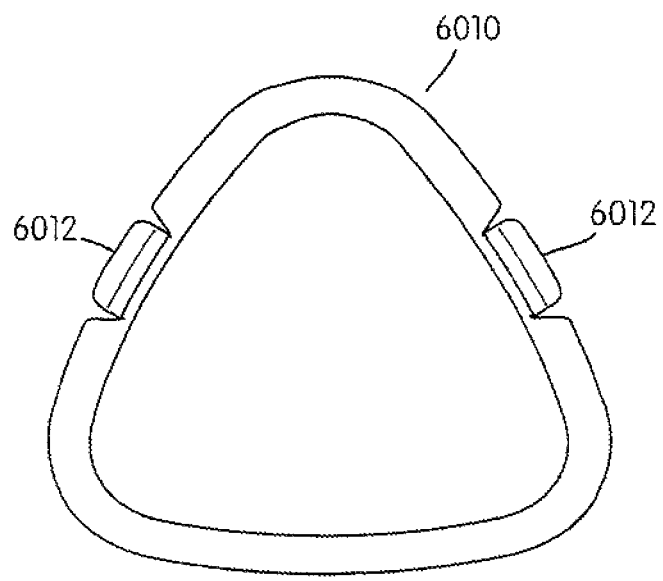

FIGS. 94A and 94B show the top and back views, respectively, of the retaining ring 6010 having clip portions 6012 and retaining tab 6013.

Figure 95:
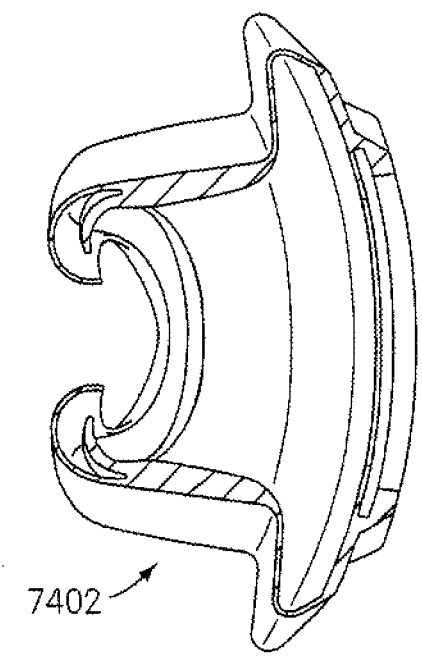
FIG. 95 shows a perspective view of a cushion in an alternate embodiment of the present invention.
Figure 98A:
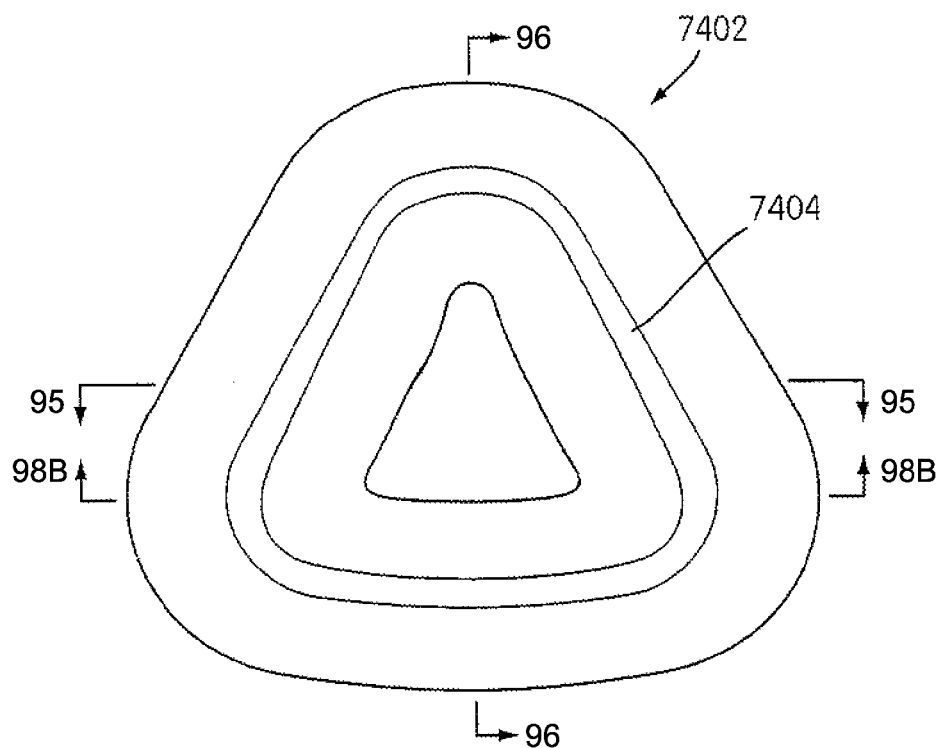
FIGS. 98A-98B show front and perspective views of the cushion of FIG. 95.

FIG. 95 shows a perspective view of a cushion 7402 along the reference line 95-95 of FIG. 98A and having a radius of curvature in a range between 88°-108°, preferably 98°.

Figure 96:
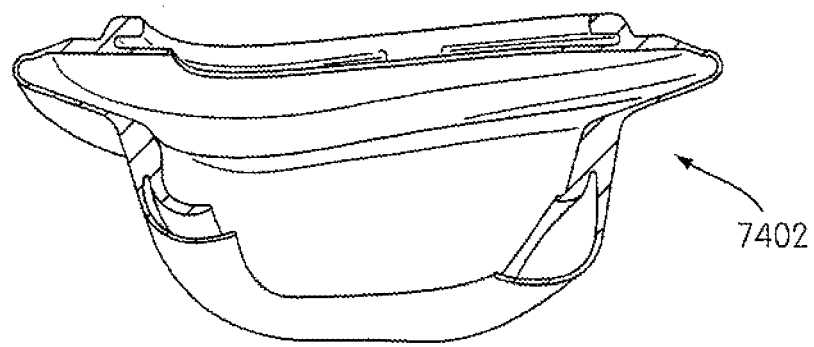
FIG. 96 shows a side view of the cushion of FIG. 95.

FIG. 96 shows a side perspective view of the cushion 7402 along the reference line 96-96 of FIG. 98A.

Figure 97A:
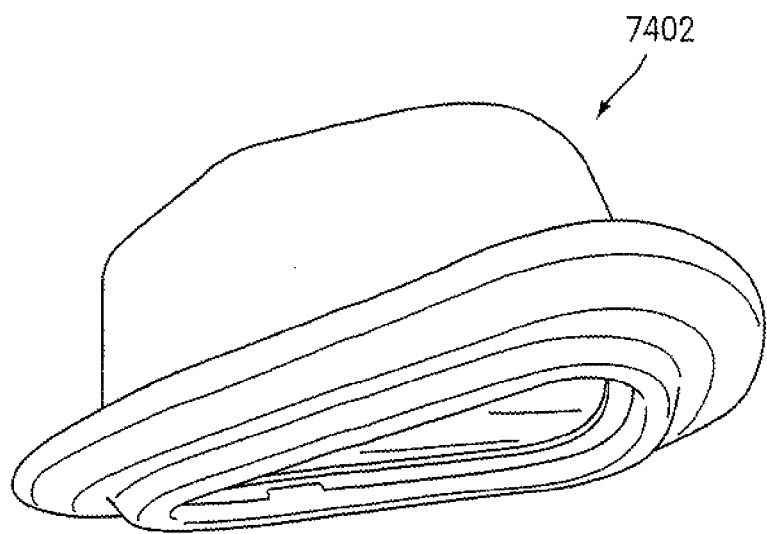
FIGS. 97A-97B show side elevational views of the cushion of FIG. 95.
Figure 97B:
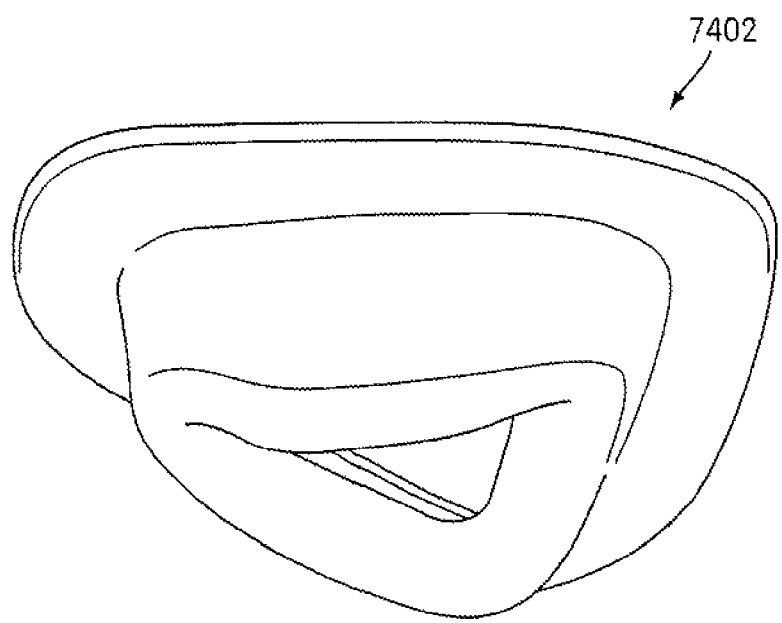

FIGS. 97A and 97B show a side and underside view, respectively of the cushion 7402.

Figure 98B:
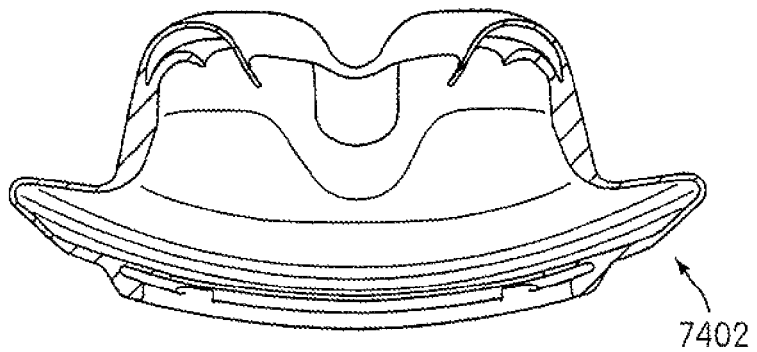

FIG. 98A shows the cushion 7402 having gusset portions 7404. FIG. 98B shows a detailed view of the gusset portions 7404 along the reference line 98B-98B of FIG. 98A.

Figure 99A:
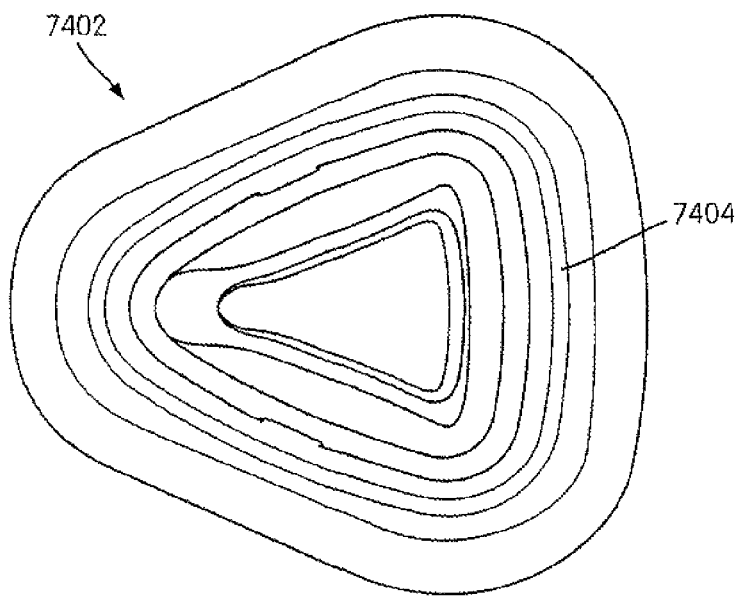
FIGS. 99A-99B show further front and perspective views of the cushion of FIG. 95.
Figure 99B:
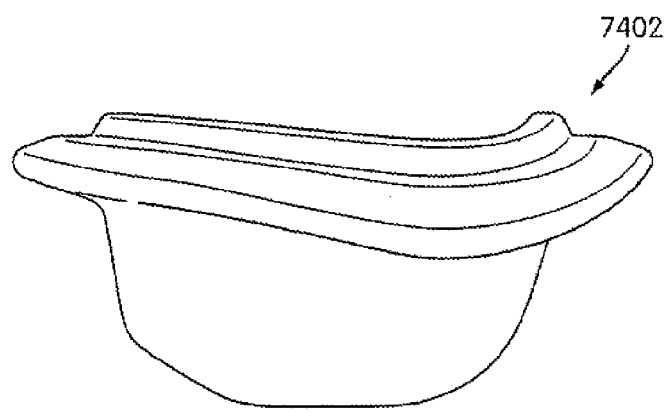

FIGS. 99A and 99B show front and side views of the cushion 7402 having a thickness in the range 42.0 mm-62.0 mm, preferably 52.0 mm.

Figure 100:
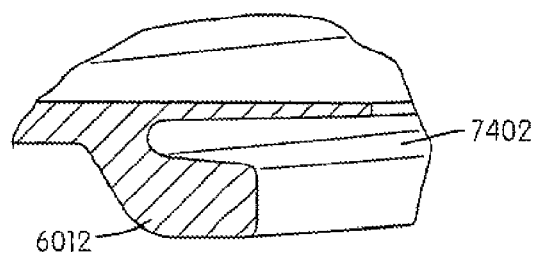
FIG. 100 shows a sectional view of the cushion of FIG. 95.

FIG. 100 shows a sectional view of the cushion 7402 and clip portion 6012.

Figure 101:
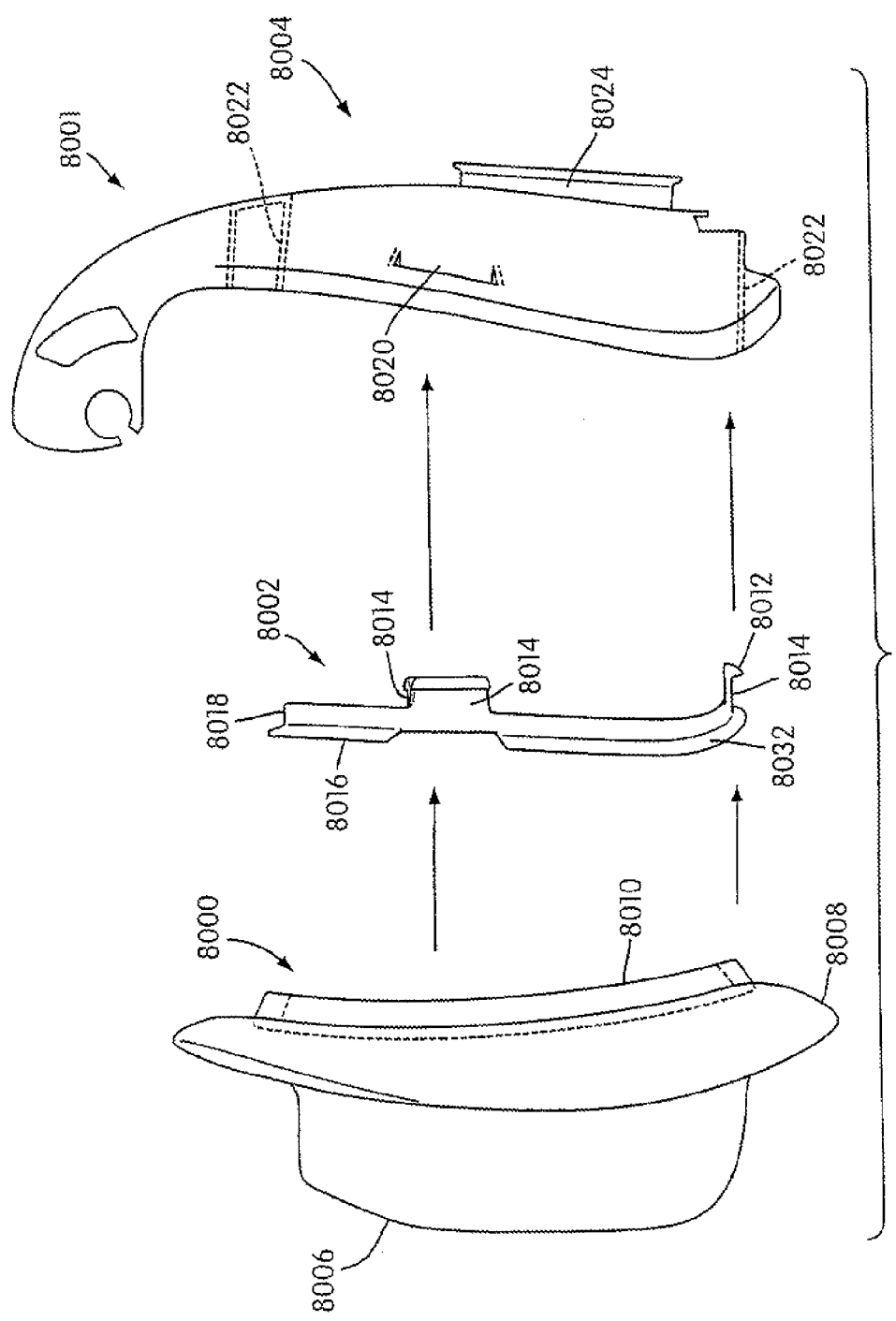
FIG. 101 shows an exploded side view of an alternate embodiment of the present invention.

FIG. 101 shows an exploded side view of an alternate embodiment of the mask assembly of the present invention. The mask assembly 8001 has a cushion 8000, a retaining ring 8002 and shell 8004. The cushion 8000, having a seal-forming membrane 8006 and gusset portion 8008 is assembled around the retaining ring 8002 by engaging the flange portions 8016 and 8032 of the retaining ring 8022 into a shoulder portion 8010 of the cushion 8000. The cushion and retaining ring assembly is inserted into the shell 8004 by inserting the clip portions 8012 into the slot portions 8020 of the shell 8004 to engage an underside of the shell 8004. The slot portions 8020 are located in the inner wall of the shell 8004. There is one slot portion 8020 and clip portion 8012 depicted in FIG. 101; however more than one clip portion and slot portion may be used.

Figure 102:
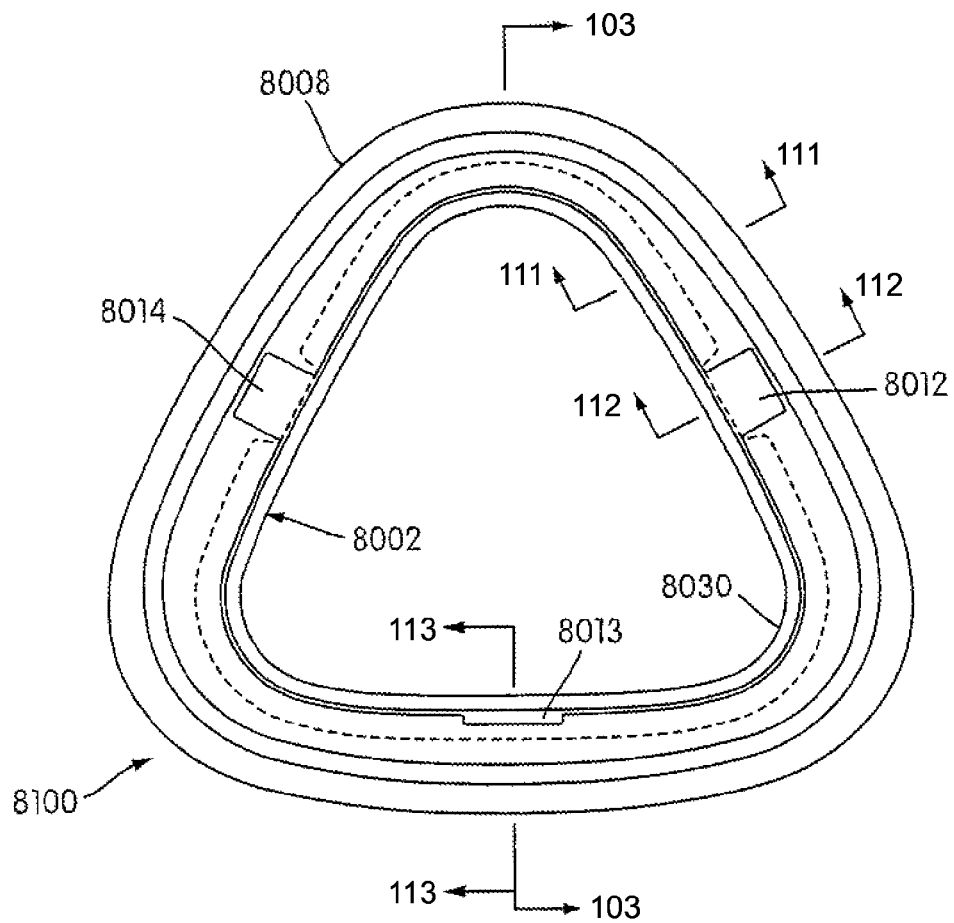
FIG. 102 shows a front view of the cushion and ring assembly of the embodiment in FIG. 101.
Figure 103:
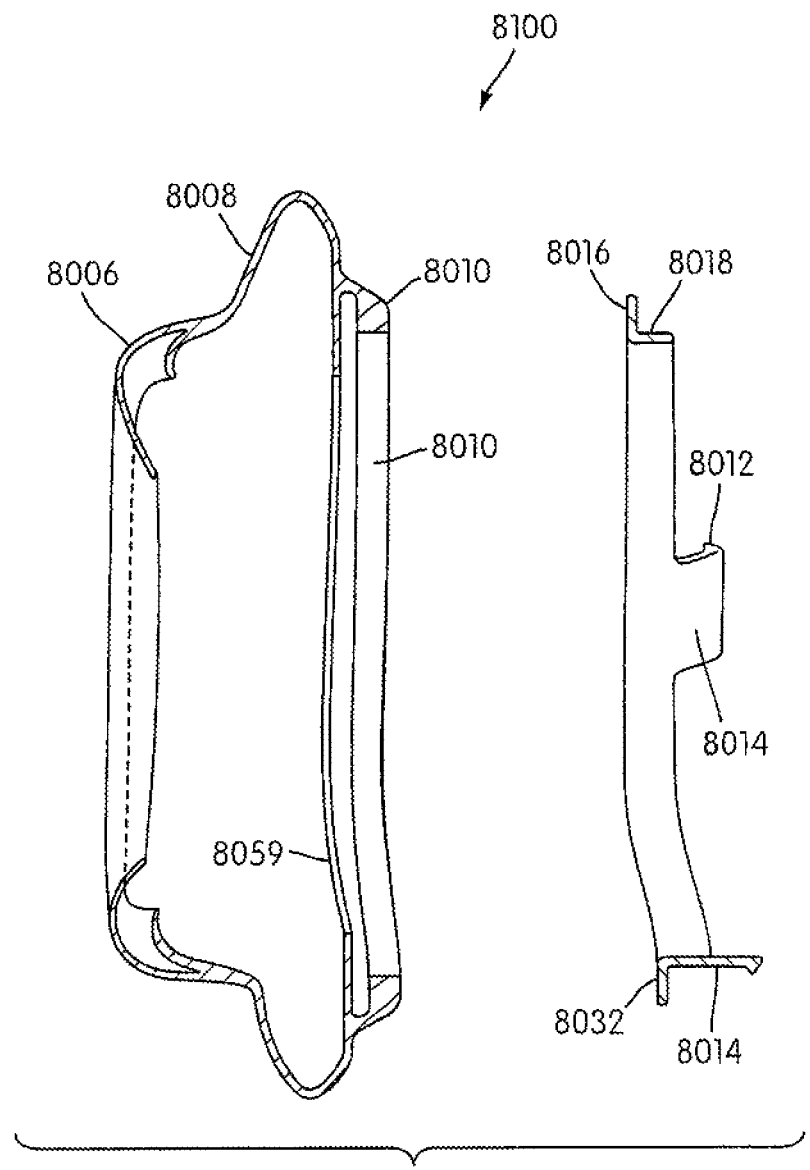
FIG. 103 shows a exploded view of the cushion and ring assembly of FIG. 102.

FIG. 102 shows a front view of the cushion and ring assembly 8100 of the embodiment of FIG. 101 having two clip portions 8012 and retaining tab 8013. FIG. 103 shows an exploded sectional view of the cushion and ring assembly 8100 of FIG. 102 along the reference line 103-103.

Figure 104:
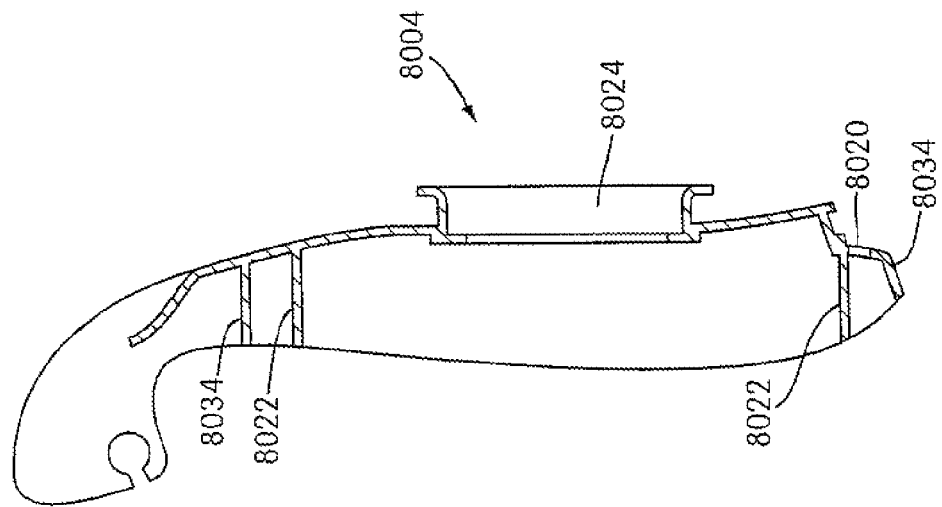
FIG. 104 shows a side cross-sectional view of the mask in the alternate embodiment of FIG. 101.

FIG. 104 shows a side cross-sectional view of the shell 8004 of FIG. 101. In FIG. 104, shell 8004 has an inner wall 8022 and outer wall 8034 such that a clip portion 8012 of the cushion and retaining ring assembly may be received through the slot 8020 between the inner wall 8022 and the outer wall 8034.

Figure 105:
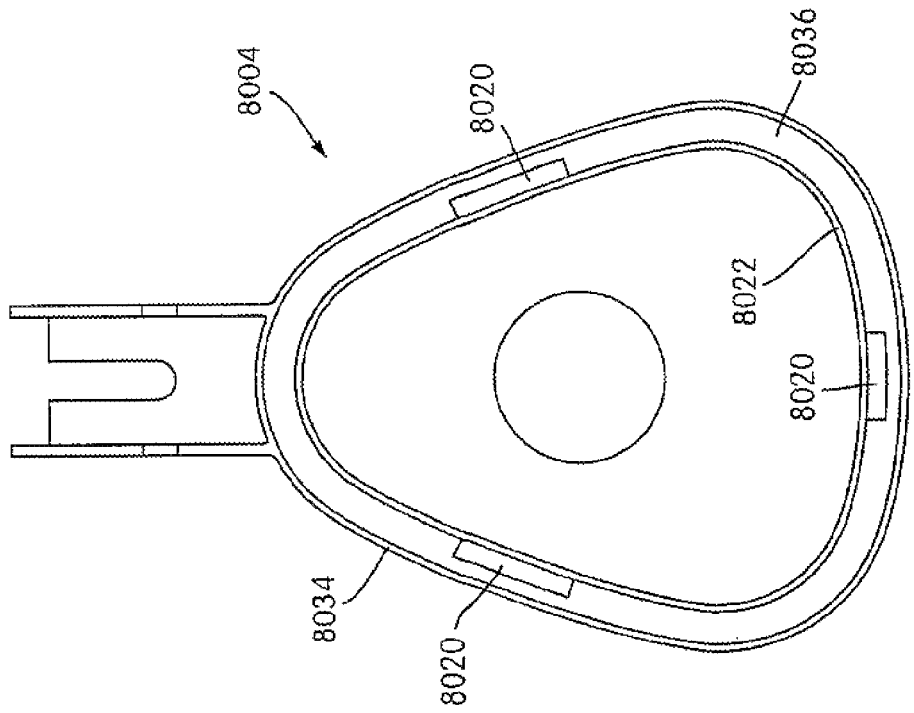
FIG. 105 shows a rear view of the mask of FIG. 104.

FIG. 105 shows a rear view of the shell 8004 of FIGS. 101 and 104 in which a channel 8036 is located between the outer wall 8034 and the inner wall 8022 of the shell 8004. The shell 8004 has three slot portions 8020 to receive the clip portions and retaining tab from the cushion and retaining ring assembly.

Figure 106:
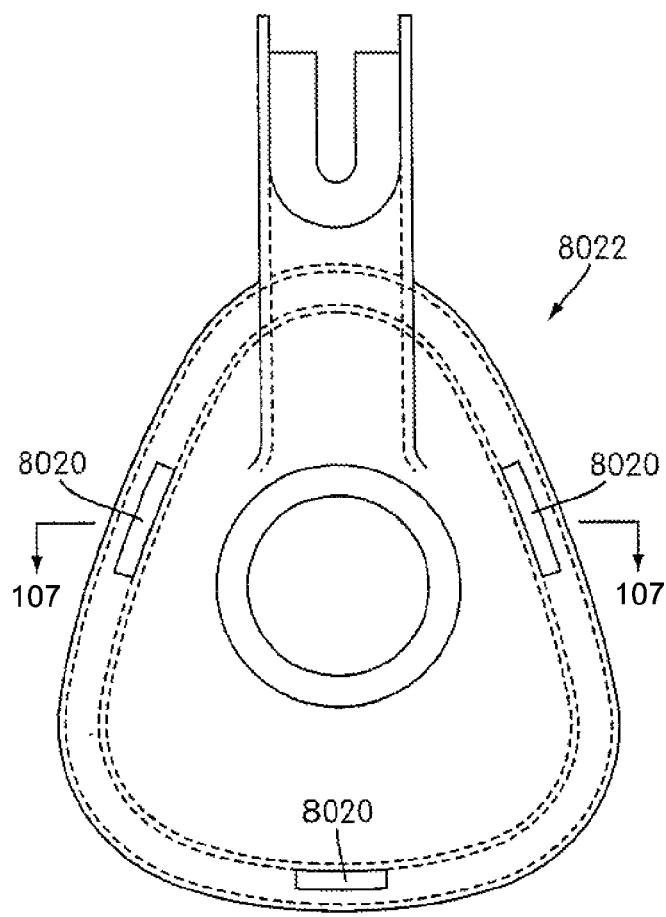
FIG. 106 shows a front view of the mask of FIG. 104.
Figure 107:
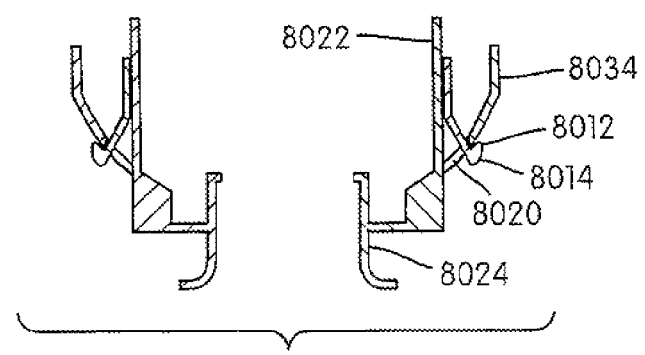
FIG. 107 shows the mask and ring assembly along a reference point 107-107 of FIG. 106.

FIG. 106 shows a front view of the shell 8004 having three slots 8022 and a reference line 107-107. FIG. 107 shows a sectional view of the cushion and retaining ring assembly and shell along the reference line 107-107 of FIG. 106.

Figure 108:
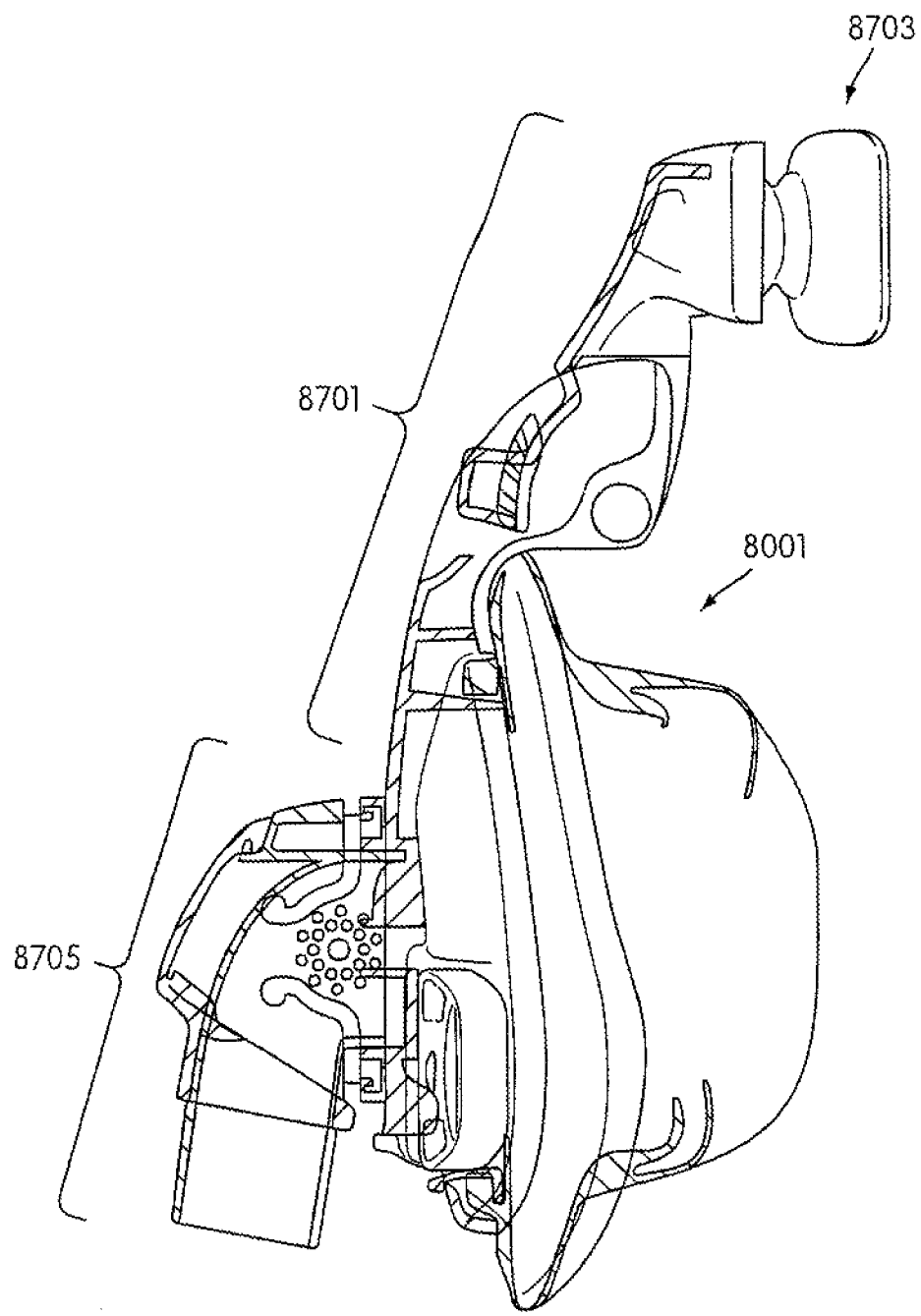
FIG. 108 shows a side view of alternate embodiment of FIG. 101.
Figure 109:
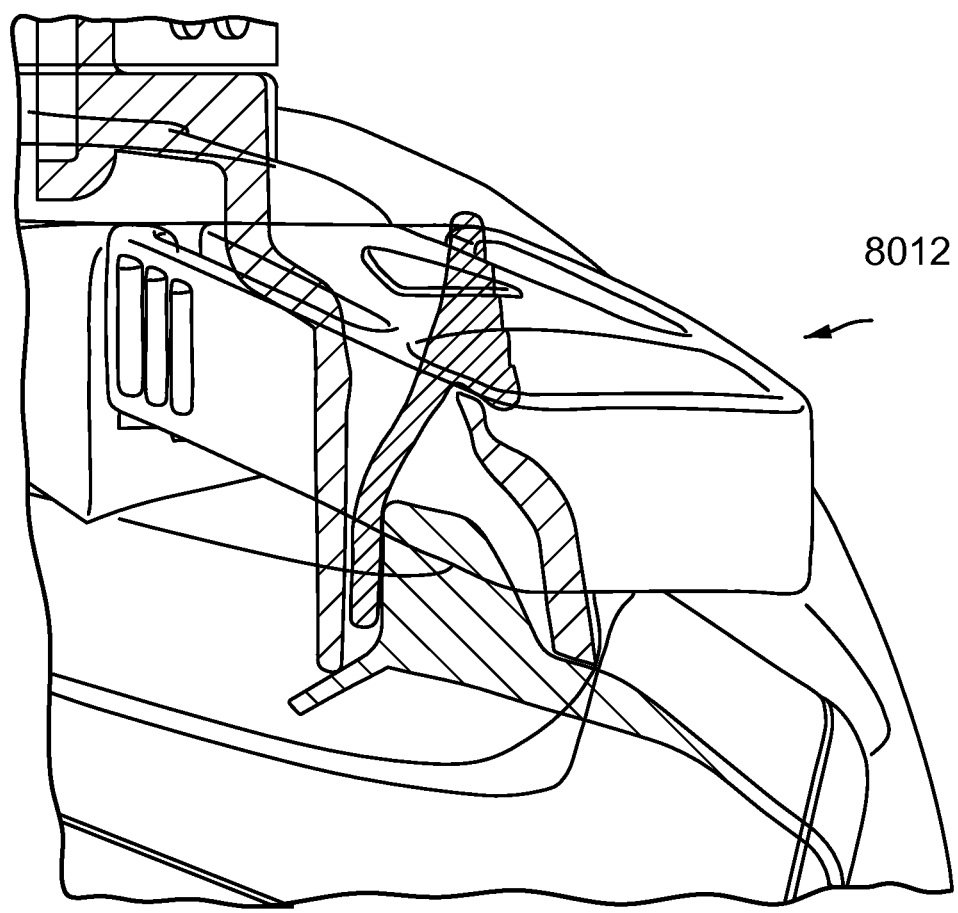
FIG. 109 shows a cross-section view of an upper detent of the embodiment of FIG. 101.
Figure 110:
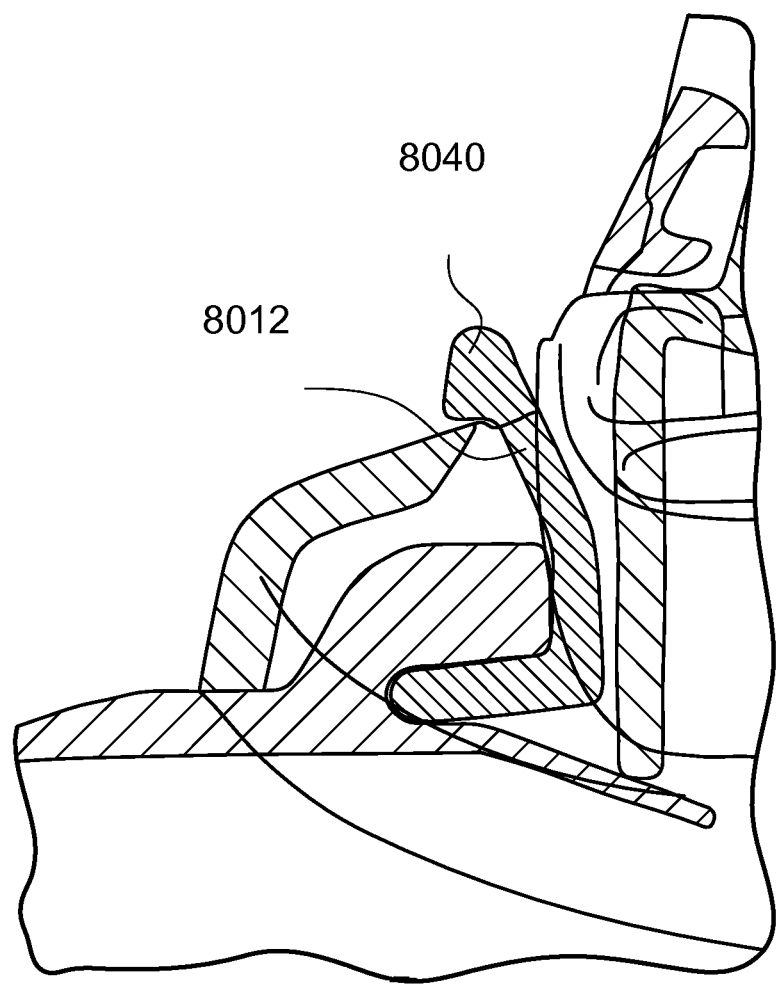
FIG. 110 shows a cross-section view of a lower detent of the embodiment of FIG. 101.

FIG. 108 shows a side view of the mask assembly 8001 of FIG. 101. FIGS. 109 and 110 show cross sections of the upper and lower clip portions 8012 having a flange portion 8040. In FIG. 108, the mask assembly 8001 includes the fully assembled cushion and retaining ring assembly inserted into the shell, as well as the head mount portion 8701 and air inlet section 8705. The head mount portion 8701 includes a mechanism 8703 to stabilize the mask assembly on the user.

Figure 111:
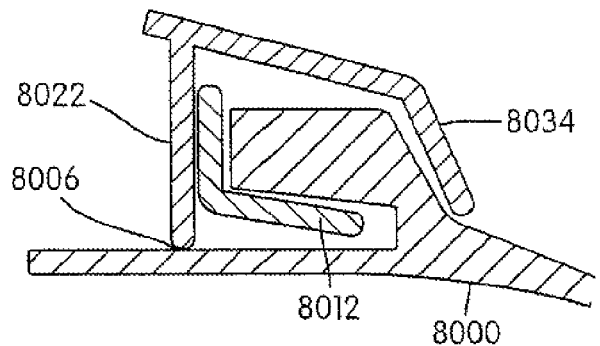
FIG. 111 shows a cross-sectional view of the alternate embodiment of the mask assembly shown in FIG. 101.
Figure 112:
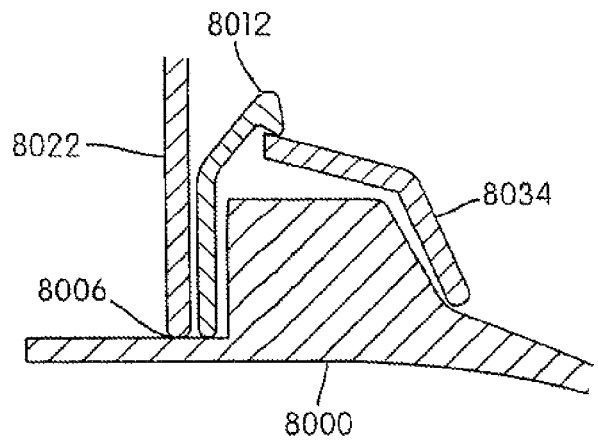
FIG. 112 shows a cross-sectional view of the alternate embodiment of the mask assembly shown in FIG. 101.
Figure 113:
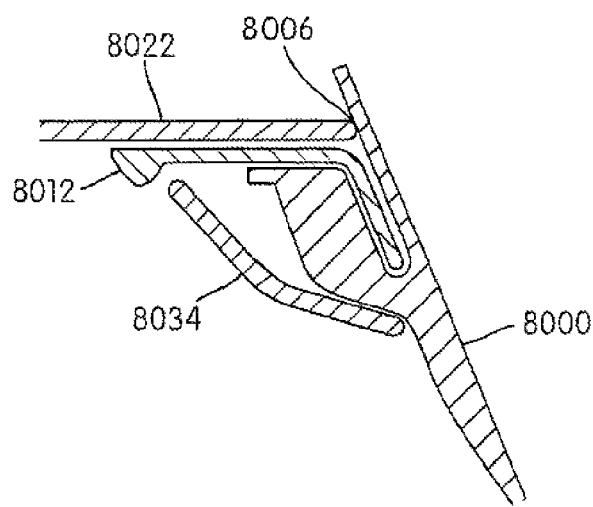
FIG. 113 shows a cross-sectional view of the alternate embodiment of the mask assembly shown in FIG. 101.

FIGS. 100-103 show cross-sectional views of the cushion and ring assembly inserted in the inner wall of the shell. The clip portion 8012 of the cushion and retaining ring are secured to the shell by the seal forming portion 8006. FIG. 111 shows the cushion and retaining ring assembly inserted in the shell along the reference line 111-111 in FIG. 102. FIG. 112 shows the cushion and ring assembly inserted in the shell along the reference line 112-112 in FIG. 102. FIG. 113 shows the cushion and ring assembly inserted in the shell along the reference line 113-113 in FIG. 102.

In FIGS. 109 and 112, the flange portion 8040 of the upper clips 8012 has an undercut to improve retention in the frame or shell. In contrast, the flange portion of the lower clip 8012 of FIGS. 110 and 113 has an angled profile to permit easy disassembly.

It is intended that the components, elements and features of the various above-described embodiments can be used together in any desired combination or permutation to create new mask embodiments. For example, while the invention has been described in relation to a nasal mask, the teachings are also applicable to nasal/oral masks as well.

The invention claimed is:

1. A respiratory patient interface assembly for use in delivery of non-invasive positive airway pressure to a user comprising:
   a rigid patient interface shell including an inner wall and a plurality of slots;
   a soft cushion including a seal-forming membrane structured to form a seal with the user's face and at least one flexible sealing lip constructed and arranged to extend radially inward beyond the inner wall from an inner periphery of the cushion and to deform to provide a continuous airtight seal between the cushion and the rigid patient interface shell, the at least one flexible sealing lip being further constructed and arranged to return to a relaxed state when the cushion is disassembled from the rigid patient interface shell; and
   a retaining ring coupled to the cushion, and including a plurality of clips each positioned on respective spring arms to engage with each of the respective plurality of slots of the rigid patient interface shell to retain the cushion in position with the rigid patient interface shell in use.

2. The respiratory patient interface assembly of claim 1, constructed and arranged to rely only on contact between the at least one flexible sealing lip and the rigid patient interface shell to provide an airtight seal between the cushion and the rigid patient interface shell.

3. The respiratory patient interface assembly of claim 1, wherein each of the plurality of clips includes an underside lip adapted to engage a surface of the rigid patient interface shell.

4. The respiratory patient interface assembly of claim 3, wherein said underside lip includes a beveled surface.

5. The respiratory patient interface assembly of claim 1, wherein the retaining ring further includes a retaining tab.

6. The respiratory patient interface assembly of claim 5, wherein the plurality of clips each extend from the retaining ring in respective first directions along respective planes, and wherein the retaining tab is constructed and arranged to extend outwardly from respective ones of the plurality of clips generally in a plane at 90 degrees to the respective first directions that the respective planes of the plurality of clips generally extend.

7. The respiratory patient interface assembly of claim 1, wherein the plurality of clips is constructed and arranged to be squeezed together to initiate disengagement of the soft cushion from the rigid patient interface shell.

8. The respiratory patient interface assembly of claim 1, wherein a retaining portion extends inwardly from the inner periphery of the cushion parallel to the at least one flexible sealing lip, the retaining portion and the at least one flexible sealing lip being spaced apart such that the retaining ring is positioned between the at least one flexible sealing lip and the retaining portion when the retaining ring is engaged with the retaining portion.

9. The respiratory patient interface assembly of claim 1, wherein the cushion and the patient interface shell at least partially define a chamber, and
   wherein the at least one flexible sealing lip extends toward the chamber from the inner periphery of the cushion.

10. The respiratory patient interface assembly of claim 9, wherein the at least one flexible sealing lip extends into the chamber and beyond an inner periphery of the retaining ring.

11. The respiratory patient interface assembly of claim 1, wherein the inner wall is structured to contact and deform the at least one flexible sealing lip when the cushion is assembled to the patient interface shell.

12. The respiratory patient interface assembly of claim 1, wherein the inner wall extends from the patient interface shell and the at least one flexible sealing lip extends from the inner periphery of the cushion substantially perpendicular to the inner wall.

13. The respiratory patient interface assembly of claim 1, wherein an inner edge of the at least one flexible sealing lip extends beyond the inner wall when the cushion and the retaining ring are engaged with the patient interface shell.

14. The respiratory patient interface assembly of claim 1, wherein the patient interface shell comprises an outer wall spaced from the inner wall such that the retaining ring extends between the inner wall and the outer wall when the retaining ring is engaged with the patient interface shell.

15. The respiratory patient interface assembly of claim 14, wherein the plurality of slots are positioned between the inner wall and the outer wall.

16. The respiratory patient interface assembly of claim 1, wherein the at least one flexible sealing lip extends from the inner periphery of the cushion such that the at least one flexible sealing lip is deflected in a direction away from the patient interface shell when the cushion is engaged with the patient interface shell.

17. The respiratory patient interface assembly of claim 1, wherein the at least one flexible sealing lip extends from the inner periphery of the cushion in a direction substantially perpendicular to a direction of engagement between the cushion and the patient interface shell.

18. The respiratory patient interface assembly of claim 1, further comprising nasal prongs or a nasal cushion.

19. The respiratory patient interface assembly of claim 1, wherein the patient interface shell further comprises a vent.

20. The respiratory patient interface assembly of claim 1, wherein the at least one flexible sealing lip is positioned on an opposite side of the cushion from the seal-forming membrane.

21. A respiratory patient interface assembly for use in delivery of non-invasive positive airway pressure to a user comprising:
- a patient interface shell including an inner wall;
- a cushion including a seal-forming membrane structured to form a seal with the user's face, the cushion having at least one flexible sealing lip structured to extend radially inward from an inner periphery of the cushion; and
- a retaining ring coupled to the cushion and configured to attach the cushion to the patient interface shell,
- wherein the at least one flexible sealing lip is positioned to contact the inner wall when the cushion and the retaining ring are attached to the patient interface shell such that the at least one flexible sealing lip forms a seal with the inner wall.

22. The respiratory patient interface assembly of claim 21, wherein the patient interface shell further comprises a plurality of slots, and
- wherein the retaining ring includes a plurality of clips structured to engage with respective ones of the plurality of slots of the patient interface shell to retain the cushion in position with the patient interface shell.

23. The respiratory patient interface assembly of claim 22, wherein the patient interface shell comprises an outer wall spaced from the inner wall to define a channel such that the retaining ring extends into the channel when the retaining ring is engaged with the patient interface shell.

24. The respiratory patient interface assembly of claim 23, wherein the plurality of slots are positioned in the channel.

25. The respiratory patient interface assembly of claim 21, wherein the at least one flexible sealing lip is further structured to deform to provide a continuous airtight seal between the cushion and the patient interface shell, the at least one flexible sealing lip being further constructed and arranged to return to a relaxed state when the cushion is disassembled from the patient interface shell.

26. The respiratory patient interface assembly of claim 21, wherein a retaining portion extends inwardly from the inner periphery of the cushion parallel to the at least one flexible sealing lip, the retaining portion and the at least one flexible sealing lip being spaced apart such that the retaining ring is positioned between the at least one flexible sealing lip and the retaining portion when the retaining ring is engaged with the retaining portion.

27. The respiratory patient interface assembly of claim 21, wherein the cushion and the patient interface shell at least partially define a chamber, and
- wherein the at least one flexible sealing lip extends toward the chamber from the inner periphery of the cushion.

28. The respiratory patient interface assembly of claim 27, wherein the at least one flexible sealing lip extends past the inner wall and into the chamber.

29. The respiratory patient interface assembly of claim 21, wherein the at least one flexible sealing lip is deflected in a direction away from the patient interface shell when the cushion and the retaining ring are attached to the patient interface shell.

30. The respiratory patient interface assembly of claim 21, further comprising nasal prongs or a nasal cushion.

31. The respiratory patient interface assembly of claim 21, wherein the patient interface shell further comprises a vent.

* * * * *